US009096825B2

(12) United States Patent
Schmid et al.

(10) Patent No.: US 9,096,825 B2
(45) Date of Patent: Aug. 4, 2015

(54) 7 α-HYDROXYSTEROID DEHYDROGENASE KNOCKOUT MUTANTS AND USE THEREFOR

(75) Inventors: Rolf Schmid, Stuttgart (DE); Michael Braun, Bad Mergentheim-Edelfingen (DE); Luo Liu, Beijing (CN); Arno Aigner, Tuntenhausen (DE); Dirk Weuster-Botz, München (DE)

(73) Assignee: Pharmazell GmbH, Raubling (DE)

( * ) Notice: Subject to any disclaimer, the term of this patent is extended or adjusted under 35 U.S.C. 154(b) by 0 days.

(21) Appl. No.: 13/699,239

(22) PCT Filed: May 27, 2011

(86) PCT No.: PCT/EP2011/058711
§ 371 (c)(1),
(2), (4) Date: May 3, 2013

(87) PCT Pub. No.: WO2011/147957
PCT Pub. Date: Dec. 1, 2011

(65) Prior Publication Data
US 2013/0224792 A1 Aug. 29, 2013

(30) Foreign Application Priority Data

May 27, 2010 (EP) ..................................... 10164003
Dec. 16, 2010 (EP) ..................................... 10015726

(51) Int. Cl.
*C12P 33/00* (2006.01)
*C12N 9/04* (2006.01)
*C12N 1/20* (2006.01)
*C12N 15/00* (2006.01)
*C12N 15/87* (2006.01)
*C07K 14/245* (2006.01)
*C12P 33/06* (2006.01)

(52) U.S. Cl.
CPC ............ *C12N 9/0006* (2013.01); *C07K 14/245* (2013.01); *C12P 33/00* (2013.01); *C12P 33/06* (2013.01); *C12Y 101/01159* (2013.01)

(58) Field of Classification Search
CPC .... C12N 9/00; C12N 2501/70; C12N 9/0006; C07K 14/245; C12Y 101/01159; C12P 33/06; C12P 33/00
USPC ......................... 435/52, 190, 252.33, 440, 463
See application file for complete search history.

(56) References Cited

U.S. PATENT DOCUMENTS

2011/0091921 A1* 4/2011 Aigner et al. .................... 435/26

FOREIGN PATENT DOCUMENTS

DE WO2009118176 A * 10/2009 ............... C12N 9/04
EP 2105500 A1 9/2009
WO 03051182 A3 8/2004
WO 2009118176 A8 10/2010

OTHER PUBLICATIONS

Aigner et al., WO2009/118176 A2 cited by ISA issued Nov. 2012.*
Hoffman et al., Understanding oligomerization in 3α-hydroxysteroid dehydrogenase/carbonyl reductase from *Comamonas testosteroni*: An in silico approach and evidence for an active protein. Jnl. Biotechnol. 129: 131-139, 2007.*
Broun et al., Catalytic plasticity of fatty acid modification enzymes underlying chemical diversity of plant lipids. Science, 1998, vol. 282: 1315-1317.*
Carrea et al., Enzymatic preparation of 12-Ketochendeoxycholic acid with NADP regeneration. Biotechnol. Bioeng., 198, vol. XXVI: 560-563.*
Chica et al., Semi-rational approaches to engineering enzyme activity: combining the benefits of directed evolution and rational design. Curr. Opi. Biotechnol., 2005, vol. 16: 378-384.*
Coleman et al., Characterization and regulation of the NADP-linked 7 alpha-hydroxysteroid dehydrogenase gene from *Clsostridium sordellii*. J. Bacteriol., 1994, vol. 176 (16): 4865-4874.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Maser et al., Functional expression, purification, and characterization of 3a-hydroxysteroid dehydrogenase/carbonyl reductase from *Comamonas testosteroni*. Bichem. Biophys. Res. Commun., 2000, vol. 272: 622-628.*
Sen et al., Developments in directed evolution for improving enzyme functions. Appl. Biochem. Biotechnol., 2007, vol. 143: 212-223.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Yoshimoto et al., Cloning and sequencing of the 7 alpha-hydroxystreoid dehydrogenase gene from *Escherichia coli* HB101 and characterization of expressed enzyme. J. Bacteriol., 1991, vol. 173 (7): 2173-2179.*

(Continued)

*Primary Examiner* — Ganapathirama Raghu
(74) *Attorney, Agent, or Firm* — Saul Ewing LLP; Peter C. Lauro, Esq.

(57) ABSTRACT

The invention relates to 12 α-hydroxysteroid dehydrogenases, nucleic acid sequences coding for the same, expression cassettes and vectors, recombinant microorganisms containing the corresponding coding nucleic acid sequences, a method for producing said 12 α-hydroxysteroid dehydrogenases, a method for enzymatic oxidation of 12 α-hydroxysteroids using said enzyme, a method for enzymatic reduction of 12-ketosteroids using said enzyme, a method for qualitative or quantitative determination of 12-ketosteroids and/or 12α-hydroxysteroids using said 12α-hydroxysteroid dehydrogenases and a method for production of ursodesoxycholic acid, comprising the enzyme-catalyzed cholic acid oxidation using said 12 α-hydroxysteroid dehydrogenases.

22 Claims, 3 Drawing Sheets

(56) References Cited

OTHER PUBLICATIONS

Datsenko et al., One-step inactivation of chromosomal genes in *Escherichia coli* K-12 using PCR products. PNAS., 2000, vol. 97 (12): 6640-6645.*

International Preliminary Report on Patentability issued in on Nov. 27, 2012 in International Application No. PCT/EP/201058711.

International Preliminary Report on Patentability for PCT/EP2011/058711, Aug. 19, 2011, 5 pages.

E. Mobus; "Molecular Cloning, Overexpression, and Characterization of Steroid-inducible 3alpha-Hydroxysteroid Dehydrogenase/Carbonyl Reductase from *Comamonas testosteroni*. A Novel Member of the Short-Chain Dehydrogenase/Reductase SuperFamily", Journal of Biological Chemistry, vol. 273, No. 47, Nov. 20, 1998, pp. 30888-30896, XP55003957, ISSN: 0021-9258, DOI: 10.1074/jbc.273.47.30888 figures 1, 2.

Braun M et al., "12 alpha-hydroxysteroid dehydrogenase from *Clostridium* group P, strain C 48-50. Production, purification and characterization", Euroopean Journal of Biochemistry, Blackwell Publishing, Berlin, DE, vol. 196, No. 2, Mar. 14, 1991, pp. 439-450, XP002482707, ISSN: 0014-2956, p. 444, left-hand column, paragraph 2; figures 1-3.

Database UniProt [Online], Apr. 17, 2007, Sudarsanam P et al., "SubName: Full=Putative uncharacterized protein", XP002655020, retrieved from EBI accession No. Uniprot:A4ECA9, Database accession No. A4ECA9, the whole document.

International Search Report for PCT/EP2011/058711. Aug. 19, 2011, 3 pages.

\* cited by examiner

Step 1. PCR-amplified FRT-flanked resistance gene

Step 2. Transformation of a strain that expresses λ red recombinase

Step 3. Selection of antibiotic-resistant transformants

Step 4. Elimination of the resistance cassette using an FLP expression plasmid

SEQUENCE LISTING

<160> NUMBER OF SEQ ID NOS: 53

<210> SEQ ID NO 1
<211> LENGTH: 4334
<212> TYPE: DNA
<213> ORGANISM: Artificial
<220> FEATURE:
<223> OTHER INFORMATION: Plasmid

<400> SEQUENCE: 1

```
gtgtaggctg gagctgcttc gaagttccta tactttctag agaataggaa cttcggaata    60
ggaacttatg agctcagcca atcgactggc gagcggcatc gcattcttcg catcccgcct   120
ctggcggatg caggaagatc aacggatctc ggcccagttg acccagggct gtcgccacaa   180
tgtcgcggga gcggatcaac cgagcaaagg catgaccgac tggaccttcc ttctgaaggc   240
tcttctcctt gagccacctg tccgccaagg caaagcgctc acagcagtgg tcattctcga   300
gataatcgac gcgtaccaac ttgccatcct gaagaatggt gcagtgtctc ggcaccccat   360
```

```
agggaacctt tgccatcaac tcggcaagat gcagcgtcgt gttggcatcg tgtcccacgc    420
cgaggagaag tacctgccca tcgagttcat ggacacgggc gaccgggctt gcaggcgagt    480
gaggtggcag gggcaatgga tcagagatga tctgctctgc ctgtggcccc gctgccgcaa    540
aggcaaatgg atgggcgctg cgctttacat ttggcaggcg ccagaatgtg tcagagacaa    600
ctccaaggtc cggtgtaacg ggcgacgtgg caggatcgaa cggctcgtcg tccagacctg    660
accacgaggg catgacgagc gtccctcccg gacccagcgc agcacgcagg gcctcgatca    720
gtccaagtgg cccatcttcg aggggccgga cgctacggaa ggagctgtgg accagcagca    780
caccgccggg ggtaacccca aggttgagaa gctgaccgat gagctcggct tttcgccatt    840
cgtattgcac gacattgcac tccaccgctg atgacatcag tcgatcatag cacgatcaac    900
ggcactgttg caaatagtcg gtggtgataa acttatcatc ccctttttgct gatggagctg    960 cacatgaacc cattcaaagg ccggcatttt cagcgtgaca tcattctgtg ggccgtacgc   1020
tggtactgca atacggcat cagttaccgt gagctgcatt ttccgctgca taaccctgct   1080
tcggggtcat tatagcgatt ttttcggtat atccatcctt tttcgcacga tatacaggat   1140
tttgccaaag ggttcgtgta gactttcctt ggtgtatcca acggcgtcag ccgggcagga   1200
taggtgaagt aggcccaccc gcgagcgggt gttccttctt cactgtccct tattcgcacc   1260
tggcggtgct caacgggaat cctgctctgc gaggctggcg ggaacttcga agttcctata   1320 cttttctagag aataggaact cgaactgca ggtcgacgga tccccggaat atcaagctta   1380
tcgataccgt cgacctcgag ggggggcccg gtacccaatt cgccctatag tgagtcgtat   1440
tacaattcac tggccgtcgt tttacaacgt cgtgactggg aaaaccctgg cgttacccaa   1500
cttaatcgcc ttgcagcaca tccccctttc gccagctggc gtaatagcga agaggcccgc   1560
accgatcgcc cttcccaaca gttgcgcagc ctgaatggcg aatggcgcga cgcgccctgt   1620
agcggcgcat taagcgcggc gggtgtggtg gttacgcgca gcgtgaccgc tacacttgcc   1680
agcgccctag cgcccgctcc tttcgctttc ttcccttcct ttctcgccac gttcgccggc   1740
tttccccgtc aagctctaaa tcggggctc cctttagggt tccgatttag tgctttacgg   1800
cacctcgacc ccaaaaaact tgattagggt gatggttcac gtagtgggcc atcgccctga   1860
tagacggttt ttcgcccttt gacgttggag tccacgttct ttaatagtgg actcttgttc   1920
caaactggaa caacactcaa ccctatctcg gtctattctt ttgatttata agggattttg   1980
ccgatttcgg cctattggtt aaaaaatgag ctgatttaac aaaaatttaa cgcgaatttt   2040
aacaaaatat taacgtttac aatttcccag gtggcacttt tcggggaaat gtgcgcggaa   2100
cccctatttg tttattttc taaatacatt caaatatgta tccgctcatg agacaataac   2160
cctgataaat gcttcaataa tattgaaaaa ggaagagtat gagtattcaa catttccgtg   2220
tcgcccttat tccctttttt gcggcatttt gccttcctgt ttttgctcac ccagaaacgc   2280
tggtgaaagt aaaagatgct gaagatcagt tgggtgcacg agtgggttac atcgaactgg   2340
atctcaacag cggtaagatc cttgagagtt ttcgccccga agaacgtttt ccaatgatga   2400
gcacttttaa agttctgcta tgtggcgcgg tattatcccg tattgacgcc gggcaagagc   2460
aactcggtcg ccgcatacac tattctcaga atgacttggt tgagtactca ccagtcacag   2520
aaaagcatct tacggatggc atgacagtaa gagaattatg cagtgctgcc ataaccatga   2580
gtgataacac tgcggccaac ttacttctga caacgatcgg aggaccgaag gagctaaccg   2640
cttttttgca caacatgggg gatcatgtaa ctcgccttga tcgttgggaa ccggagctga   2700
```

-continued

| | |
|---|---|
| atgaagccat accaaacgac gagcgtgaca ccacgatgcc tgtagcaatg caacaacgt | 2760 |
| tgcgcaaact attaactggc gaactactta ctctagcttc ccggcaacaa ttaatagact | 2820 |
| ggatggaggc ggataaagtt gcaggaccac ttctgcgctc ggcccttccg gctggctggt | 2880 |
| ttattgctga taaatctgga gccggtgagc gtgggtctcg cggtatcatt gcagcactgg | 2940 |
| ggccagatgg taagccctcc cgtatcgtag ttatctacac gacggggagt caggcaacta | 3000 |
| tggatgaacg aaatagacag atcgctgaga taggtgcctc actgattaag cattggtaac | 3060 |
| tgtcagacca agtttactca tatatacttt agattgattt aaaacttcat ttttaattta | 3120 |
| aaaggatcta ggtgaagatc cttttttgata atctcatgac caaatccct taacgtgagt | 3180 |
| tttcgttcca ctgagcgtca gaccccgtag aaaagatcaa aggatcttct tgagatcctt | 3240 |
| tttttctgcg cgtaatctgc tgcttgcaaa caaaaaaacc accgctacca gcggtggttt | 3300 |
| gtttgccgga tcaagagcta ccaactcttt ttccgaaggt aactggcttc agcagagcgc | 3360 |
| agataccaaa tactgtcctt ctagtgtagc cgtagttagg ccaccacttc aagaactctg | 3420 |
| tagcaccgcc tacatacctc gctctgctaa tcctgttacc agtggctgct gccagtggcg | 3480 |
| ataagtcgtg tcttaccggg ttggactcaa gacgatagtt accggataag gcgcagcggt | 3540 |
| cgggctgaac gggggggttcg tgcacacagc ccagcttgga gcgaacgacc tacaccgaac | 3600 |
| tgagatacct acagcgtgag ctatgagaaa gcgccacgct tcccgaaggg agaaaggcgg | 3660 |
| acaggtatcc ggtaagcggc agggtcggaa caggagagcg cacgagggag cttccagggg | 3720 |
| gaaacgcctg gtatctttat agtcctgtcg ggtttcgcca cctctgactt gagcgtcgat | 3780 |
| ttttgtgatg ctcgtcaggg gggcggagcc tatggaaaaa cgccagcaac gcggcctttt | 3840 |
| tacggttcct ggccttttgc tggccttttg ctcacatgtt ctttcctgcg ttatcccctg | 3900 |
| attctgtgga taaccgtatt accgcctttg agtgagctga taccgctcgc cgcagccgaa | 3960 |
| cgaccgagcg cagcgagtca gtgagcgagg aagcggaaga gcgcccaata cgcaaaccgc | 4020 |
| ctctccccgc gcgttggccg attcattaat gcagctggca cgacaggttt cccgactgga | 4080 |
| aagcgggcag tgagcgcaac gcaattaatg tgagttagct cactcattag gcaccccagg | 4140 |
| ctttacactt tatgcttccg gctcgtatgt tgtgtggaat tgtgagcgga taacaatttc | 4200 |
| acacaggaaa cagctatgac catgattacg ccaagctcgg aattaaccct cactaaaggg | 4260 |
| aacaaaagct ggagctccac cgcggtggcg gccgctctag aactagtgga tcccccgggc | 4320 |
| tgcaggaatt cgat | 4334 |

<210> SEQ ID NO 2
<211> LENGTH: 7220
<212> TYPE: DNA
<213> ORGANISM: Artificial
<220> FEATURE:
<223> OTHER INFORMATION: Plasmid

<400> SEQUENCE: 2

| | |
|---|---|
| catcgattta ttatgacaac ttgacggcta catcattcac ttttcttca caaccggcac | 60 |
| ggaactcgct cgggctggcc ccggtgcatt ttttaaatac ccgcgagaaa tagagttgat | 120 |
| cgtcaaaacc aacattgcga ccgacggtgg cgataggcat ccgggtggtg ctcaaaagca | 180 |
| gcttcgcctg gctgatacgt tggtcctcgc gccagcttaa gacgctaatc cctaactgct | 240 |
| ggcggaaaag atgtgacaga cgcgacggcg acaagcaaac atgctgtgcg acgctggcga | 300 |
| tatcaaaatt gctgtctgcc aggtgatcgc tgatgtactg acaagcctcg cgtacccgat | 360 |
| tatccatcgg tggatggagc gactcgttaa tcgcttccat gcgccgcagt aacaattgct | 420 |

```
caagcagatt tatcgccagc agctccgaat agcgcccttc cccttgcccg gcgttaatga    480
tttgcccaaa caggtcgctg aaatgcggct ggtgcgcttc atccgggcga aagaaccccg    540
tattggcaaa tattgacggc cagttaagcc attcatgcca gtaggcgcgc ggacgaaagt    600
aaacccactg gtgataccat tcgcgagcct ccgatgacg accgtagtga tgaatctctc     660
ctggcgggaa cagcaaaata tcacccggtc ggcaaacaaa ttctcgtccc tgattttca     720 ccaccccctg accgcgaatg gtgagattga gaatataacc tttcattccc agcggtcggt    780
cgataaaaaa atcgagataa ccgttggcct caatcggcgt taaacccgcc accagatggg    840
cattaaacga gtatcccggc agcaggggat cattttgcgc ttcagccata cttttcatac    900
tcccgccatt cagagaagaa accaattgtc catattgcat cagacattgc cgtcactgcg    960
tcttttactg gctcttctcg ctaaccaaac cggtaacccc gcttattaaa agcattctgt   1020
aacaaagcgg gaccaaagcc atgacaaaaa cgcgtaacaa aagtgtctat aatcacggca   1080
gaaaagtcca cattgattat ttgcacggcg tcacactttg ctatgccata gcatttttat   1140
ccataagatt agcggatcct acctgacgct ttttatcgca actctctact gtttctccat   1200
acccgttttt ttgggaattc gagctctaag gaggttataa aaaatggata ttaatactga   1260
aactgagatc aagcaaaagc attcactaac cccctttcct gttttcctaa tcagcccggc   1320
atttcgcggg cgatattttc acagctattt caggagttca gccatgaacg cttattacat   1380
tcaggatcgt cttgaggctc agagctgggc gcgtcactac cagcagctcg cccgtgaaga   1440
gaaagaggca gaactggcag acgacatgga aaaaggcctg ccccagcacc tgtttgaatc   1500
gctatgcatc gatcatttgc aacgccacgg ggccagcaaa aaatccatta cccgtgcgtt   1560
tgatgacgat gttgagtttc aggagcgcat ggcagaacac atccggtaca tggttgaaac   1620
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacggcattt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacggggcc gtggcagtcg   2100
catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acaggggat gatgcgtggc    2520 acaaattacg gctcggcgtc atcaccgctt cagaagttca aacgtgata gcaaaccccc    2580 gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
```

```
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaatggac gaggcactgg ctgaaattgg ttttgtattt ggggagcaat    3120
ggcgatgata agctagctta aaaaagcaaa agggccgcag atgcgaccct tgtgtatcaa    3180
acaagacgat taaaaatctt cgttagtttc tgctacgcct tcgctatcat ctacagagaa    3240
atccggcgtt gagttcgggt tgctcagcag caactcacgt actttcttct cgatctcttt    3300
cgcggtttcc gggttatctt tcagccaggc agtcgcattc gctttaccct gaccgatctt    3360
ctcacctttg tagctgtacc acgcgcctgc tttctcgatc agcttctctt ttacgcccag    3420
gtcaaccagt tcgccgtaga agttgatacc ttcgccgtag aggatctgga attcagcctg    3480
tttaaacggc gcagcgattt tgttcttcac cactttcacg cgggtttcgc tacccaccac    3540
gttttcgccc tctttcaccg cgccgatacg acggatgtcg agacgaacag aggcgtagaa    3600
tttcagcgcg ttaccaccgg tagtggtttc gggttaccg aacatcacac caattttcat    3660
acggatctgg ttgatgaaga tcagcagcgt gttggactgc ttcaggttac ccgccagctt    3720
acgcatcgcc tggctcatca tacgtgccgc aaggcccatg tgagagtcgc cgatttcgcc    3780
ttcgatttcc gctttcggcg tcagtgccgc cacggagtca acgacgataa cgtctactgc    3840
gccagaacgc gccagggcgt cacagatttc cagtgcctgc tcgccggtgt ccggctggga    3900
gcacagcagg ttgtcgatat cgacgcccag tttacgtgcg tagattgggt ccagcgcgtg    3960
ttcagcatcg ataaacgcac aggttttacc ttcacgctgc gctgcggcga tcacctgcag    4020
cgtcagcgtg gttttaccgg aagattccgg tccgtagatt tcgacgatac ggcccatcgg    4080
cagaccacct gccccaagcg cgatatccag tgaaagcgaa ccggtagaga tggtttccac    4140
atccatggaa cggtcttcac ccaggcgcat gatggagcct ttaccaaatt gtttctcaat    4200
ctggcccagt gctgccgcca acgctttctg tttgttttcg tcgatagcca tttttactcc    4260
tgtcatgcct agcccatggg tatggacagt tttcccttg atatgtaacg gtgaacagtt    4320
gttctacttt tgtttgttag tcttgatgct tcactgatag atacaagagc cataagaacc    4380
tcagatcctt ccgtatttag ccagtatgtt ctctagtgtg gttcgttgtt tttgcgtgag    4440
ccatgagaac gaaccattga gatcatactt actttgcatg tcactcaaaa attttgcctc    4500
aaaactggtg agctgaattt ttgcagttaa agcatcgtgt agtgtttttc ttagtccgtt    4560
acgtaggtag gaatctgatg taatggttgt tggtattttg tcaccattca ttttatctg    4620
gttgttctca agttcggtta cgagatccat ttgtctatct agttcaactt ggaaaatcaa    4680
cgtatcagtc gggcggcctc gcttatcaac caccaatttc atattgctgt aagtgtttaa    4740
atctttactt attggtttca aaacccattg gttaagcctt ttaaactcat ggtagttatt    4800
ttcaagcatt aacatgaact taaattcatc aaggctaatc tctatatttg ccttgtgagt    4860
tttcttttgt gttagttctt ttaataacca ctcataaatc ctcatagagt atttgttttc    4920
aaaagactta acatgttcca gattatattt tatgaatttt tttaactgga aagataagg    4980
caatatctct tcactaaaaa ctaattctaa ttttcgctt gagaacttgg catagttttgt    5040
ccactggaaa atctcaaagc ctttaaccaa aggattcctg atttccacag ttctcgtcat    5100
cagctctctg gttgctttag ctaatacacc ataagcattt tccctactga tgttcatcat    5160
```

-continued

```
ctgagcgtat tggttataag tgaacgatac cgtccgttct ttccttgtag ggttttcaat    5220 cgtgggggttg agtagtgcca cacagcataa aattagcttg gtttcatgct ccgttaagtc    5280
atagcgacta atcgctagtt catttgcttt gaaaacaact aattcagaca tacatctcaa    5340
ttggtctagg tgattttaat cactatacca attgagatgg gctagtcaat gataattact    5400
agtccttttc ctttgagttg tgggtatctg taaattctgc tagacctttg ctggaaaact    5460
tgtaaattct gctagaccct ctgtaaattc cgctagacct ttgtgtgttt ttttgttta    5520 tattcaagtg gttataattt atagaataaa gaagaataa aaaagataa aagaataga    5580 tcccagccct gtgtataact cactacttta gtcagttccg cagtattaca aaggatgtc    5640 gcaaacgctg tttgctcctc tacaaaacag accttaaaac cctaaaggct taagtagcac    5700
cctcgcaagc tcggttgcgg ccgcaatcgg gcaaatcgct gaatattcct tttgtctccg    5760
accatcaggc acctgagtcg ctgtcttttt cgtgacattc agttcgctgc gctcacggct    5820
ctggcagtga atggggggtaa atggcactac aggcgccttt tatggattca tgcaaggaaa    5880
ctacccataa tacaagaaaa gcccgtcacg ggcttctcag ggcgttttat ggcgggtctg    5940
ctatgtggtg ctatctgact ttttgctgtt cagcagttcc tgccctctga ttttccagtc    6000
tgaccacttc ggattatccc gtgacaggtc attcagactg gctaatgcac ccagtaaggc    6060
agcggtatca tcaacgggggt ctgacgctca gtggaacgaa aactcacgtt aagggatttt    6120
ggtcatgaga ttatcaaaaa ggatcttcac ctagatcctt ttaaattaaa aatgaagttt    6180
taaatcaatc taaagtatat atgagtaaac ttggtctgac agttaccaat gcttaatcag    6240
tgaggcacct atctcagcga ttaagggcac caataactgc cttaaaaaa ttacgccccg    6300 ccctgccact catcgcagta ctgttgtaat tcattaagca ttctgccgac atggaagcca    6360
tcacagacgg catgatgaac ctgaatcgcc agcggcatca gcaccttgtc gccttgcgta    6420
taatatttgc ccatggtgaa aacgggggcg aagaagttgt ccatattggc cacgtttaaa    6480
tcaaaactgg tgaaactcac ccagggattg gctgagacga aaaacatatt ctcaataaac    6540
cctttaggga ataggccag gttttcaccg taacacgcca catcttgcga atatatgtgt    6600
agaaactgcc ggaaatcgtc gtggtattca ctccagagcg atgaaaacgt ttcagtttgc    6660
tcatggaaaa cggtgtaaca agggtgaaca ctatcccata tcaccagctc accgtctttc    6720
attgccatac ggaattccgg atgagcattc atcaggcggg caagaatgtg aataaaggcc    6780
ggataaaact tgtgcttatt tttctttacg gtctttaaaa aggccgtaat atccagctga    6840
acggtctggt tataggtaca ttgagcaact gactgaaatg cctcaaaatg ttctttacga    6900
tgccattggg atatatcaac ggtggtatat ccagtgattt ttttctccat tttagcttcc    6960
ttagctcctg aaaatctcga taactcaaaa aatacgcccg gtagtgatct tatttcatta    7020
tggtgaaagt tggaacctct tacgtgccga aagggaata agggcgacac ggaaatgttg    7080
aatactcata ctcttccttt ttcaatatta ttgaagcatt tatcagggtt attgtctcat    7140
gagcggatac atatttgaat gtatttagaa aaataaacaa atagggggttc cgcgcacatt    7200 tccccgaaaa gtgccacctg                                                 7220
```

<210> SEQ ID NO 3
<211> LENGTH: 59
<212> TYPE: DNA
<213> ORGANISM: Artificial
<220> FEATURE:
<223> OTHER INFORMATION: PCR Primer

<400> SEQUENCE: 3
gtgtttaatt ctgacaacct gagactcgac ggaaaaatga ttccggggat ccgtcgacc        59

<210> SEQ ID NO 4
<211> LENGTH: 58
<212> TYPE: DNA
<213> ORGANISM: Artificial
<220> FEATURE:
<223> OTHER INFORMATION: PCR Primer

<400> SEQUENCE: 4
ttaattgagc tcctgtaccc caccaccgga gacggtttat gtaggctgga gctgcttc         58

<210> SEQ ID NO 5
<211> LENGTH: 33
<212> TYPE: DNA
<213> ORGANISM: Artificial
<220> FEATURE:
<223> OTHER INFORMATION: PCR Primer

<400> SEQUENCE: 5
ggtattccat atgatctttg acggaaaggt cgc                                    33

<210> SEQ ID NO 6
<211> LENGTH: 24
<212> TYPE: DNA
<213> ORGANISM: Artificial
<220> FEATURE:
<223> OTHER INFORMATION: PCR Primer

<400> SEQUENCE: 6
cgggatccct aggggcgctg accc                                              24

<210> SEQ ID NO 7
<211> LENGTH: 56
<212> TYPE: DNA
<213> ORGANISM: Artificial
<220> FEATURE:
<223> OTHER INFORMATION: PCR Primer

<400> SEQUENCE: 7
gtttaacttt aagaaggaga tataccatga tctttgacgg aaaggtcgca atcatt           56

<210> SEQ ID NO 8
<211> LENGTH: 56
<212> TYPE: DNA
<213> ORGANISM: Artificial
<220> FEATURE:
<223> OTHER INFORMATION: PCR Primer

<400> SEQUENCE: 8
aatgattgcg acctttccgt caaagatcat ggtatatctc cttcttaaag ttaaac           56

<210> SEQ ID NO 9
<211> LENGTH: 768
<212> TYPE: DNA
<213> ORGANISM: Escherichia coli
<220> FEATURE:
<221> NAME/KEY: CDS
<222> LOCATION: (1)..(768)

<400> SEQUENCE: 9 gtg ttt aat tct gac aac ctg aga ctc gac gga aaa tgc gcc atc atc        48
Val Phe Asn Ser Asp Asn Leu Arg Leu Asp Gly Lys Cys Ala Ile Ile
1               5                   10                  15

```
aca ggt gcg ggt gca ggt att ggt aaa gaa atc gcc att aca ttc gcg      96
Thr Gly Ala Gly Ala Gly Ile Gly Lys Glu Ile Ala Ile Thr Phe Ala
         20                  25                  30 aca gct ggc gca tct gtg gtg gtc agt gat att aac gcc gac gca gct     144
Thr Ala Gly Ala Ser Val Val Val Ser Asp Ile Asn Ala Asp Ala Ala
     35                  40                  45 aac cat gtt gta gac gaa att caa caa ctg ggt ggt cag gca ttt gcc     192
Asn His Val Val Asp Glu Ile Gln Gln Leu Gly Gly Gln Ala Phe Ala
 50                  55                  60 tgc cgt tgt gat att act tcc gaa cag gaa ctc tct gca ctg gca gac     240
Cys Arg Cys Asp Ile Thr Ser Glu Gln Glu Leu Ser Ala Leu Ala Asp
 65                  70                  75                  80 ttt gct atc agt aag ctg ggt aaa gtt gat att ctg gtt aac aac gcc     288
Phe Ala Ile Ser Lys Leu Gly Lys Val Asp Ile Leu Val Asn Asn Ala
                 85                  90                  95 ggt ggc ggt gga cct aaa ccg ttt gat atg cca atg gcg gat ttt cgc     336
Gly Gly Gly Gly Pro Lys Pro Phe Asp Met Pro Met Ala Asp Phe Arg
            100                 105                 110 cgt gct tat gaa ctg aat gtg ttt tct ttt ttc cat ctg tca caa ctt     384
Arg Ala Tyr Glu Leu Asn Val Phe Ser Phe Phe His Leu Ser Gln Leu
        115                 120                 125 gtt gcg cca gaa atg gaa aaa aat ggc ggt ggc gtt att ctg acc atc     432
Val Ala Pro Glu Met Glu Lys Asn Gly Gly Gly Val Ile Leu Thr Ile
130                 135                 140 act tct atg gcg gca gaa aat aaa aat ata aac atg act tcc tat gca     480
Thr Ser Met Ala Ala Glu Asn Lys Asn Ile Asn Met Thr Ser Tyr Ala
145                 150                 155                 160 tca tct aaa gct gcg gcc agt cat ctg gtc aga aat atg gcg ttt gac     528
Ser Ser Lys Ala Ala Ala Ser His Leu Val Arg Asn Met Ala Phe Asp
                165                 170                 175 cta ggt gaa aaa aat att cgg gta aat ggc att gcg ccg ggg gca ata     576
Leu Gly Glu Lys Asn Ile Arg Val Asn Gly Ile Ala Pro Gly Ala Ile
            180                 185                 190 tta acc gat gcc ctg aaa tcc gtt att aca cca gaa att gaa caa aaa     624
Leu Thr Asp Ala Leu Lys Ser Val Ile Thr Pro Glu Ile Glu Gln Lys
        195                 200                 205 atg tta cag cac acg ccg atc aga cgt ctg ggc caa ccg caa gat att     672
Met Leu Gln His Thr Pro Ile Arg Arg Leu Gly Gln Pro Gln Asp Ile
    210                 215                 220 gct aac gca gcg ctg ttc ctt tgc tcg cct gct gcg agc tgg gta agc     720
Ala Asn Ala Ala Leu Phe Leu Cys Ser Pro Ala Ala Ser Trp Val Ser
225                 230                 235                 240 gga caa att ctc acc gtc tcc ggt ggt ggg gta cag gag ctc aat taa     768
Gly Gln Ile Leu Thr Val Ser Gly Gly Gly Val Gln Glu Leu Asn
                245                 250                 255

<210> SEQ ID NO 10
<211> LENGTH: 255
<212> TYPE: PRT
<213> ORGANISM: Escherichia coli

<400> SEQUENCE: 10

Val Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
            20                  25                  30

Thr Ala Gly Ala Ser Val Val Val Ser Asp Ile Asn Ala Asp Ala Ala
        35                  40                  45

Asn His Val Val Asp Glu Ile Gln Gln Leu Gly Gly Gln Ala Phe Ala
    50                  55                  60
```

```
Cys Arg Cys Asp Ile Thr Ser Glu Gln Glu Leu Ser Ala Leu Ala Asp
 65                  70                  75                  80

Phe Ala Ile Ser Lys Leu Gly Lys Val Asp Ile Leu Val Asn Asn Ala
                 85                  90                  95

Gly Gly Gly Gly Pro Lys Pro Phe Asp Met Pro Met Ala Asp Phe Arg
            100                 105                 110

Arg Ala Tyr Glu Leu Asn Val Phe Ser Phe Phe His Leu Ser Gln Leu
            115                 120                 125

Val Ala Pro Glu Met Glu Lys Asn Gly Gly Val Ile Leu Thr Ile
    130                 135                 140

Thr Ser Met Ala Ala Glu Asn Lys Asn Ile Asn Met Thr Ser Tyr Ala
145                 150                 155                 160

Ser Ser Lys Ala Ala Ser His Leu Val Arg Asn Met Ala Phe Asp
                165                 170                 175

Leu Gly Glu Lys Asn Ile Arg Val Asn Gly Ile Ala Pro Gly Ala Ile
            180                 185                 190

Leu Thr Asp Ala Leu Lys Ser Val Ile Thr Pro Glu Ile Glu Gln Lys
            195                 200                 205

Met Leu Gln His Thr Pro Ile Arg Arg Leu Gly Gln Pro Gln Asp Ile
    210                 215                 220

Ala Asn Ala Ala Leu Phe Leu Cys Ser Pro Ala Ala Ser Trp Val Ser
225                 230                 235                 240

Gly Gln Ile Leu Thr Val Ser Gly Gly Gly Val Gln Glu Leu Asn
                245                 250                 255

<210> SEQ ID NO 11
<211> LENGTH: 813
<212> TYPE: DNA
<213> ORGANISM: Clostridium sp.
<220> FEATURE:
<221> NAME/KEY: CDS
<222> LOCATION: (1)..(813)

<400> SEQUENCE: 11 atg gat ttt att gat ttt aag gag atg ggc aga atg ggg atc ttt gac    48
Met Asp Phe Ile Asp Phe Lys Glu Met Gly Arg Met Gly Ile Phe Asp
1               5                  10                  15 gga aag gtc gca atc att act ggc ggg ggc aag gcc aaa tcg atc ggc    96
Gly Lys Val Ala Ile Ile Thr Gly Gly Gly Lys Ala Lys Ser Ile Gly
                20                  25                  30 tac ggc att gcc gtg gcc tat gct aag gag ggg gcc aac ctg gtc ctg   144
Tyr Gly Ile Ala Val Ala Tyr Ala Lys Glu Gly Ala Asn Leu Val Leu
            35                  40                  45 acc ggc aga aac gag cag aaa ctg ctg gac gcc aag gag gag ctg gag   192
Thr Gly Arg Asn Glu Gln Lys Leu Leu Asp Ala Lys Glu Glu Leu Glu
        50                  55                  60 cgc ctc tac ggc atc aag gtg ttg ccg ctg gcg gtg gac gtc acc ccc   240
Arg Leu Tyr Gly Ile Lys Val Leu Pro Leu Ala Val Asp Val Thr Pro
65                  70                  75                  80 agc gat gag tcg gag gac cgg gtc aag gaa gcc gtg cag aag gtc atc   288
Ser Asp Glu Ser Glu Asp Arg Val Lys Glu Ala Val Gln Lys Val Ile
                85                  90                  95 gcc gaa ttc ggc cgc atc gac gtg ctg atc aac aac gcc cag gcg tcg   336
Ala Glu Phe Gly Arg Ile Asp Val Leu Ile Asn Asn Ala Gln Ala Ser
            100                 105                 110 gcc tcg ggc atc ccc ctg tcc atg cag acc aaa gac cac ttt gac ctg   384
Ala Ser Gly Ile Pro Leu Ser Met Gln Thr Lys Asp His Phe Asp Leu
        115                 120                 125
```

| | | | | | | | | | | | | | | | | |
|---|---|---|---|---|---|---|---|---|---|---|---|---|---|---|---|---|
| ggc | atc | tac | tcc | ggg | ctc | tac | gcc | acc | ttc | tac | tac | atg | agg | gag | tgc | 432 |
| Gly | Ile | Tyr | Ser | Gly | Leu | Tyr | Ala | Thr | Phe | Tyr | Tyr | Met | Arg | Glu | Cys | |
| | 130 | | | | 135 | | | | | 140 | | | | | | |
| tat | ccc | tac | ctg | aag | gag | acc | cag | ggc | tcg | gtc | atc | aac | ttc | gcc | tcc | 480 |
| Tyr | Pro | Tyr | Leu | Lys | Glu | Thr | Gln | Gly | Ser | Val | Ile | Asn | Phe | Ala | Ser | |
| 145 | | | | | 150 | | | | | 155 | | | | | 160 | |
| ggc | gcc | ggc | ctc | ttc | ggc | aac | gtg | ggt | cag | tgc | tcc | tac | gcc | gcc | gcc | 528 |
| Gly | Ala | Gly | Leu | Phe | Gly | Asn | Val | Gly | Gln | Cys | Ser | Tyr | Ala | Ala | Ala | |
| | | | | 165 | | | | | 170 | | | | | 175 | | |
| aaa | gag | ggc | atc | cgc | ggc | ctc | tcc | cgc | gtc | gcg | gcc | acc | gag | tgg | ggc | 576 |
| Lys | Glu | Gly | Ile | Arg | Gly | Leu | Ser | Arg | Val | Ala | Ala | Thr | Glu | Trp | Gly | |
| | | 180 | | | | | 185 | | | | | 190 | | | | |
| aag | gac | aac | atc | aac | gtc | aac | gtg | gtc | tgc | ccc | ctg | gcc | atg | acc | gcc | 624 |
| Lys | Asp | Asn | Ile | Asn | Val | Asn | Val | Val | Cys | Pro | Leu | Ala | Met | Thr | Ala | |
| | | | 195 | | | | | 200 | | | | | 205 | | | |
| cag | ctg | gag | aac | ttc | aag | ctc | tcc | tac | cct | gag | gcc | tac | gag | aaa | aac | 672 |
| Gln | Leu | Glu | Asn | Phe | Lys | Leu | Ser | Tyr | Pro | Glu | Ala | Tyr | Glu | Lys | Asn | |
| | 210 | | | | | 215 | | | | | 220 | | | | | |
| ctc | aga | ggg | gtg | ccc | atg | ggc | cgc | ttc | ggt | gac | ccc | gag | ctg | gac | atc | 720 |
| Leu | Arg | Gly | Val | Pro | Met | Gly | Arg | Phe | Gly | Asp | Pro | Glu | Leu | Asp | Ile | |
| 225 | | | | | 230 | | | | | 235 | | | | | 240 | |
| ggc | cgg | gtc | tgc | gtg | cag | ctc | ggc | tcg | ccc | gac | ttc | aag | tac | atg | tcc | 768 |
| Gly | Arg | Val | Cys | Val | Gln | Leu | Gly | Ser | Pro | Asp | Phe | Lys | Tyr | Met | Ser | |
| | | | | 245 | | | | | 250 | | | | | 255 | | |
| ggc | gag | acc | ctc | acc | ctg | gaa | ggc | ggc | atg | ggt | cag | cgc | ccc | tag | | 813 |
| Gly | Glu | Thr | Leu | Thr | Leu | Glu | Gly | Gly | Met | Gly | Gln | Arg | Pro | | | |
| | | 260 | | | | | 265 | | | | | 270 | | | | |

<210> SEQ ID NO 12
<211> LENGTH: 270
<212> TYPE: PRT
<213> ORGANISM: Clostridium sp.

<400> SEQUENCE: 12

Met Asp Phe Ile Asp Phe Lys Glu Met Gly Arg Met Gly Ile Phe Asp
1               5                   10                  15

Gly Lys Val Ala Ile Ile Thr Gly Gly Gly Lys

```
                180                   185                   190
Lys Asp Asn Ile Asn Val Asn Val Val Cys Pro Leu Ala Met Thr Ala
            195                   200                   205

Gln Leu Glu Asn Phe Lys Leu Ser Tyr Pro Glu Ala Tyr Glu Lys Asn
        210                   215                   220

Leu Arg Gly Val Pro Met Gly Arg Phe Gly Asp Pro Glu Leu Asp Ile
225                   230                   235                   240

Gly Arg Val Cys Val Gln Leu Gly Ser Pro Asp Phe Lys Tyr Met Ser
                245                   250                   255

Gly Glu Thr Leu Thr Leu Glu Gly Gly Met Gly Gln Arg Pro
            260                   265                   270

<210> SEQ ID NO 13
<211> LENGTH: 774
<212> TYPE: DNA
<213> ORGANISM: Clostridium sp.
<220> FEATURE:
<221> NAME/KEY: CDS
<222> LOCATION: (1)..(774)

<400> SEQUENCE: 13 atc ttt gac gga aag gtc gca atc att act ggc ggg ggc aag gcc aaa      48
Ile Phe Asp Gly Lys Val Ala Ile Ile Thr Gly Gly Gly Lys Ala Lys
1               5                   10                  15 tcg atc ggc tac ggc att gcc gtg gcc tat gct aag gag ggg gcc aac      96
Ser Ile Gly Tyr Gly Ile Ala Val Ala Tyr Ala Lys Glu Gly Ala Asn
                20                  25                  30 ctg gtc ctg acc ggc aga aac gag cag aaa ctg ctg gac gcc aag gag     144
Leu Val Leu Thr Gly Arg Asn Glu Gln Lys Leu Leu Asp Ala Lys Glu
            35                  40                  45 gag ctg gag cgc ctc tac ggc atc aag gtg ttg ccg ctg gcg gtg gac     192
Glu Leu Glu Arg Leu Tyr Gly Ile Lys Val Leu Pro Leu Ala Val Asp
        50                  55                  60 gtc acc ccc agc gat gag tcg gag gac cgg gtc aag gaa gcc gtg cag     240
Val Thr Pro Ser Asp Glu Ser Glu Asp Arg Val Lys Glu Ala Val Gln
65                  70                  75                  80 aag gtc atc gcc gaa ttc ggc cgc atc gac gtg ctg atc aac aac gcc     288
Lys Val Ile Ala Glu Phe Gly Arg Ile Asp Val Leu Ile Asn Asn Ala
                85                  90                  95 cag gcg tcg gcc tcg ggc atc ccc ctg tcc atg cag acc aaa gac cac     336
Gln Ala Ser Ala Ser Gly Ile Pro Leu Ser Met Gln Thr Lys Asp His
            100                 105                 110 ttt gac ctg ggc atc tac tcc ggg ctc tac gcc acc ttc tac tac atg     384
Phe Asp Leu Gly Ile Tyr Ser Gly Leu Tyr Ala Thr Phe Tyr Tyr Met
        115                 120                 125 agg gag tgc tat ccc tac ctg aag gag acc cag ggc tcg gtc atc aac     432
Arg Glu Cys Tyr Pro Tyr Leu Lys Glu Thr Gln Gly Ser Val Ile Asn
130                 135                 140 ttc gcc tcc ggc gcc ggc ctc ttc ggc aac gtg ggt cag tgc tcc tac     480
Phe Ala Ser Gly Ala Gly Leu Phe Gly Asn Val Gly Gln Cys Ser Tyr
145                 150                 155                 160 gcc gcc gcc aaa gag ggc atc cgc ggc ctc tcc cgc gtc gcg gcc acc     528
Ala Ala Ala Lys Glu Gly Ile Arg Gly Leu Ser Arg Val Ala Ala Thr
                165                 170                 175 gag tgg ggc aag gac aac atc aac gtc aac gtg gtc tgc ccc ctg gcc     576
Glu Trp Gly Lys Asp Asn Ile Asn Val Asn Val Val Cys Pro Leu Ala
            180                 185                 190 atg acc gcc cag ctg gag aac ttc aag ctc tcc tac cct gag gcc tac     624
Met Thr Ala Gln Leu Glu Asn Phe Lys Leu Ser Tyr Pro Glu Ala Tyr
        195                 200                 205
```

```
gag aaa aac ctc aga ggg gtg ccc atg ggc cgc ttc ggt gac ccc gag      672
Glu Lys Asn Leu Arg Gly Val Pro Met Gly Arg Phe Gly Asp Pro Glu
    210                 215                 220 ctg gac atc ggc cgg gtc tgc gtg cag ctc ggc tcg ccc gac ttc aag      720
Leu Asp Ile Gly Arg Val Cys Val Gln Leu Gly Ser Pro Asp Phe Lys
225                 230                 235                 240 tac atg tcc ggc gag acc ctc acc ctg gaa ggc ggt atg ggt cag cgc      768
Tyr Met Ser Gly Glu Thr Leu Thr Leu Glu Gly Gly Met Gly Gln Arg
                245                 250                 255 ccc tag                                                              774
Pro
```

<210> SEQ ID NO 14
<211> LENGTH: 257
<212> TYPE: PRT
<213> ORGANISM: Clostridium sp.

<400> SEQUENCE: 14

```
Ile Phe Asp Gly Lys Val Ala Ile Ile Thr Gly Gly Gly Lys Ala Lys
1               5                   10                  15

Ser Ile Gly Tyr Gly Ile Ala Val Ala Tyr Ala Lys Glu Gly Ala Asn
            20                  25                  30

Leu Val Leu Thr Gly Arg Asn Glu Gln Lys Leu Leu Asp Ala Lys Glu
        35                  40                  45

Glu Leu Glu Arg Leu Tyr Gly Ile Lys Val Leu Pro Leu Ala Val Asp
    50                  55                  60

Val Thr Pro Ser Asp Glu Ser Glu Asp Arg Val Lys Glu Ala Val Gln
65                  70                  75                  80

Lys Val Ile Ala Glu Phe Gly Arg Ile Asp Val Leu Ile Asn Asn Ala
                85                  90                  95

Gln Ala Ser Ala Ser Gly Ile Pro Leu Ser Met Gln Thr Lys Asp His
            100                 105                 110

Phe Asp Leu Gly Ile Tyr Ser Gly Leu Tyr Ala Thr Phe Tyr Tyr Met
        115                 120                 125

Arg Glu Cys Tyr Pro Tyr Leu Lys Glu Thr Gln Gly Ser Val Ile Asn
    130                 135                 140

Phe Ala Ser Gly Ala Gly Leu Phe Gly Asn Val Gly Gln Cys Ser Tyr
145                 150                 155                 160

Ala Ala Ala Lys Glu Gly Ile Arg Gly Leu Ser Arg Val Ala Ala Thr
                165                 170                 175

Glu Trp Gly Lys Asp Asn Ile Asn Val Asn Val Val Cys Pro Leu Ala
            180                 185                 190

Met Thr Ala Gln Leu Glu Asn Phe Lys Leu Ser Tyr Pro Glu Ala Tyr
        195                 200                 205

Glu Lys Asn Leu Arg Gly Val Pro Met Gly Arg Phe Gly Asp Pro Glu
    210                 215                 220

Leu Asp Ile Gly Arg Val Cys Val Gln Leu Gly Ser Pro Asp Phe Lys
225                 230                 235                 240

Tyr Met Ser Gly Glu Thr Leu Thr Leu Glu Gly Gly Met Gly Gln Arg
                245                 250                 255

Pro
```

<210> SEQ ID NO 15
<211> LENGTH: 777
<212> TYPE: DNA
<213> ORGANISM: Artificial

<220> FEATURE:
<223> OTHER INFORMATION: Mutant Q97H
<220> FEATURE:
<221> NAME/KEY: CDS
<222> LOCATION: (1)..(777)

<400> SEQUENCE: 15

| | | | | | | | | | | | | | | | | |
|---|---|---|---|---|---|---|---|---|---|---|---|---|---|---|---|---|
| atg | atc | ttt | gac | gga | aag | gtc | gca | atc | att | act | ggc | ggg | ggc | aag | gcc | 48 |
| Met | Ile | Phe | Asp | Gly | Lys | Val | Ala | Ile | Ile | Thr | Gly | Gly | Gly | Lys | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aaa | tcg | atc | ggc | tac | ggc | att | gcc | gtg | gcc | tat | gct | aag | gag | ggg | gcc | 96 |
| Lys | Ser | Ile | Gly | Tyr | Gly | Ile | Ala | Val | Ala | Tyr | Ala | Lys | Glu | Gly | Ala | |
| | | | 20 | | | | 25 | | | | | 30 | | | | |

| | | | | | | | | | | | | | | | | |
|---|---|---|---|---|---|---|---|---|---|---|---|---|---|---|---|---|
| aac | ctg | gtc | ctg | acc | ggc | aga | aac | gag | cag | aaa | ctg | ctg | gac | gcc | aag | 144 |
| Asn | Leu | Val | Leu | Thr | Gly | Arg | Asn | Glu | Gln | Lys | Leu | Leu | Asp | Ala | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| gag | gag | ctg | gag | cgc | ctc | tac | ggc | atc | aag | gtg | ttg | ccg | ctg | gcg | gtg | 192 |
| Glu | Glu | Leu | Glu | Arg | Leu | Tyr | Gly | Ile | Lys | Val | Leu | Pro | Leu | Ala | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| gac | gtc | acc | ccc | agc | gat | gag | tcg | gag | gac | cgg | gtc | aag | gaa | gcc | gtg | 240 |
| Asp | Val | Thr | Pro | Ser | Asp | Glu | Ser | Glu | Asp | Arg | Val | Lys | Glu | Ala | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cag | aag | gtc | atc | gcc | gaa | ttc | ggc | cgc | atc | gac | gtg | ctg | atc | aac | aac | 288 |
| Gln | Lys | Val | Ile | Ala | Glu | Phe | Gly | Arg | Ile | Asp | Val | Leu | Ile | Asn | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| gcc | cat | gcg | tcg | gcc | tcg | ggc | atc | ccc | ctg | tcc | atg | cag | acc | aaa | gac | 336 |
| Ala | His | Ala | Ser | Ala | Ser | Gly | Ile | Pro | Leu | Ser | Met | Gln | Thr | Lys | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| cac | ttt | gac | ctg | ggc | atc | tac | tcc | ggg | ctc | tac | gcc | acc | ttc | tac | tac | 384 |
| His | Phe | Asp | Leu | Gly | Ile | Tyr | Ser | Gly | Leu | Tyr | Ala | Thr | Phe | Tyr | Tyr | |
| | | | | 115 | | | | | 120 | | | | | 125 | | |

| | | | | | | | | | | | | | | | | |
|---|---|---|---|---|---|---|---|---|---|---|---|---|---|---|---|---|
| atg | agg | gag | tgc | tat | ccc | tac | ctg | aag | gag | act | cag | ggc | tcg | gtc | atc | 432 |
| Met | Arg | Glu | Cys | Tyr | Pro | Tyr | Leu | Lys | Glu | Thr | Gln | Gly | Ser | Val | Ile | |
| | | 130 | | | | | 135 | | | | | 140 | | | | |

| | | | | | | | | | | | | | | | | |
|---|---|---|---|---|---|---|---|---|---|---|---|---|---|---|---|---|
| aac | ttc | gcc | tcc | ggc | gcc | ggc | ctc | ttc | ggc | aac | gtg | ggt | cag | tgc | tcc | 480 |
| Asn | Phe | Ala | Ser | Gly | Ala | Gly | Leu | Phe | Gly | Asn | Val | Gly | Gln | Cys | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tac | gcc | gcc | gcc | aaa | gag | ggc | atc | cgc | ggc | ctc | tcc | cgc | gtc | gcg | gcc | 528 |
| Tyr | Ala | Ala | Ala | Lys | Glu | Gly | Ile | Arg | Gly | Leu | Ser | Arg | Val | Ala | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | gag | tgg | ggc | aag | gac | aac | atc | aac | gtc | aac | gtg | gtc | tgc | ccc | ctg | 576 |
| Thr | Glu | Trp | Gly | Lys | Asp | Asn | Ile | Asn | Val | Asn | Val | Val | Cys | Pro | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| gcc | atg | acc | gcc | cag | ctg | gag | aac | ttc | aag | ctc | tcc | tac | cct | gag | gcc | 624 |
| Ala | Met | Thr | Ala | Gln | Leu | Glu | Asn | Phe | Lys | Leu | Ser | Tyr | Pro | Glu | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | gag | aaa | aac | ctc | aga | ggg | gtg | ccc | atg | ggc | cgc | ttc | ggt | gac | ccc | 672 |
| Tyr | Glu | Lys | Asn | Leu | Arg | Gly | Val | Pro | Met | Gly | Arg | Phe | Gly | Asp | Pro | |
| 210 | | | | | 215 | | | | | 220 | | | | | | |

| | | | | | | | | | | | | | | | | |
|---|---|---|---|---|---|---|---|---|---|---|---|---|---|---|---|---|
| gag | ctg | gac | atc | ggc | cgg | gtc | tgc | gtg | cag | ctc | ggc | tcg | ccc | gac | ttc | 720 |
| Glu | Leu | Asp | Ile | Gly | Arg | Val | Cys | Val | Gln | Leu | Gly | Ser | Pro | Asp | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | tac | atg | tcc | ggc | gag | acc | ctc | acc | ctg | gaa | ggc | ggc | atg | ggt | cag | 768 |
| Lys | Tyr | Met | Ser | Gly | Glu | Thr | Leu | Thr | Leu | Glu | Gly | Gly | Met | Gly | Gln | |
| | | | | 245 | | | | | 250 | | | | | 255 | | |

| | | | |
|---|---|---|---|
| cgc | ccc | tag | 777 |
| Arg | Pro | | |

<210> SEQ ID NO 16
<211> LENGTH: 258
<212> TYPE: PRT

<213> ORGANISM: Artificial
<220> FEATURE:
<223> OTHER INFORMATION: Synthetic Construct

<400> SEQUENCE: 16

Met Ile Phe Asp Gly Lys Val Ala Ile Thr Gly Gly Lys Ala
1               5                   10                  15

Lys Ser Ile Gly Tyr Gly Ile Ala Val Ala Tyr Ala Lys Glu Gly Ala
            20                  25                  30

Asn Leu Val Leu Thr Gly Arg Asn Glu Gln Lys Leu Leu Asp Ala Lys
        35                  40                  45

Glu Glu Leu Glu Arg Leu Tyr Gly Ile Lys Val Leu Pro Leu Ala Val
50                  55                  60

Asp Val Thr Pro Ser Asp Glu Ser Asp Arg Val Lys Glu Ala Val
65                  70                  75                  80

Gln Lys Val Ile Ala Glu Phe Gly Arg Ile Asp Val Leu Ile Asn Asn
                85                  90                  95

Ala His Ala Ser Ala Ser Gly Ile Pro Leu Ser Met Gln Thr Lys Asp
            100                 105                 110

His Phe Asp Leu Gly Ile Tyr Ser Gly Leu Tyr Ala Thr Phe Tyr Tyr
        115                 120                 125

Met Arg Glu Cys Tyr Pro Tyr Leu Lys Glu Thr Gln Gly Ser Val Ile
130                 135                 140

Asn Phe Ala Ser Gly Ala Gly Leu Phe Gly Asn Val Gly Gln Cys Ser
145                 150                 155                 160

Tyr Ala Ala Ala Lys Glu Gly Ile Arg Gly Leu Ser Arg Val Ala Ala
                165                 170                 175

Thr Glu Trp Gly Lys Asp Asn Ile Asn Val Asn Val Val Cys Pro Leu
            180                 185                 190

Ala Met Thr Ala Gln Leu Glu Asn Phe Lys Leu Ser Tyr Pro Glu Ala
        195                 200                 205

Tyr Glu Lys Asn Leu Arg Gly Val Pro Met Gly Arg Phe Gly Asp Pro
210                 215                 220

Glu Leu Asp Ile Gly Arg Val Cys Val Gln Leu Gly Ser Pro Asp Phe
225                 230                 235                 240

Lys Tyr Met Ser Gly Glu Thr Leu Thr Leu Glu Gly Gly Met Gly Gln
                245                 250                 255

Arg Pro

<210> SEQ ID NO 17
<211> LENGTH: 53
<212> TYPE: DNA
<213> ORGANISM: Artificial
<220> FEATURE:
<223> OTHER INFORMATION: PCR Primer

<400> SEQUENCE: 17
aaaaaagctt ataattatcc ttataggacg tcatggtgcg cccagatagg gtg          53

<210> SEQ ID NO 18
<211> LENGTH: 60
<212> TYPE: DNA
<213> ORGANISM: Artificial
<220> FEATURE:
<223> OTHER INFORMATION: PCR Primer

<400> SEQUENCE: 18
cagattgtac aaatgtggtg ataacagata agtcgtcatg tttaacttac ctttctttgt     60

<210> SEQ ID NO 19
<211> LENGTH: 49
<212> TYPE: DNA
<213> ORGANISM: Artificial
<220> FEATURE:
<223> OTHER INFORMATION: PCR Primer

<400> SEQUENCE: 19
tgaacgcaag tttctaattt cggtttccta tcgatagagg aaagtgtct        49

<210> SEQ ID NO 20
<211> LENGTH: 27
<212> TYPE: DNA
<213> ORGANISM: Artificial
<220> FEATURE:
<223> OTHER INFORMATION: PCR Primer

<400> SEQUENCE: 20
ttaattgagc tcctgtaccc caccacc        27

<210> SEQ ID NO 21
<211> LENGTH: 30
<212> TYPE: DNA
<213> ORGANISM: Artificial
<220> FEATURE:
<223> OTHER INFORMATION: PCR Primer

<400> SEQUENCE: 21
gtgtttaatt ctgacaacct gagactcgac        30

<210> SEQ ID NO 22
<211> LENGTH: 1266
<212> TYPE: DNA
<213> ORGANISM: Artificial
<220> FEATURE:
<223> OTHER INFORMATION: FDH D221G Mutante mit His-Tag
<220> FEATURE:
<221> NAME/KEY: CDS
<222> LOCATION: (1)..(1266)

<400> SEQUENCE: 22

| | | |
|---|---|---|
| atg gca aag gtc ctg tgc gtt ctt tac gat gat ccg gtc gac ggc tac | 48 |
| Met Ala Lys Val Leu Cys Val Leu Tyr Asp Asp Pro Val Asp Gly Tyr | |
| 1               5                   10                  15 | |
| ccg aag acc tat gcc cgc gac gat ctt ccg aag atc gac cac tat ccg | 96 |
| Pro Lys Thr Tyr Ala Arg Asp Asp Leu Pro Lys Ile Asp His Tyr Pro | |
|                 20                  25                  30 | |
| ggc ggc cag atc ttg ccg acg ccg aag gcc atc gac ttc acg ccc ggg | 144 |
| Gly Gly Gln Ile Leu Pro Thr Pro Lys Ala Ile Asp Phe Thr Pro Gly | |
|             35                  40                  45 | |
| cag ttg ctc ggc tcc gtc tcc ggc gag ctc ggc ctg cgc gaa tat ctc | 192 |
| Gln Leu Leu Gly Ser Val Ser Gly Glu Leu Gly Leu Arg Glu Tyr Leu | |
|         50                  55                  60 | |
| gaa tcc aac ggc cac acc ctg gtc gtg acc tcc gac aag gac ggc ccc | 240 |
| Glu Ser Asn Gly His Thr Leu Val Val Thr Ser Asp Lys Asp Gly Pro | |
| 65                  70                  75                  80 | |
| gac tcg gtg ttc gag cgc gag ctg gtc gat gcg gat gtc gtc atc tcc | 288 |
| Asp Ser Val Phe Glu Arg Glu Leu Val Asp Ala Asp Val Val Ile Ser | |
|                 85                  90                  95 | |
| cag ccc ttc tgg ccg gcc tat ctg acg ccc gag cgc atc gcc aag gcc | 336 |
| Gln Pro Phe Trp Pro Ala Tyr Leu Thr Pro Glu Arg Ile Ala Lys Ala | |
|                 100                 105                 110 | |
| aag aac ctg aag ctc gcg ctc acc gcc ggc atc ggt tcc gac cac gtc | 384 |
| | |

```
                Lys Asn Leu Lys Leu Ala Leu Thr Ala Gly Ile Gly Ser Asp His Val
                                115                 120                 125 gat ctt cag tcg gct atc gac cgc aac gtc acc gtg gcg gaa gtc acc        432
Asp Leu Gln Ser Ala Ile Asp Arg Asn Val Thr Val Ala Glu Val Thr
130                 135                 140 tac tgc aac tcg atc agc gtc gcc gag cat gtg gtg atg atg atc ctg        480
Tyr Cys Asn Ser Ile Ser Val Ala Glu His Val Val Met Met Ile Leu
145                 150                 155                 160 tcg ctg gtg cgc aac tat ctg ccc tcg cac gaa tgg gcg cgg aag ggc        528
Ser Leu Val Arg Asn Tyr Leu Pro Ser His Glu Trp Ala Arg Lys Gly
                165                 170                 175 ggc tgg aac atc gcc gac tgc gtc tcc cac gcc tac gac ctc gag gcg        576
Gly Trp Asn Ile Ala Asp Cys Val Ser His Ala Tyr Asp Leu Glu Ala
        180                 185                 190 atg cat gtc ggc acc gtg gcc gcc ggc cgc atc ggt ctc gcg gtg ctg        624
Met His Val Gly Thr Val Ala Ala Gly Arg Ile Gly Leu Ala Val Leu
            195                 200                 205 cgc cgt ctg gcg ccg ttc gac gtg cac ctg cac tac acc ggc cgt cac        672
Arg Arg Leu Ala Pro Phe Asp Val His Leu His Tyr Thr Gly Arg His
210                 215                 220 cgc ctg ccg gaa tcg gtc gag aag gag ctc aac ctc acc tgg cac gcg        720
Arg Leu Pro Glu Ser Val Glu Lys Glu Leu Asn Leu Thr Trp His Ala
225                 230                 235                 240 acc cgc gag gac atg tat ccg gtt tgc gac gtg gtg acg ctg aac tgc        768
Thr Arg Glu Asp Met Tyr Pro Val Cys Asp Val Val Thr Leu Asn Cys
                245                 250                 255 ccg ctg cac ccc gaa acc gag cac atg atc aat gac gag acg ctg aag        816
Pro Leu His Pro Glu Thr Glu His Met Ile Asn Asp Glu Thr Leu Lys
                260                 265                 270 ctg ttc aag cgt ggc gcc tac atc gtc aac acc gcc cgc ggc aag ctg        864
Leu Phe Lys Arg Gly Ala Tyr Ile Val Asn Thr Ala Arg Gly Lys Leu
        275                 280                 285 tgc gac cgc gat gcc gtg gca cgt gcg ctc gaa tcc ggc cgg ctg gcc        912
Cys Asp Arg Asp Ala Val Ala Arg Ala Leu Glu Ser Gly Arg Leu Ala
290                 295                 300 ggc tat gcc ggc gac gtg tgg ttc ccg cag ccg gcg ccg aag gac cac        960
Gly Tyr Ala Gly Asp Val Trp Phe Pro Gln Pro Ala Pro Lys Asp His
305                 310                 315                 320 ccc tgg cgg acg atg ccc tat aac ggc atg acc ccg cac atc tcc ggc        1008
Pro Trp Arg Thr Met Pro Tyr Asn Gly Met Thr Pro His Ile Ser Gly
                325                 330                 335 acc acg ctg acc gcg cag gcg cgt tat gcg gcg ggc acc cgc gag atc        1056
Thr Thr Leu Thr Ala Gln Ala Arg Tyr Ala Ala Gly Thr Arg Glu Ile
            340                 345                 350 ctg gag tgc ttc ttc gag ggc cgt ccg atc cgc gac gaa tac ctc atc        1104
Leu Glu Cys Phe Phe Glu Gly Arg Pro Ile Arg Asp Glu Tyr Leu Ile
                355                 360                 365 gtg cag ggc ggc gct ctt gcc ggc acc ggc gcg cat tcc tac tcg aag        1152
Val Gln Gly Gly Ala Leu Ala Gly Thr Gly Ala His Ser Tyr Ser Lys
        370                 375                 380 ggc aat gcc acc ggc ggt tcg gaa gag gcc gcc aag ttc aag aag gcg        1200
Gly Asn Ala Thr Gly Gly Ser Glu Glu Ala Ala Lys Phe Lys Lys Ala
385                 390                 395                 400 gct gag aat tcg agc tcc gtc gac aag ctt gcg gcc gca ctc gag cac        1248
Ala Glu Asn Ser Ser Ser Val Asp Lys Leu Ala Ala Ala Leu Glu His
                405                 410                 415 cac cac cac cac cac tga                                                1266
His His His His His
            420
```

<210> SEQ ID NO 23
<211> LENGTH: 421
<212> TYPE: PRT
<213> ORGANISM: Artificial
<220> FEATURE:
<223> OTHER INFORMATION: Synthetic Construct

<400> SEQUENCE: 23

```
Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Gly Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365
```

```
Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Ala Glu Asn Ser Ser Ser Val Asp Lys Leu Ala Ala Ala Leu Glu His
                405                 410                 415

His His His His His
        420

<210> SEQ ID NO 24
<211> LENGTH: 792
<212> TYPE: DNA
<213> ORGANISM: Collinsella aerofaciens
<220> FEATURE:
<221> NAME/KEY: CDS
<222> LOCATION: (1)..(792)

<400> SEQUENCE: 24
```

| | | | | | | | | | | | | | | | | |
|---|---|---|---|---|---|---|---|---|---|---|---|---|---|---|---|---|
| atg | aac | ctg | agg | gag | aag | tac | ggt | gag | tgg | ggc | ctg | atc | ctg | ggc | gcg | 48 |
| Met | Asn | Leu | Arg | Glu | Lys | Tyr | Gly | Glu | Trp | Gly | Leu | Ile | Leu | Gly | Ala | |
| 1 | | | | 5 | | | | | 10 | | | | | 15 | | |
| acc | gag | ggc | gtc | ggc | aag | gcg | ttc | tgc | gag | aag | atc | gcc | gcc | ggc | ggc | 96 |
| Thr | Glu | Gly | Val | Gly | Lys | Ala | Phe | Cys | Glu | Lys | Ile | Ala | Ala | Gly | Gly | |
| | | | 20 | | | | | 25 | | | | | 30 | | | |
| atg | aac | gtc | gtc | atg | gtc | ggc | cgt | cgc | gag | gag | aag | ctg | aac | gtg | ctc | 144 |
| Met | Asn | Val | Val | Met | Val | Gly | Arg | Arg | Glu | Glu | Lys | Leu | Asn | Val | Leu | |
| | | 35 | | | | | 40 | | | | | 45 | | | | |
| gca | ggc | gag | atc | cgc | gag | acc | tac | ggc | gtg | gag | acc | aag | gtc | gtg | cgc | 192 |
| Ala | Gly | Glu | Ile | Arg | Glu | Thr | Tyr | Gly | Val | Glu | Thr | Lys | Val | Val | Arg | |
| | 50 | | | | | 55 | | | | | 60 | | | | | |
| gcc | gac | ttt | agc | cag | ccc | ggc | gct | gcc | gag | acc | gtc | ttc | gcc | gcg | acc | 240 |
| Ala | Asp | Phe | Ser | Gln | Pro | Gly | Ala | Ala | Glu | Thr | Val | Phe | Ala | Ala | Thr | |
| 65 | | | | | 70 | | | | | 75 | | | | | 80 | |
| gag | ggc | ctg | gac | atg | ggc | ttc | atg | agc | tac | gtg | gcc | tgc | ctg | cac | agc | 288 |
| Glu | Gly | Leu | Asp | Met | Gly | Phe | Met | Ser | Tyr | Val | Ala | Cys | Leu | His | Ser | |
| | | | | 85 | | | | | 90 | | | | | 95 | | |
| ttc | ggt | aag | atc | cag | gac | acc | ccc | tgg | gag | aag | cac | gag | gcc | atg | atc | 336 |
| Phe | Gly | Lys | Ile | Gln | Asp | Thr | Pro | Trp | Glu | Lys | His | Glu | Ala | Met | Ile | |
| | | | 100 | | | | | 105 | | | | | 110 | | | |
| aac | gtc | aac | gtc | gtg | acc | ttc | ctc | aag | tgc | ttc | cac | cac | tac | atg | cgg | 384 |
| Asn | Val | Asn | Val | Val | Thr | Phe | Leu | Lys | Cys | Phe | His | His | Tyr | Met | Arg | |
| | | 115 | | | | | 120 | | | | | 125 | | | | |
| atc | ttt | gcc | gcc | cag | gac | cgc | ggc | gcc | gtg | atc | aac | gtc | tcg | tcg | atg | 432 |
| Ile | Phe | Ala | Ala | Gln | Asp | Arg | Gly | Ala | Val | Ile | Asn | Val | Ser | Ser | Met | |
| | 130 | | | | | 135 | | | | | 140 | | | | | |
| acc | ggc | atc | agc | tcc | agc | ccc | tgg | aac | ggc | cag | tac | ggc | gcg | ggc | aag | 480 |
| Thr | Gly | Ile | Ser | Ser | Ser | Pro | Trp | Asn | Gly | Gln | Tyr | Gly | Ala | Gly | Lys | |
| 145 | | | | | 150 | | | | | 155 | | | | | 160 | |
| gcc | ttc | atc | ctc | aag | atg | acc | gag | gcc | gtg | gcc | tgc | gag | tgc | gag | ggc | 528 |
| Ala | Phe | Ile | Leu | Lys | Met | Thr | Glu | Ala | Val | Ala | Cys | Glu | Cys | Glu | Gly | |
| | | | | 165 | | | | | 170 | | | | | 175 | | |
| acc | ggc | gtc | gac | gtc | gag | gtc | atc | acc | ctc | ggc | acc | acc | cta | acc | ccc | 576 |
| Thr | Gly | Val | Asp | Val | Glu | Val | Ile | Thr | Leu | Gly | Thr | Thr | Leu | Thr | Pro | |
| | | | 180 | | | | | 185 | | | | | 190 | | | |
| agc | ctg | ctg | tcc | aac | ctc | ccc | ggc | ggc | ccg | cag | ggc | gag | gcc | gtc | atg | 624 |
| Ser | Leu | Leu | Ser | Asn | Leu | Pro | Gly | Gly | Pro | Gln | Gly | Glu | Ala | Val | Met | |
| | | 195 | | | | | 200 | | | | | 205 | | | | |
| aag | atc | gcc | ctc | acc | ccc | gag | gag | tgc | gtt | gac | gag | gcc | ttt | gag | aag | 672 |
| Lys | Ile | Ala | Leu | Thr | Pro | Glu | Glu | Cys | Val | Asp | Glu | Ala | Phe | Glu | Lys | |
| | 210 | | | | | 215 | | | | | 220 | | | | | |

```
ctg ggt aag gag ctc tcc gtc atc gcc ggc cag cgc aac aag gac tcc    720
Leu Gly Lys Glu Leu Ser Val Ile Ala Gly Gln Arg Asn Lys Asp Ser
225                 230                 235                 240 gtc cac gac tgg aag gca aac cac acc gag gac gag tac atc cgc tac    768
Val His Asp Trp Lys Ala Asn His Thr Glu Asp Glu Tyr Ile Arg Tyr
                245                 250                 255 atg ggg tcg ttc tac cgc gac tag                                    792
Met Gly Ser Phe Tyr Arg Asp
            260

<210> SEQ ID NO 25
<211> LENGTH: 263
<212> TYPE: PRT
<213> ORGANISM: Collinsella aerofaciens

<400> SEQUENCE: 25

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Gly Arg Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 26
<211> LENGTH: 31
<212> TYPE: DNA
<213> ORGANISM: artificial
<220> FEATURE:
<223> OTHER INFORMATION: PCR Primer
```

-continued

<400> SEQUENCE: 26
gggaattcca tatgaacctg agggagaagt a                                           31

<210> SEQ ID NO 27
<211> LENGTH: 27
<212> TYPE: DNA
<213> ORGANISM: Artificial
<220> FEATURE:
<223> OTHER INFORMATION: PCR Primer

<400> SEQUENCE: 27
cccaagcttc tagtcgcggt agaacga                                                27

<210> SEQ ID NO 28
<211> LENGTH: 774
<212> TYPE: DNA
<213> ORGANISM: Comamonas testosteroni
<220> FEATURE:
<221> NAME/KEY: CDS
<222> LOCATION: (1)..(774)

<400> SEQUENCE: 28

```
atg tcc atc atc gtg ata agc ggc tgc gcc acc ggc att ggt gcc gct      48
Met Ser Ile Ile Val Ile Ser Gly Cys Ala Thr Gly Ile Gly Ala Ala
1               5                   10                  15 acg cgc aag gtc ctg gag gcg gcc ggt cac cag atc gta ggc atc gat      96
Thr Arg Lys Val Leu Glu Ala Ala Gly His Gln Ile Val Gly Ile Asp
                20                  25                  30 ata cgc gat gcg gaa gtg att gcc gat ctc tcg acg gcc gaa ggt cga     144
Ile Arg Asp Ala Glu Val Ile Ala Asp Leu Ser Thr Ala Glu Gly Arg
            35                  40                  45 aag cag gcg att gcc gat gta ctg gcg aag tgc agc aag ggc atg gac     192
Lys Gln Ala Ile Ala Asp Val Leu Ala Lys Cys Ser Lys Gly Met Asp
        50                  55                  60 ggc ctg gtg ctg tgc gcc ggc ctg gga ccg cag acc aag gtg ctt ggc     240
Gly Leu Val Leu Cys Ala Gly Leu Gly Pro Gln Thr Lys Val Leu Gly
65                  70                  75                  80 aat gtg gtt tcg gtc aat tat ttt ggc gcg acc gag ctg atg gat gcc     288
Asn Val Val Ser Val Asn Tyr Phe Gly Ala Thr Glu Leu Met Asp Ala
                85                  90                  95 ttt ttg cca gcg ctg aaa aaa ggc cat cag ccc gca gcc gtc gtc atc     336
Phe Leu Pro Ala Leu Lys Lys Gly His Gln Pro Ala Ala Val Val Ile
                100                 105                 110 tcg tcc gtg gct tcc gcg cat ctg gct ttt gac aag aac cca ctg gcg     384
Ser Ser Val Ala Ser Ala His Leu Ala Phe Asp Lys Asn Pro Leu Ala
            115                 120                 125 ctg gca ctg gaa gcc ggc gag gaa gcc aag gcc cgc gcc att gtc gaa     432
Leu Ala Leu Glu Ala Gly Glu Glu Ala Lys Ala Arg Ala Ile Val Glu
        130                 135                 140 cat gcg gga gag cag ggc gga aat ctg gcc tat gcg ggc agc aag aat     480
His Ala Gly Glu Gln Gly Gly Asn Leu Ala Tyr Ala Gly Ser Lys Asn
145                 150                 155                 160 gct ttg acg gtg gct gtg cgc aaa cgc gcc gcc gcc tgg ggc gag gct     528
Ala Leu Thr Val Ala Val Arg Lys Arg Ala Ala Ala Trp Gly Glu Ala
                165                 170                 175 ggc gtg cgc ctg aac acc atc gcc ccc ggt gca acc gag act ccc ttg     576
Gly Val Arg Leu Asn Thr Ile Ala Pro Gly Ala Thr Glu Thr Pro Leu
            180                 185                 190 ctg cag gcg ggc ctg cag gac ccg cgc tat ggc gaa tcc att gcc aag     624
Leu Gln Ala Gly Leu Gln Asp Pro Arg Tyr Gly Glu Ser Ile Ala Lys
        195                 200                 205
```

```
ttc gtt cct ccc atg ggc cgc cgt gcc gag ccg tcc gag atg gcg tcg    672
Phe Val Pro Pro Met Gly Arg Arg Ala Glu Pro Ser Glu Met Ala Ser
    210                 215                 220 gtc atc gcc ttt ttg atg agc ccg gcc gca agc tat gtg cat ggc gcg    720
Val Ile Ala Phe Leu Met Ser Pro Ala Ala Ser Tyr Val His Gly Ala
225                 230                 235                 240 cag atc gtc att gat ggc ggc att gat gcg gtg atg cgc ccg aca cag    768
Gln Ile Val Ile Asp Gly Gly Ile Asp Ala Val Met Arg Pro Thr Gln
                245                 250                 255 ttc tga                                                            774
Phe
```

<210> SEQ ID NO 29
<211> LENGTH: 257
<212> TYPE: PRT
<213> ORGANISM: Comamonas testosteroni

<400> SEQUENCE: 29

```
Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Arg Asp Ala Glu Val Ile Ala Asp Leu Ser Thr Ala Glu Gly Arg
        35                  40                  45

Lys Gln Ala Ile Ala Asp Val Leu Ala Lys Cys Ser Lys Gly Met Asp
    50                  55                  60

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Ala Val Val Ile
            100                 105                 110

Ser Ser Val Ala Ser Ala His Leu Ala Phe Asp Lys Asn Pro Leu Ala
        115                 120                 125

Leu Ala Leu Glu Ala Gly Glu Glu Ala Lys Ala Arg Ala Ile Val Glu
    130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Trp Gly Glu Ala
                165                 170                 175

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe
```

<210> SEQ ID NO 30
<211> LENGTH: 969
<212> TYPE: DNA
<213> ORGANISM: Rattus norvegicus
<220> FEATURE:

<221> NAME/KEY: CDS
<222> LOCATION: (1)..(969)

<400> SEQUENCE: 30

| | | | | | | | | | | | | | | | | |
|---|---|---|---|---|---|---|---|---|---|---|---|---|---|---|---|---|
| atg | gat | tcc | ata | tct | ctg | cgt | gta | gca | cta | aat | gat | ggt | aac | ttc | att | 48 |
| Met | Asp | Ser | Ile | Ser | Leu | Arg | Val | Ala | Leu | Asn | Asp | Gly | Asn | Phe | Ile | |
| 1 | | | | 5 | | | | | 10 | | | | | 15 | | |
| cct | gta | ctg | ggg | ttt | gga | acc | act | gtg | cct | gag | aag | gtt | gct | aag | gat | 96 |
| Pro | Val | Leu | Gly | Phe | Gly | Thr | Thr | Val | Pro | Glu | Lys | Val | Ala | Lys | Asp | |
| | | | 20 | | | | | 25 | | | | | 30 | | | |
| gaa | gtt | atc | aag | gct | act | aaa | ata | gct | ata | gat | aat | gga | ttc | cgc | cat | 144 |
| Glu | Val | Ile | Lys | Ala | Thr | Lys | Ile | Ala | Ile | Asp | Asn | Gly | Phe | Arg | His | |
| | | 35 | | | | | 40 | | | | | 45 | | | | |
| ttt | gac | tct | gct | tat | ttg | tac | gaa | gta | gaa | gag | gaa | gtg | ggc | caa | gcc | 192 |
| Phe | Asp | Ser | Ala | Tyr | Leu | Tyr | Glu | Val | Glu | Glu | Glu | Val | Gly | Gln | Ala | |
| 50 | | | | | 55 | | | | | 60 | | | | | | |
| att | aga | agc | aag | att | gaa | gac | ggc | act | gtg | aag | aga | gaa | gat | ata | ttc | 240 |
| Ile | Arg | Ser | Lys | Ile | Glu | Asp | Gly | Thr | Val | Lys | Arg | Glu | Asp | Ile | Phe | |
| 65 | | | | | 70 | | | | | 75 | | | | | 80 | |
| tat | act | tca | aag | ctt | tgg | agc | act | ttc | cat | aga | cca | gag | ctg | gtc | cga | 288 |
| Tyr | Thr | Ser | Lys | Leu | Trp | Ser | Thr | Phe | His | Arg | Pro | Glu | Leu | Val | Arg | |
| | | | | 85 | | | | | 90 | | | | | 95 | | |
| act | tgc | ttg | gaa | aag | aca | ctg | aaa | agc | act | caa | ctg | gac | tat | gtg | gat | 336 |
| Thr | Cys | Leu | Glu | Lys | Thr | Leu | Lys | Ser | Thr | Gln | Leu | Asp | Tyr | Val | Asp | |
| | | | 100 | | | | | 105 | | | | | 110 | | | |
| ctt | tat | att | att | cat | ttc | cca | atg | gct | ttg | cag | cct | gga | gat | ata | ttt | 384 |
| Leu | Tyr | Ile | Ile | His | Phe | Pro | Met | Ala | Leu | Gln | Pro | Gly | Asp | Ile | Phe | |
| | | | 115 | | | | | 120 | | | | | 125 | | | |
| ttc | cca | cga | gat | gag | cat | gga | aaa | cta | ttg | ttt | gaa | aca | gtg | gat | atc | 432 |
| Phe | Pro | Arg | Asp | Glu | His | Gly | Lys | Leu | Leu | Phe | Glu | Thr | Val | Asp | Ile | |
| 130 | | | | | 135 | | | | | 140 | | | | | | |
| tgt | gac | aca | tgg | gag | gcc | atg | gaa | aag | tgt | aag | gat | gca | gga | ttg | gcc | 480 |
| Cys | Asp | Thr | Trp | Glu | Ala | Met | Glu | Lys | Cys | Lys | Asp | Ala | Gly | Leu | Ala | |
| 145 | | | | | 150 | | | | | 155 | | | | | 160 | |
| aag | tct | att | ggg | gtg | tcc | aac | ttt | aac | tgc | agg | cag | ctg | gag | agg | att | 528 |
| Lys | Ser | Ile | Gly | Val | Ser | Asn | Phe | Asn | Cys | Arg | Gln | Leu | Glu | Arg | Ile | |
| | | | | 165 | | | | | 170 | | | | | 175 | | |
| ctg | aat | aag | cca | ggg | ctc | aaa | tac | aag | cct | gtg | tgc | aac | cag | gtg | gaa | 576 |
| Leu | Asn | Lys | Pro | Gly | Leu | Lys | Tyr | Lys | Pro | Val | Cys | Asn | Gln | Val | Glu | |
| | | | 180 | | | | | 185 | | | | | 190 | | | |
| tgt | cac | ctt | tat | ctc | aac | cag | agc | aaa | atg | ctg | gac | tat | tgt | aag | tca | 624 |
| Cys | His | Leu | Tyr | Leu | Asn | Gln | Ser | Lys | Met | Leu | Asp | Tyr | Cys | Lys | Ser | |
| | | | 195 | | | | | 200 | | | | | 205 | | | |
| aaa | gac | atc | att | ctg | gtt | tcc | tac | tgc | acg | ctg | gga | agt | tca | cga | gac | 672 |
| Lys | Asp | Ile | Ile | Leu | Val | Ser | Tyr | Cys | Thr | Leu | Gly | Ser | Ser | Arg | Asp | |
| | | 210 | | | | | 215 | | | | | 220 | | | | |
| aaa | aca | tgg | gtg | gat | cag | aaa | agt | cca | gtt | ctc | cta | gat | gat | cca | gtt | 720 |
| Lys | Thr | Trp | Val | Asp | Gln | Lys | Ser | Pro | Val | Leu | Leu | Asp | Asp | Pro | Val | |
| 225 | | | | | 230 | | | | | 235 | | | | | 240 | |
| ctt | tgt | gcc | ata | gca | aag | aag | tac | aag | caa | acc | cca | gcc | cta | gtt | gcc | 768 |
| Leu | Cys | Ala | Ile | Ala | Lys | Lys | Tyr | Lys | Gln | Thr | Pro | Ala | Leu | Val | Ala | |
| | | | | 245 | | | | | 250 | | | | | 255 | | |
| ctt | cgc | tac | cag | ctg | cag | cgt | ggg | gtt | gtg | ccc | ctg | atc | agg | agt | ttc | 816 |
| Leu | Arg | Tyr | Gln | Leu | Gln | Arg | Gly | Val | Val | Pro | Leu | Ile | Arg | Ser | Phe | |
| | | | 260 | | | | | 265 | | | | | 270 | | | |
| aac | gcg | aag | cgg | atc | aaa | gag | cta | aca | cag | gtt | ttt | gaa | ttc | cag | ttg | 864 |
| Asn | Ala | Lys | Arg | Ile | Lys | Glu | Leu | Thr | Gln | Val | Phe | Glu | Phe | Gln | Leu | |
| | | 275 | | | | | 280 | | | | | 285 | | | | |
| gct | tca | gag | gac | atg | aaa | gcc | ctg | gat | ggc | ttg | aac | aga | aat | ttc | aga | 912 |
| Ala | Ser | Glu | Asp | Met | Lys | Ala | Leu | Asp | Gly | Leu | Asn | Arg | Asn | Phe | Arg | |

|  | 290 |  |  |  | 295 |  |  |  | 300 |  |  |  |  |
|---|---|---|---|---|---|---|---|---|---|---|---|---|---|
| tac | aac | aat | gca | aaa | tat | ttt | gat | gac | cat | ccc | aat | cat | cca | ttt | act | 960 |
| Tyr | Asn | Asn | Ala | Lys | Tyr | Phe | Asp | Asp | His | Pro | Asn | His | Pro | Phe | Thr |  |
| 305 |  |  |  | 310 |  |  |  | 315 |  |  |  |  | 320 |  |  |  |

| gat | gaa | tag | 969 |
|---|---|---|---|
| Asp | Glu |  |  |

<210> SEQ ID NO 31
<211> LENGTH: 322
<212> TYPE: PRT
<213> ORGANISM: Rattus norvegicus

<400> SEQUENCE: 31

Met Asp Ser Ile Ser Leu Arg Val Ala Leu Asn Asp Gly Asn Phe Ile
1               5                   10                  15

Pro Val Leu Gly Phe Gly Thr Thr Val Pro Glu Lys Val Ala Lys Asp
            20                  25                  30

Glu Val Ile Lys Ala Thr Lys Ile Ala Ile Asp Asn Gly Phe Arg His
        35                  40                  45

Phe Asp Ser Ala Tyr Leu Tyr Glu Val Glu Glu Val Gly Gln Ala
    50                  55                  60

Ile Arg Ser Lys Ile Glu Asp Gly Thr Val Lys Arg Glu Asp Ile Phe
65                  70                  75                  80

Tyr Thr Ser Lys Leu Trp Ser Thr Phe His Arg Pro Glu Leu Val Arg
                85                  90                  95

Thr Cys Leu Glu Lys Thr Leu Lys Ser Thr Gln Leu Asp Tyr Val Asp
            100                 105                 110

Leu Tyr Ile Ile His Phe Pro Met Ala Leu Gln Pro Gly Asp Ile Phe
        115                 120                 125

Phe Pro Arg Asp Glu His Gly Lys Leu Leu Phe Glu Thr Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Cys Arg Gln Leu Glu Arg Ile
                165                 170                 175

Leu Asn Lys Pro Gly Leu Lys Tyr Lys Pro Val Cys Asn Gln Val Glu
            180                 185                 190

Cys His Leu Tyr Leu Asn Gln Ser Lys Met Leu Asp Tyr Cys Lys Ser
        195                 200                 205

Lys Asp Ile Ile Leu Val Ser Tyr Cys Thr Leu Gly Ser Ser Arg Asp
    210                 215                 220

Lys Thr Trp Val Asp Gln Lys Ser Pro Val Leu Leu Asp Asp Pro Val
225                 230                 235                 240

Leu Cys Ala Ile Ala Lys Lys Tyr Lys Gln Thr Pro Ala Leu Val Ala
                245                 250                 255

Leu Arg Tyr Gln Leu Gln Arg Gly Val Val Pro Leu Ile Arg Ser Phe
            260                 265                 270

Asn Ala Lys Arg Ile Lys Glu Leu Thr Gln Val Phe Glu Phe Gln Leu
        275                 280                 285

Ala Ser Glu Asp Met Lys Ala Leu Asp Gly Leu Asn Arg Asn Phe Arg
    290                 295                 300

Tyr Asn Asn Ala Lys Tyr Phe Asp Asp His Pro Asn His Pro Phe Thr
305                 310                 315                 320

Asp Glu

<210> SEQ ID NO 32
<211> LENGTH: 401
<212> TYPE: PRT
<213> ORGANISM: Mycobacterium vaccae

<400> SEQUENCE: 32

```
Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380
```

Gly Asn Ala Thr Gly Gly Ser Glu Glu Ala Ala Lys Phe Lys Lys Ala
385                 390                 395                 400

Val

<210> SEQ ID NO 33
<211> LENGTH: 29
<212> TYPE: DNA
<213> ORGANISM: Artificial
<220> FEATURE:
<223> OTHER INFORMATION: PCR Primer

<400> SEQUENCE: 33
cgatcatatg gcaaaggtcc tgtgcgttc                              29

<210> SEQ ID NO 34
<211> LENGTH: 29
<212> TYPE: DNA
<213> ORGANISM: Artificial
<220> FEATURE:
<223> OTHER INFORMATION: PCR Primer

<400> SEQUENCE: 34
gctagaattc tcagccgcct tcttgaact                              29

<210> SEQ ID NO 35
<211> LENGTH: 29
<212> TYPE: DNA
<213> ORGANISM: Artificial
<220> FEATURE:
<223> OTHER INFORMATION: PCR Primer

<400> SEQUENCE: 35
cctgcactac accggccgtc accgcctgc                              29

<210> SEQ ID NO 36
<211> LENGTH: 23
<212> TYPE: DNA
<213> ORGANISM: Artificial
<220> FEATURE:
<223> OTHER INFORMATION: PCR Primer

<400> SEQUENCE: 36
gctcgaattc tcagaccgcc ttc                                    23

<210> SEQ ID NO 37
<211> LENGTH: 1206
<212> TYPE: DNA
<213> ORGANISM: Artificial
<220> FEATURE:
<223> OTHER INFORMATION: Formiate Deydrogenase Mutant
<220> FEATURE:
<221> NAME/KEY: CDS
<222> LOCATION: (1)..(1206)

<400> SEQUENCE: 37 atg gca aag gtc ctg tgc gtt ctt tac gat gat ccg gtc gac ggc tac    48
Met Ala Lys Val Leu Cys Val Leu Tyr Asp Asp Pro Val Asp Gly Tyr
1               5                   10                  15 ccg aag acc tat gcc cgc gac gat ctt ccg aag atc gac cac tat ccg    96
Pro Lys Thr Tyr Ala Arg Asp Asp Leu Pro Lys Ile Asp His Tyr Pro
                20                  25                  30 ggc ggc cag atc ttg ccg acg ccg aag gcc atc gac ttc acg ccc ggg   144
Gly Gly Gln Ile Leu Pro Thr Pro Lys Ala Ile Asp Phe Thr Pro Gly
            35                  40                  45

|   |   |
|---|---|
| cag ttg ctc ggc tcc gtc tcc ggc gag ctc ggc ctg cgc gaa tat ctc<br>Gln Leu Leu Gly Ser Val Ser Gly Glu Leu Gly Leu Arg Glu Tyr Leu<br>    50                        55                      60 | 192 |
| gaa tcc aac ggc cac acc ctg gtc gtg acc tcc gac aag gac ggc ccc<br>Glu Ser Asn Gly His Thr Leu Val Val Thr Ser Asp Lys Asp Gly Pro<br>65                     70                      75                      80 | 240 |
| gac tcg gtg ttc gag cgc gag ctg gtc gat gcg gat gtc gtc atc tcc<br>Asp Ser Val Phe Glu Arg Glu Leu Val Asp Ala Asp Val Val Ile Ser<br>                85                      90                      95 | 288 |
| cag ccc ttc tgg ccg gcc tat ctg acg ccc gag cgc atc gcc aag gcc<br>Gln Pro Phe Trp Pro Ala Tyr Leu Thr Pro Glu Arg Ile Ala Lys Ala<br>                100                    105                 110 | 336 |
| aag aac ctg aag ctc gcg ctc acc gcc ggc atc ggt tcc gac cac gtc<br>Lys Asn Leu Lys Leu Ala Leu Thr Ala Gly Ile Gly Ser Asp His Val<br>          115                    120                    125 | 384 |
| gat ctt cag tcg gct atc gac cgc aac gtc acc gtg gcg gaa gtc acc<br>Asp Leu Gln Ser Ala Ile Asp Arg Asn Val Thr Val Ala Glu Val Thr<br>130                     135                    140 | 432 |
| tac tgc aac tcg atc agc gtc gcc gag cat gtg gtg atg atg atc ctg<br>Tyr Cys Asn Ser Ile Ser Val Ala Glu His Val Val Met Met Ile Leu<br>145                     150                    155                 160 | 480 |
| tcg ctg gtg cgc aac tat ctg ccc tcg cac gaa tgg gcg cgg aag ggc<br>Ser Leu Val Arg Asn Tyr Leu Pro Ser His Glu Trp Ala Arg Lys Gly<br>                165                    170                 175 | 528 |
| ggc tgg aac atc gcc gac tgc gtc tcc cac gcc tac gac ctc gag gcg<br>Gly Trp Asn Ile Ala Asp Cys Val Ser His Ala Tyr Asp Leu Glu Ala<br>              180                    185                 190 | 576 |
| atg cat gtc ggc acc gtg gcc gcc ggc cgc atc ggt ctc gcg gtg ctg<br>Met His Val Gly Thr Val Ala Ala Gly Arg Ile Gly Leu Ala Val Leu<br>          195                    200                    205 | 624 |
| cgc cgt ctg gcg ccg ttc gac gtg cac ctg cac tac acc ggc cgt cac<br>Arg Arg Leu Ala Pro Phe Asp Val His Leu His Tyr Thr Gly Arg His<br>210                     215                    220 | 672 |
| cgc ctg ccg gaa tcg gtc gag aag gag ctc aac ctc acc tgg cac gcg<br>Arg Leu Pro Glu Ser Val Glu Lys Glu Leu Asn Leu Thr Trp His Ala<br>225                     230                    235                 240 | 720 |
| acc cgc gag gac atg tat ccg gtt tgc gac gtg gtg acg ctg aac tgc<br>Thr Arg Glu Asp Met Tyr Pro Val Cys Asp Val Val Thr Leu Asn Cys<br>                245                    250                 255 | 768 |
| ccg ctg cac ccc gaa acc gag cac atg atc aat gac gag acg ctg aag<br>Pro Leu His Pro Glu Thr Glu His Met Ile Asn Asp Glu Thr Leu Lys<br>                260                    265                 270 | 816 |
| ctg ttc aag cgt ggc gcc tac atc gtc aac acc gcc cgc ggc aag ctg<br>Leu Phe Lys Arg Gly Ala Tyr Ile Val Asn Thr Ala Arg Gly Lys Leu<br>          275                    280                    285 | 864 |
| tgc gac cgc gat gcc gtg gca cgt gcg ctc gaa tcc ggc cgg ctg gcc<br>Cys Asp Arg Asp Ala Val Ala Arg Ala Leu Glu Ser Gly Arg Leu Ala<br>290                     295                    300 | 912 |
| ggc tat gcc ggc gac gtg tgg ttc ccg cag ccg gcg ccg aag gac cac<br>Gly Tyr Ala Gly Asp Val Trp Phe Pro Gln Pro Ala Pro Lys Asp His<br>305                     310                    315                 320 | 960 |
| ccc tgg cgg acg atg ccc tat aac ggc atg acc ccg cac atc tcc ggc<br>Pro Trp Arg Thr Met Pro Tyr Asn Gly Met Thr Pro His Ile Ser Gly<br>                325                    330                 335 | 1008 |
| acc acg ctg acc gcg cag gcg cgt tat gcg gcg ggc acc cgc gag atc<br>Thr Thr Leu Thr Ala Gln Ala Arg Tyr Ala Ala Gly Thr Arg Glu Ile<br>                340                    345                 350 | 1056 |
| ctg gag tgc ttc ttc gag ggc cgt ccg atc cgc gac gaa tac ctc atc<br>Leu Glu Cys Phe Phe Glu Gly Arg Pro Ile Arg Asp Glu Tyr Leu Ile<br>          355                    360                    365 | 1104 |

```
gtg cag ggc ggc gct ctt gcc ggc acc ggc gcg cat tcc tac tcg aag      1152
Val Gln Gly Gly Ala Leu Ala Gly Thr Gly Ala His Ser Tyr Ser Lys
370                 375                 380 ggc aat gcc acc ggc ggt tcg gaa gag gcc gcc aag ttc aag aag gcg      1200
Gly Asn Ala Thr Gly Gly Ser Glu Glu Ala Ala Lys Phe Lys Lys Ala
385                 390                 395                 400 gtc tga                                                              1206
Val
```

<210> SEQ ID NO 38
<211> LENGTH: 401
<212> TYPE: PRT
<213> ORGANISM: Artificial
<220> FEATURE:
<223> OTHER INFORMATION: Synthetic Construct

<400> SEQUENCE: 38

```
Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
                20                  25                  30

Gly Gly Gln Ile Leu Pro Thr Pro Lys Ala Ile Asp Phe Thr Pro Gly
            35                  40                  45

Gln Leu Leu Gly Ser Val Ser Gly Glu Leu Gly Leu Arg Glu Tyr Leu
50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Gly Arg His
210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
290                 295                 300
```

-continued

```
Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Val

<210> SEQ ID NO 39
<211> LENGTH: 4
<212> TYPE: PRT
<213> ORGANISM: Artificial Sequence
<220> FEATURE:
<223> OTHER INFORMATION: Partial  amino acid sequence

<400> SEQUENCE: 39

Leu Ile Asn Asn
1

<210> SEQ ID NO 40
<211> LENGTH: 6
<212> TYPE: PRT
<213> ORGANISM: Artificial Sequence
<220> FEATURE:
<223> OTHER INFORMATION: Partial amino acid sequence

<400> SEQUENCE: 40

Arg Met Gly Ile Phe Asp
1               5

<210> SEQ ID NO 41
<211> LENGTH: 41
<212> TYPE: PRT
<213> ORGANISM: Artificial Sequence
<220> FEATURE:
<223> OTHER INFORMATION: Partial amino acid sequence

<400> SEQUENCE: 41

Met Asp Phe Ile Asp Phe Lys Glu Met Gly Arg Met Gly Ile Phe Asp
1               5                   10                  15

Gly Lys Val Ala Ile Ile Thr Gly Gly Gly Lys Ala Lys Ser Ile Gly
            20                  25                  30

Tyr Gly Ile Ala Val Ala Tyr Ala Lys
        35                  40

<210> SEQ ID NO 42
<211> LENGTH: 14
<212> TYPE: PRT
<213> ORGANISM: Artificial Sequence
<220> FEATURE:
<223> OTHER INFORMATION: Partial amino acid sequence

<400> SEQUENCE: 42

Met Asp Phe Ile Asp Phe Lys Glu Met Gly Arg Met Gly Ile
1               5                   10
```

```
<210> SEQ ID NO 43
<211> LENGTH: 15
<212> TYPE: PRT
<213> ORGANISM: Artificial Sequence
<220> FEATURE:
<223> OTHER INFORMATION: Partial amino acid sequence

<400> SEQUENCE: 43

Ile Thr Gly Gly Gly Lys Ala Lys Ser Ile Gly Tyr Gly Ile Ala
1               5                   10                  15

<210> SEQ ID NO 44
<211> LENGTH: 5
<212> TYPE: PRT
<213> ORGANISM: Artificial Sequence
<220> FEATURE:
<223> OTHER INFORMATION: Partial amino acid sequence

<400> SEQUENCE: 44

Ile Phe Asp Gly Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Partial amino acid sequence

<400> SEQUENCE: 45

Gly Ile Phe Asp Gly Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Partial amino acid sequence

<400> SEQUENCE: 46

Phe Gly Asp Pro Glu Leu Asp Ile
1               5

<210> SEQ ID NO 47
<211> LENGTH: 7
<212> TYPE: PRT
<213> ORGANISM: Artificial Sequence
<220> FEATURE:
<223> OTHER INFORMATION: Partial amino acid sequence

<400> SEQUENCE: 47

Gly Asp Pro Glu Leu Asp Ile
1               5

<210> SEQ ID NO 48
<211> LENGTH: 7
<212> TYPE: PRT
<213> ORGANISM: Artificial Sequence
<220> FEATURE:
<223> OTHER INFORMATION: Partial amino acid sequence

<400> SEQUENCE: 48

Phe Gly Asp Pro Glu Leu Asp
1               5

<210> SEQ ID NO 49
```

```
<211> LENGTH: 6
<212> TYPE: PRT
<213> ORGANISM: Artificial Sequence
<220> FEATURE:
<223> OTHER INFORMATION: Partial amino acid sequence

<400> SEQUENCE: 49

Asp Pro Glu Leu Asp Ile
1               5

<210> SEQ ID NO 50
<211> LENGTH: 6
<212> TYPE: PRT
<213> ORGANISM: Artificial Sequence
<220> FEATURE:
<223> OTHER INFORMATION: Partial amino acid sequence

<400> SEQUENCE: 50

Phe Gly Asp Pro Glu Leu
1               5

<210> SEQ ID NO 51
<211> LENGTH: 5
<212> TYPE: PRT
<213> ORGANISM: Artificial Sequence
<220> FEATURE:
<223> OTHER INFORMATION: Partial amino acid sequence

<400> SEQUENCE: 51

Gly Asp Pro Glu Leu
1               5

<210> SEQ ID NO 52
<211> LENGTH: 5
<212> TYPE: PRT
<213> ORGANISM: Artificial Sequence
<220> FEATURE:
<223> OTHER INFORMATION: Partial amino acid sequence

<400> SEQUENCE: 52

Asp Pro Glu Leu Asp
1               5

<210> SEQ ID NO 53
<211> LENGTH: 6
<212> TYPE: PRT
<213> ORGANISM: Artificial Sequence
<220> FEATURE:
<223> OTHER INFORMATION: Partial amino acid sequence

<400> SEQUENCE: 53

Gly Asp Pro Glu Leu Asp
1               5
```

7 α-HYDROXYSTEROID DEHYDROGENASE KNOCKOUT MUTANTS AND USE THEREFOR

This application is the U.S. national phase, pursuant to 35 U.S.C. §371, of PCT international application Ser. No. PCT/EP2011/058711, filed May 27, 2011, designating the United States and published on Dec. 1, 2011 as publication WO 2011/147957 A1, which claims priority to European Application Ser. Nos. 10164003.5, filed May 27, 2010 and 10015726.2, filed Dec. 16, 2010. The entire contents of the aforementioned patent applications are incorporated herein by this reference.

The invention relates to novel microbial 7α-hydroxysteroid dehydrogenase (7α-HSDH) knockout mutants, and to the use thereof for the production of other HSDHs of differing functionality, such as, for example, 3α-, 7β- or 12α-HSDH, and to the use of the HSDH enzymes thus produced in enzymatic reactions of cholic acid compounds, and in particular in the production of ursodeoxycholic acid (UDCA); the invention relates in particular to novel methods for the synthesis of UDCA.

BACKGROUND OF THE INVENTION

The active substances ursodeoxycholic acid (UDCA) and the associated diastereomer chenodeoxycholic acid (CDCA), inter alia, have been employed for many years for the medicinal treatment of gallstones. Both compounds differ only by the configuration of the hydroxyl group on the C atom 7 (UDCA: β-configuration, CDCA: α-configuration). In the prior art, various methods for the production of UDCA are described, which are carried out purely chemically or consist of a combination of chemical and enzymatic process steps. The starting point is in each case cholic acid (CA) or the CDCA produced from cholic acid.

Thus the classic chemical method for UDCA production can be represented schematically as follows:

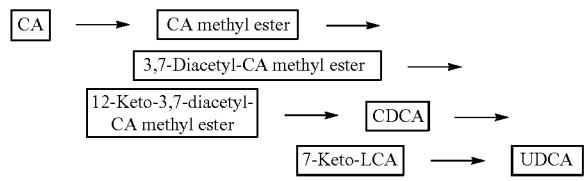

A serious disadvantage, among other things, is the following: since the chemical oxidation is not selective, the carboxyl group and the 3α and 7α-hydroxy group must be protected by esterification.

An alternative chemical/enzymatic method, based on the use of the enzyme 12α-HSDH is described, for example, in the PCT/EP2009/002190 of the present Applicant. In particular, recombinantly produced 12α-HSDH is employed here. The enzyme is preferably produced here by recombinant *E. coli* hosts, isolated therefrom and employed for reaction.

The 12α-HSDH oxidizes CA selectively to 12-keto-CDCA here. The two chemical protection steps necessary according to the classic chemical method are unnecessary here.

It is problematic in this method that the valuable product UDCA produced in this way is contaminated for reasons unknown up to now with lithocholic acid (LCA).

Novel 7β-HSDHs and use thereof in the production of UDCA in the reductive route are described in the PCT/EP2010/068576 of the Applicant. It is problematic here that the recombinant *E. coli* hosts also produce endogenous 7α-HSDH, and the 7α-HSDH produces a 3,12-diketo-CDCA by-product from dehydrocholic acid. This 3,12-diketo-CDCA is then no longer a substrate of the 7β-HSDH, so that in addition to the desired product the undesired by-product is also accumulated.

The object of the invention is therefore the provision of a novel method for the production of UDCA, which avoids the disadvantages described above. In particular, the enzymatic/chemical production of UDCA without impurities, such as LCA or 3,12-diketo-CDCA, is to be made possible.

BRIEF SUMMARY OF THE INVENTION

According to the invention, it was surprisingly discovered that the cause of the occurrence of undesired impurities, such as, for example. LCA, is not the undesired result of a complex chemical side reaction. The occurrence of LCA is also not the result of a side reaction catalyzed by 12α-HSDH itself. Rather, the 12α-HSDH enzyme catalyzing the enzymatic reaction step contains an enzymatic impurity as a result of a 7α-HSDH activity. The result of this is the oxidation of the 12-keto-CDCA to 7,12-diketo-LCA, which in the course of the further chemical conversion reactions, which lead to UDCA, is reduced to LCA in a chemical side reaction. This is shown in the following scheme.

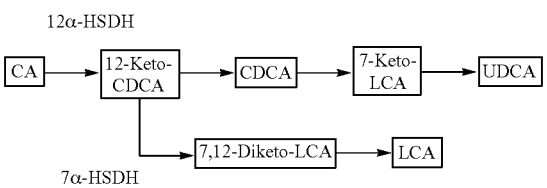

It was in particular discovered that the cause of the formation of 7, 12 deketo-LCA is the contamination of the 12α-HSDH with 7α-HSDH enzyme. In the recombinant production of 12α-HSDH (such as its short form), especially in production using *E. coli* host cells, 12α-HSDH itself is in fact contaminated with endogenous 7αHSDH-enzyme after purification. Both enzymes have very similar molecular weights and also otherwise really similar separation behavior during purification because of virtually identical sequence length (257 or 255 amino acids for 12α-HSDH (short form) or 7α-HSDH), so that the 12α-HSDH produced in this way is virtually always contaminated with 7α-HSDH.

The 7β-HSDH can also not be separated from the undesired 7α-hSDH activity without difficulty.

According to the invention, the preparation of HSDHs, such as, for example, the 12α-HSDH or the 7β-HSDH, which no longer has 7α-HSDH activity, surprisingly succeeded only by selective switching off of the secondary activity in the expression host used for recombinant production of the 12α-HSDH or other HSDHs, such as, for example, the 7β-HSDH.

Thus the expression host *E. coli* BL21(DE3) (genotype: F⁻ ompT gal dcm lon hsdS$_B$(r$_B^-$m$_B^-$) λ(DE3 [lacI lacUV5-T7 gene 1 ind1 sam7 nin5]) (Novagen) (Journal of Molecular Biology (1985) 189, 113-130) is employed to a great extent for production of recombinant proteins. *E. coli* BL21(DE3), however, contains a NADH-dependent 7α-HSDH, which, for example, causes the formation of the undesired by-product lithocholic acid in the production of UDCA, as was now discovered according to the invention.

For avoidance of the side reaction as a result of the 7α-HSDH from *E. coli* BL21(DE3) in the production of UDCA, the gene which encodes the endogenous 7α-HSDH was successfully knocked out according to the invention, for example, in a first, from *E. coli* BL21(DE3) by homologous recombination. The resulting strain *E. coli* BL21(DE3) Δ7α-HSDH allows the recombinant production of 12α-HSDH preparations, which no longer cause said undesired side reaction in the production of UDCA.

According to the invention, the synthesis of UDCA is thereby made possible, as shown in the following schematic representation, for the first time without the side reaction catalyzed by 7α-HSDH. The 12α-HSDH thus oxidizes CA selectively to 12-keto-CDCA.

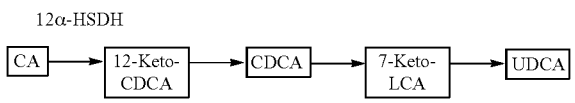

The proposed solution of the above object is thus all the more surprising, as it was discovered that the endogenous 7α-HSDH is an NADH-dependent enzyme, the recombinantly expressed 12α-HSDH, however, is NADPH dependent. The 7α-HSDH, however, also shows, as was discovered according to the invention, trace activity in the presence of NADPH and in spite of the absence of NADH. This trace activity is ultimately sufficient to contaminate the valuable product UDCA in an undesired manner with LCA, even if the enzymatic synthesis step is carried out with isolated enzyme and not with whole cells. When using whole cells, on account of the presence of cellular NADH from cells, 7α-HSDH is completely active, whereby the by-product formation would be drastically increased even further.

Thus according to the invention also the production of LCA-free UDCA according to above enzymatic/chemical synthesis route is made possible using whole recombinant cells which express 12α-HSDH-activity, but are free of interfering 7α-HSDH activity.

DESCRIPTION OF FIGURES

FIG. 2A: cholic acid with *E. coli* BL21(DE3); FIG. 2B: cholic acid with knockout mutant *E. coli* BL21(DE3) Δ7α-HSDH; FIG. 2C: cholic acid as a control. The arrow in diagram A shows an oxidation product (7-keto-3,12-dihydroxycholanic acid; retention time (RT)=7.5 min) in the transformation by *E. coli* BL21(DE3). On account of an impurity, a small peak in the region of 7-keto-3,12-dihydroxycholanic acid was also seen in the knockout strain *E. coli* BL21(DE3), but the observed peak is not greater than in the negative control (FIG. 2C).

SPECIAL EMBODIMENTS OF THE INVENTION

Figure 1:
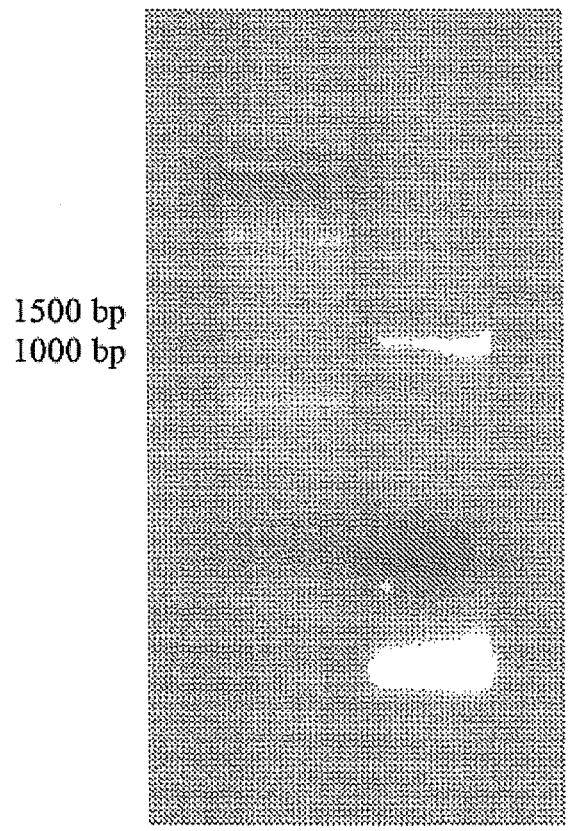
FIG. 1 shows the result of a colony PCR. In particular, a band containing 1500 bp can be seen, which corresponds to the aparemycin resistance gene integrated by recombination. The resistance is thus integrated into the genome and the gene of the 7α-HSDH was knocked out. Trace 1 shows the DNA marker. Trace 2 the PCR product containing 1500 bps.

The invention relates in particular to the following embodiments:

1. Recombinant microorganism, in which the enzymatic activity of the 7α-hydroxysteroid dehydrogenase (7α-HSDH) is inhibited, while the enzymatic activity of a functionally different hydroxysteroid dehydrogenase (such as, for example, 3α-, 3β-, 7β-, 11α-, 11β-, 12α-, 12β-, 17α-, 17β-, 20α-, or 20β-HSDH, in particular 3α-, 7β- or 12α-HSDH) is contained expressibly.

The inhibited 7α-HSDH can here show any desired cofactor dependence, such as, for example, be dependent on NADH or NADPH (or NAD⁺ or NADP⁺).

Optionally, such a modified microorganism can additionally also be modified such that it expresses not only the desired HSDH activity(ies) but also other proteins or enzymes, which can optionally out in combination with the HSDH, such as, for example, enzymes which assist cofactor regeneration (as explained in more detail below). Examples of these are enzymes such as alcohol dehydrogenases (ADH) and formate dehydrogenases (FDH).

In particular, the invention relates here to a recombinant microorganism, in which the enzymatic activity of the 7α-HSDH is inhibited, while the enzymatic activity of an exogenous 12α-HSDH is contained expressibly; such as in particular a microorganism of the type in which the endogenous enzymatic activity of the (e.g. NADH-dependent) 7α-HSDH is inhibited, while the enzymatic activity of the (e.g. NADPH-dependent) 12α-HSDH is contained expressibly. Fundamentally, 7α-HSDH and 12α-HSDH can here exhibit identical or different cofactor dependence, i.e. 7α-HSDH and 12α-HSDH can both be dependent on NADH or NADPH (or NAD⁺ or NADP⁺). 7α-HSDH and 12α-HSDH, however, can also be dependent on various cofactors; thus 7α-HSDH, for example, can be dependent on NADH (or NAD⁺) and 12α-HSDH can be dependent on NADPH (or NADP⁺) or conversely. In particular, in the case of dependence on various cofactors an analytically detectable enzyme activity can also be observed in the presence of the other cofactor in each case. Thus, for example, 7α-HSDH can be dependent on NADH (or NAD⁺), but also exhibit analytically detectable enzymatic activity in the presence of NADPH (or NADP⁺).

The above correspondingly applies if instead of the 12α-HSDH one or more other HSDHs, such as, for example, selected from 3α-, 3β-, 7β-, 11α-, 11β-, 12β-, 17α-, 17β-, 20α- and 20β-HSDH, are intended to be expressed and optionally isolated, such as, for example, a 3α- and/or 7β-HSDH.

2. Recombinant microorganism according to embodiment 1, in which the nucleic acid sequence encoding 7α-HSDH is knocked out, in particular by homologous recombination or by gene disruption (in particular by insertion of a nucleic acid sequence inhibiting the enzyme function of the encoded gene product).

3. Recombinant microorganism according to one of the preceding embodiments, derived from a precursor microorganism expressing 7α-HSDH, in particular a precursor microorganism endogenously expressing 7α-HSDH, such as bacteria of the genus *Escherichia*, especially *E. coli*.

4. Recombinant microorganism according to embodiment 3, derived from *E. coli* BL21.

5. Recombinant microorganism according to one of the preceding embodiments, which recombinantly expresses the HSDH functionally different from the 7α-HSDH, such as in particular a 3α-, 7β- and/or 12α-HSDH.

6. Recombinant microorganism according to one of the preceding embodiments, wherein the inhibited (knocked out) 7α-HSDH has an amino acid sequence according to SEQ ID NO: 10 or is encoded by a nucleic acid sequence according to SEQ ID NO: 9.

7. Recombinant microorganism according to one of the preceding embodiments, wherein the expressed HSDH functionally different from the 7α-HSDH contains one of the following amino acid sequences:
a) a 3α-HSDH sequence selected from: SEQ ID NO:29 and 31
b) a 7β-HSDH sequence selected from: SEQ ID NO: 25 and
c) a 12α-HSDH sequence selected from SEQ ID NO: 12, 14, 16; or
d) contains an amino acid sequence coding for an HSDH derived from a), b) or c), with a degree of identity of at least 50% or at least 60% or at least 75%, in particular at least 85%, such as, for example, 90, 91, 92, 93, 94, 95, 96, 97, 98 or 99%, to one of these sequences under a), b) or c).

8. Method for the recombinant production of a desired HSDH functionally different from the 7α-HSDH, such as, for example, a 3α-, 3β-, 7β-, 11α-, 11β-, 12α-, 12β-, 17α-, 17β-, 20α-, or 20β-HSDH, in particular 3α-, 7β- or 12α-HSDH, wherein a recombinant microorganism according to one of the preceding claims in which the enzymatic activity of the 7α-HSDH is inhibited is cultured under conditions under which the desired HSDH is expressed, and the HSDH thus expressed is isolated, wherein essentially no functional 7α-HSDH is detectable in the isolated HSDH In particular, the invention relates here to the production of a, in particular NADPH-dependent, 12α-HSDH, wherein a recombinant microorganism according to one, of the preceding embodiments is cultured under conditions expressing 12α-HSDH, and the expressed 12α-HSDH is isolated, wherein the isolated enzyme is not contaminated by 7α-HSDH enzyme.

In particular, the invention relates here, however, also to the production of an NADH-Or in particular NADPH-dependent 7β-HSDH, wherein a recombinant microorganism according to one of the preceding embodiments is cultured under conditions expressing 7β-HSDH, and the expressed 7β-HSDH is isolated, wherein the isolated enzyme is not contaminated by 7α-HSDH enzyme.

9. Recombinant HSDH, such as, for example, 3α-, 3β-, 7β-, 11α-, 11β-, 12α-, 12β-, 17α-, 17β-, 20α-, or 20β-HSDH, in particular 3α-, 7β- or 12α-HSDH, in particular NADPH-dependent 7β-HSDH or 12α-HSDH, which is not contaminated by 7α-HSDH enzyme or enzyme activity, in particular not by NADPH-dependent 7α-HSDH or NADH-dependent 7α-HSDH with NADPH-dependent secondary activity, obtainable from a recombinant microorganism according to one of the embodiments 1 to 7.

10. Recombinant HSDH, such as, for example, 3α-, 3β-, 7β-, 11α-, 11β-, 12α-, 12β-, 17α-, 17β-, 20α-, or 20β-HSDH, in particular 3α-, 7β- or 12α-HSDH according to embodiment 9, comprising an amino acid sequence, selected from SEQ ID NOs according to embodiment 6 and amino acid sequences derived therefrom with a degree of identity of at least 50% or at least 60% or at least 75%, in particular at least 85%, such as, for example, 90, 91, 92, 93, 94, 95, 96, 97, 98 or 99%, to one of these sequences.

11. Method for the selective enzymatic oxidation of hydroxysteroids which in addition to a hydroxyl group in at least one of the positions 3α-, 3β-, 11α-, 11β-, 12α-, 12β-, 17α-, 17α-, 20α-, or 20β- of the steroid structure, in particular in the 12α-position of the steroid structure, contain at least one further hydroxyl group in the 7α-position of the steroid structure, wherein the hydroxysteroid is reacted in the presence of a 3α-, 3β-, 11α-, 11β-, 12α-, 12β-, 17α-, 17α-, 20α-, or 20β-HSDH, in particular of a 12α-HSDH according to embodiment 9 or 10 or in the presence of a recombinant microorganism according to one of the embodiments 1 to 7, and at least one oxidation product formed is optionally isolated from the reaction batch.

12. Method according to embodiment 11, wherein the hydroxysteroid is cholic acid (CA) or a cholic acid derivative, such as, in particular, a salt, amide or alkyl ester.

13. Method according to embodiment 12, wherein CA or a derivative thereof is reacted to give 12-ketochenodeoxycholic acid (12-keto-CDCA) or to give the corresponding derivative.

14. Method according to one of the embodiments 11 to 13, wherein the reaction takes place in the presence of $NAD(P)^+$.

15. Method according to one of the embodiments 14, wherein the $NAD(P)^+$ consumed are regenerated electrochemically or enzymatically.

16. Method for the production of ursodeoxycholic acid (UDCA) of the formula (1)

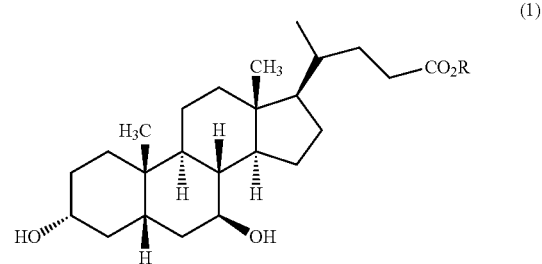

in which
R represents alkyl, $NR^1R^2$, H, an alkali metal ion or $N(R^3)_4^+$, in which the radicals $R^3$ are identical or different and represent H or alkyl,
wherein
a) a cholic acid (CA) of the formula (2)

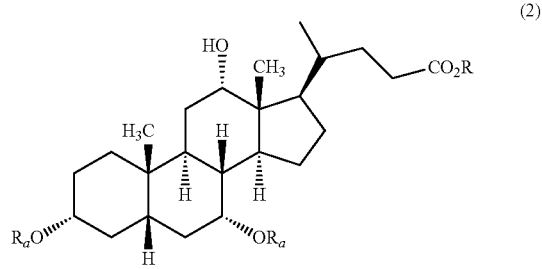

in which R have the meanings indicated above, and the radicals R, are identical or different and represent H or acyl, in the presence of a 12α-HSDH according to embodiment 9 or 10 or in the presence of a recombinant microorganism according to one of the embodiments 1 to 7 is oxidized to the corresponding 12-ketochenodeoxycholic acid (12-keto CDCA) of the formula (3)

(3)

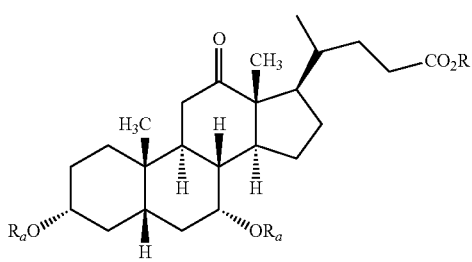

in which R and $R_a$ have the meanings indicated above, and subsequently
b) 12-keto-CDCA of the formula (3) is reacted by deoxygenation to give chenodeoxycholic acid (CDCA) of the formula (4)

(4)

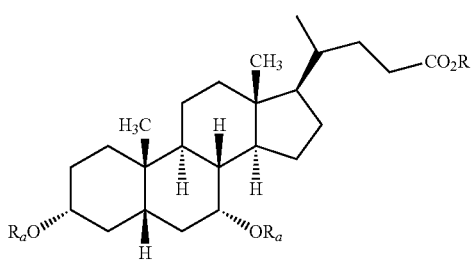

in which R and $R_a$ have the meanings indicated above, and
c) CDCA of the formula (4) is chemically oxidized in position 7 to the 7-ketolithocholic acid (KLCA) of the formula (5)

(5)

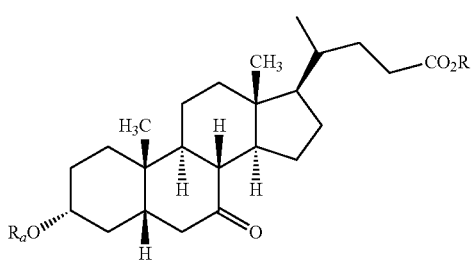

in which R and $R_a$ have the meanings indicated above; and
d) KLCA of the formula (5) is reduced and
e) the reaction product is optionally further purified.

17. Method according to embodiment 16, wherein if $R_a$ represents acyl, this acyl group is optionally removed after carrying out the reaction step b) or d).

18. Method according to embodiment 16 or 17, wherein step a) takes place in the presence of $NAD(P)^+$.

19. Method according to embodiment 18, wherein NAD$(P)^+$ consumed are regenerated electrochemically or enzymatically.

20. Method for the selective enzymatic reduction of ketosteroids, which in addition to at least one keto group in position 3, 11, 12, 17, or 20 of the steroid structure, in particular in position 12 and/or position 3 of the steroid structure have at least one further keto group in position 7 of the steroid structure, wherein the ketosteroid is reacted in the presence of a 3α-, 3β-, 7α-, 11α-, 11β-, 12α-, 12β-, 17α-, 17β-, 20α-, or 20β-HSDH, in particular of a 7β-HSDH and/or of a 3α-HSDH and/or of a 12α-HSDH according to embodiment 9 or 10, or in the presence of a recombinant microorganism according to one of the embodiments 1 to 7, and at least one reduction product formed is optionally isolated from the reaction batch.

21. Method for the production of ursodeoxycholic acid (UDCA) of the formula (1)

(1)

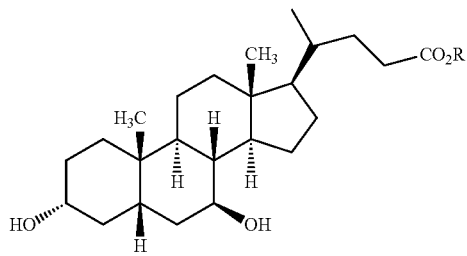

in which
R represents alkyl, $NR^1R^2$, H, an alkali metal ion or $N(R^3)_4^+$, in which the radicals $R^3$ are identical or different and represent H or alkyl, wherein
a) optionally a cholic acid (CA) of the formula (2)

(2)

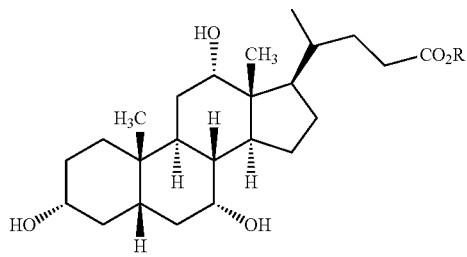

in which R has the meanings indicated above is chemically oxidized to the dehydrocholic acid (DHCA) of the formula (3)

(3)

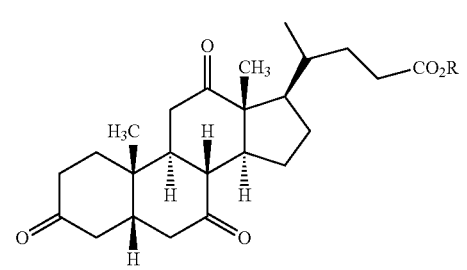

in which R has the meanings indicated above;
b) DHCA is reduced with a 7β-HSDH and a 3α-HSDH according to one of the embodiments 9 or 10 in any desired sequence or in the simultaneous presence of both enzymes to the corresponding 12-ketoursodeoxycholic acid (12-keto UDCA) of the formula (5)

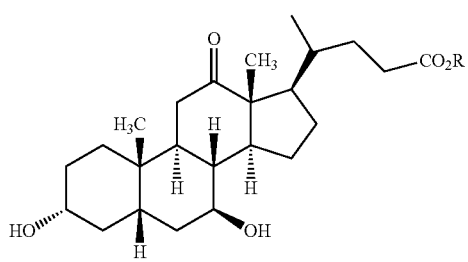

(5)

in which R has the meanings indicated above, and subsequently d) 12-keto-UDCA of the formula (5) is reduced chemically to UDCA; and e) the reaction product is optionally further purified.

22. Method according to one of the embodiments 11 to 22, wherein the enzymatic redox step(s) is (are) coupled with a (in particular enzymatic) cofactor regeneration step.

23. Method according to one of the embodiments 11 to 22, wherein the HSDHs is employed in dissolved, dispersed or immobilized form; or wherein the method is carried out in the presence of whole, optionally immobilized cells of a recombinant microorganism according to one of the embodiments 1 to 7.

FURTHER EMBODIMENTS OF THE INVENTION

1. General Definitions and Abbreviations Used

The position particulars used herein relating to substituents of the steroid structure are given in agreement with the following nomenclature:

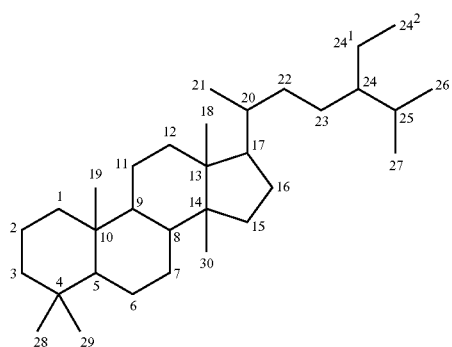

In the following table, the structural formulae, chemical names thereof and the abbreviations used are summarized in tabular form:

| Formula | Abbreviation | Chemical name |
|---|---|---|
| ![Cholic acid structure] Cholic acid | CA | Cholic acid |
| ![12-Ketochenodeoxycholic acid structure] 12-Ketochenodeoxycholic acid | 12-Keto-CDCA | 12-Keto-chenodeoxycholic acid |

-continued
| Formula | Abbreviation | Chemical name |
|---|---|---|
| 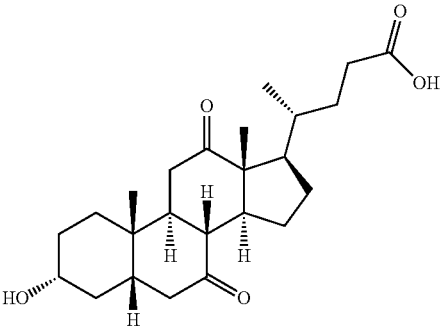 7,12-Diketolithocholic acid | 7,12-Diketo-LCA | 7,12-Diketolithocholic acid |
| 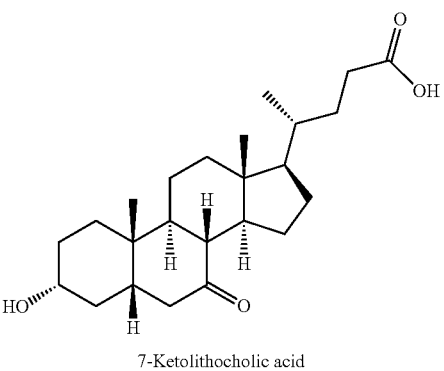 7-Ketolithocholic acid | 7-Keto-LCA (KLCA) | 7-Ketolithocholic acid |
| 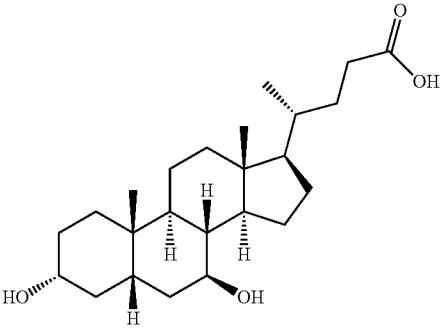 Ursodeoxycholic acid | UDCA | Ursodeoxycholic acid |
| 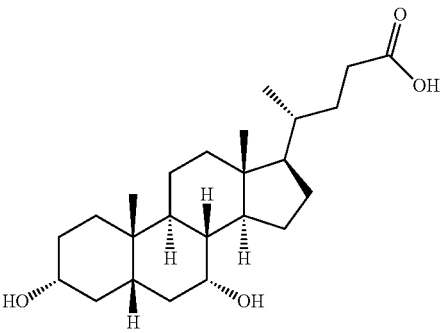 Chenodeoxycholic acid | CDCA | Chenodeoxycholic acid |

| Formula | Abbreviation | Chemical name |
|---|---|---|
| 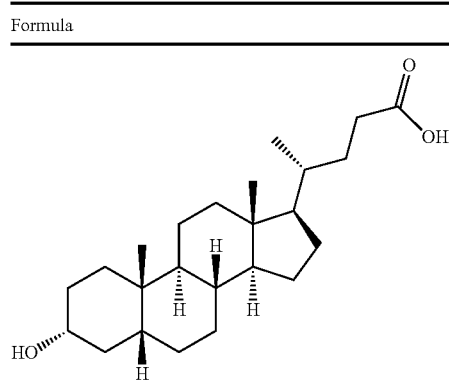 | LCA | Lithocholic acid |
| Lithocholic acid | | |

"Knockout" mutants (or knockout strains) of an organism for a certain gene (such as, for example, 7α-HSDH gene) are understood in the context of the present invention as meaning mutants of the organism in which the gene concerned is "inactivated" at the DNA level. Such an inactivation is to be understood in the widest sense and can be based, for example, on a complete deletion of the nucleic acid sequence of the appropriate structural gene, such that no protein is translated, or partial deletion thereof, such that an incomplete protein is thus encoded and translated, the function of which in comparison to the protein, which is encoded by the original structural gene, is restricted, in particular is completely suppressed. Furthermore, the structural gene can be knocked out by "nonsense mutations" known to the person skilled in the art, in which the nucleic acid sequence of the structural gene is modified to the effect that one or more premature stop codons occur in the reading frame and significant parts of the protein are not translated. Alternatively, "missense mutations" can be introduced, in which individual or multiple amino acids essential for the function (for example, amino acids that are responsible in enzymes for the substrate binding, the catalytic center or reallosteric regions, or amino acids that are responsible for the binding or interaction with other proteins or molecules) are removed or replaced by amino acid, which lead to a partial or complete loss of the function concerned. Furthermore, the insertion of one or more nucleotides can be performed, which lead to a shift of the reading frame (frameshift) and thus to expression of a protein with restricted function, and in particular in occurrence of the frameshift close to the N-terminus to a complete functional loss. Also the insertion of nucleic acid sequences that code for individual proteins (marker proteins) (for example proteins that lead to antibiotic resistance) into the structural gene of the protein that is to be knocked out can be used and used in expression of the inserted nucleic acid sequence as a phenotypic detection for a successful knocking out. Knockout mutants can also be produced by the aforementioned measures of the complete or partial deletion or insertion of nucleic acids in regulatory regions, that are necessary for the expression of the structural gene concerned, for example the promoters or enhancer of the structural gene. In particular, the knocking out, however, takes place by partial or complete deletion of the structural gene, by insertion of a transcribable nucleic acid sequence for a marker protein in the nucleic acid sequence of the structural gene to be knocked out, or a combination of both methods. If a number of copies of the gene concerned or homologs of this, which can fulfill the function of the gene concerned, are present in an organism or a cell, for example a number of genes on a bacterial chromosome, on a bacterial chromosome and simultaneously on extrachromosomal elements such as plasmids within a prokaryotic cell, or at different points of a eukaryotic chromosome or on various eukaryotic chromosomes, optionally additionally on extrachrosomal DNA in a eukaryotic cell, a number, preferably all of the copies or homologs of the gene concerned can thus be knocked out.

"Endogenous" is to be understood as meaning genetic information, such as, for example, genes, that are already contained in the wild-type genome (as defined herein).

"Exogenous" is to be understood as meaning genetic information, such as, for example, genes, that are not contained in the wild-type genome. If exogenous genetic information, for example the 12α-HSDH-containing expression units according to the invention, is introduced into the genome of a wild-type strain and thereby a genetically modified strain is produced, this genetic information is thus endogenous in the comparison of the genetic strain produced for the first time with its descendants, but exogenous in the comparison with the original wild-type strain, which did not contain this genetic information.

The term "wild type" is to be understood according to the invention as meaning the corresponding starting organism and does not necessarily have to correspond to a naturally occurring organism.

Depending on relationship, the term "microorganism" can be understood as meaning the starting microorganism (wild-type) or a genetically modified microorganism according to the invention or both.

An encoding sequence is "expressibly" contained in an organism, if it is either translated permanently or restricted in terms of time (for example after induction) into the corresponding protein product.

"Inhibition" within the meaning of the invention comprises a partial or complete inhibition of a biological function. It is in particular present according to the invention, if a biological function no longer desired for certain reasons, such as, for example, enzyme activity, is no longer analytically detectable, such as, for example, the enzymatic activity of the 7α-HSDH.

If no other details are given, the term "7α-HSDH" thus designates a dehydrogenase enzyme, which catalyzes at least the stereospecific and/or regiospecific oxidation of 12-keto-CDCA to 7,12-diketo-LCA with stoichiometric consumption of NAD(P), in particular NAD. Such enzymes are also compiled under the EC number 1.1.1.159. 7α-HSDHs are in particular to be found in organisms of the intestinal flora, such as, for example, Clostridia, such as, for example. *Clostridium absonum, Clostridium sordellii* (Journal of Bacteriology, 1994, 4865-4874), in *Escherichia coli* (Journal of Bacteriology 1991, 2173-2179), in *Bacteroides fragilis* (Current Microbiology, 2003, 47, 475-484), and in *Brucella, Eubacterium*. The invention is thus fundamentally applicable to all these microorganisms.

If no other details are given, the term "12α-HSDH" thus designates a dehydrogenase enzyme, which catalyzes at least the stereospecific and/or regiospecific oxidation of cholic acid (CA) to 12-ketochenodeoxycholic acid (12-keto-CDCA) with stoichiometric consumption of $NAD^+$ or $NADP^+$. Such enzymes are also compiled under the EC number 1.1.1.176. Both $NADP^+$-dependent (Harris and Hylemon (1978) *Biochim Biophys Acta* 528(1): 148-57), as well as $NAD^+$-dependent representatives (Macdonald et al. 1976) *Biochim Biophys Acta* 450(2): 142-53 exist. The only known microorganism that expresses a high 12α-HSDH activity in the absence of other HSDH is *Clostridium* sp. group P strain 48-50 DSM 4029. Particularly suitable 12α-HSDHs and mutants/variants of these are in particular described in the PCT/EP2009/002190 of the present Applicant, to which reference is expressly made.

If no other details are given, the term "7β-HSDH" thus designates a dehydrogenase enzyme which catalyzes at least the stereospecific and/or regiospecific reduction of DHCA to 3,12-diketo-7β-CA in particular with stoichiometric consumption of NADPH, and optionally the corresponding reverse reaction. The enzyme can be a native or recombinantly produced enzyme here. The enzyme can fundamentally be present in a mixture with cellular, such as, for example, protein impurities, but preferably in pure form. Suitable detection methods are, for example, described in the following section or known from the literature (for example, *Characterization of NADP-Dependent 7 β-hydroxysteroid Dehydrogenases from Peptostreptococcus productus and Eubacterium aerofaciens*. S Hirano and N Masuda. Appl Environ Microbiol. 1982; wherein, however, there no 7β-HSDH from *Eubacterium aerofaciens* could be detected, which the reduction of 7-keto groups makes possible). Enzymes of this activity are classified under the EC Number 1.1.1.201.

If no other details are given, the term "3α-HSDH" thus designates a dehydrogenase enzyme, which catalyzes at least the stereospecific and/or regiospecific reduction of 13,2-diketo-7β-CA to 12-keto-UDCA, in particular with stoichiometric consumption of NADH and/or NADPH, and optionally the corresponding reversal reaction. Suitable detection methods are described, for example, in the following experimental section or are known from the literature. Suitable enzymes are obtainable, for example, from *Comanomonas testosteroni* (for example, ATCC11996). An NADPH dependent 3α-HSDH is known, for example, from rodents and likewise employable. (Cloning and sequencing of the cDNA for rat liver 3 alpha-hydroxysteroid/dihydrodiol dehydrogenase, J E Pawlowski, M Huizing a and T M Penning, May 15, 1991 The Journal of Biological Chemistry, 266, 8820-8825). Enzymes of this activity are classified under the EC Number 1.1.1.50.

A "pure form" or a "pure" or "essentially pure" enzyme is understood according to the invention as meaning an enzyme with a degree of purity of more than 80, preferably more than 90, in particular more than 95, and especially more than 99% by weight, based on the total protein content, determined with the aid of customary protein detection methods, such as, for example, the biuret method or the protein detection according to Lowry et al. (cf. description in R. K. Scopes, Protein Purification, Springer Verlag, New York, Heidelberg, Berlin (1982)).

A "redox equivalent" is understood as meaning a low molecular weight organic compound usable as an electron donor or electron acceptor, such as, for example, nicotinamide derivatives such as $NAD^+$ and $NADH^+$ or their reduced forms tNADH or NADPH. $NAD(P)^+$ stands here for $NAD^+$ and/or $NADP^+$ and NAD(P)H stands here for NADH and/or NADPH. These are also designated as "cofactors".

A "cholic acid compound" is understood according to the invention as meaning compounds having the carbon skeleton, in particular the steroid structure of cholic acid and the presence of keto and/or hydroxy or acyloxy groups in the ring position 7 and optionally the ring positions 3 and/or 12.

A compound of a special type, such as, for example, a "cholic acid compound" or an "ursodeoxycholic acid compound" is understood in particular as also meaning derivatives of the basic starting compound (such as, for example, cholic acid or ursodeoxycholic acid).

Such derivatives comprise "salts", such as, for example, alkali metal salts such as lithium, sodium and potassium salts of the compounds; and ammonium salts, wherein an ammonium salt comprises the $NH_4^+$ salt or those ammonium salts in which at least one hydrogen atom can be replaced by a $C_1$-$C_6$-alkyl radical. Typical alkyl radicals are in particular $C_1$-$C_4$-alkyl radicals, such as methyl, ethyl, n- or i-propy, n-, sec- or tert-butyl, and n-pentyl and n-hexyl and the simply or multi-branched analogs thereof.

"Alkyl esters" of compounds according to the invention are in particular lower alkyl esters, such as, for example, $C_1$-$C_6$-alkyl esters. Non-limiting examples that may be mentioned are methyl, ethyl, n- or i-propyl, n-, sec- or tert-butyl esters, or longer chain esters, such as, for example, n-pentyl and n-hexyl esters and the simply or multi-branched analogs thereof.

"Amides" are in particular reaction products of acids according to the invention with ammonia or primary or secondary monoamines. Such amines are, for example, mono- or di-$C_1$-$C_6$-alkyl-monoamines, wherein the alkyl radicals independently of one another can optionally be further substituted, such as, for example, by carboxyl, hydroxyl, halogen (such as F, Cl, Br, I), nitro and sulfonate groups.

"Acyl groups" according to the invention are in particular nonaromatic groups having 2 to 4 carbon atoms, such as, for example, acetyl, propionyl and butyryl, and aromatic groups with an optionally substituted mononuclear aromatic ring, wherein suitable substituents, for example, are selected from hydroxyl, halogen (such as F, Cl, Br, I), nitro and $C_1$-$C_6$-alkyl groups, such as, for example, benzoyl or toluoyl.

The hydroxysteroid compounds employed or produced according to the invention, such as, for example, cholic acid, ursodeoxycholic acid, 12-ketochenodeoxycholic acid, chenodeoxycholic acid and 7-ketolithocholic acid can be employed in stereoisomerically pure form or in the mixture with other stereoisomers in the method according to the invention or obtained therefrom. Preferably, however, the employed or the produced compounds are employed or isolated in essentially stereoisomerically pure form.

An "immobilization" is understood according to the invention as meaning the covalent or non-covalent binding of a biocatalyst used according to the invention, such as, for example, a 7β-HSDH to a solid, i.e. in the surrounding liquid medium essentially insoluble, carrier material.

2. Proteins, in Particular Recombinant Enzymes that can be Produced According to the Invention

2.1 12α-HSDHs

Such 12α-HSDHs are described in particular in WO 2009/118176 of the Applicant.

According to the invention, expressed 12α-HSDHs are obtainable in particular from *Clostridium* sp. and have a molecular weight, determined by SDS polyacrylamide gel electrophoresis (SDS PAGE) under reducing conditions in the region of more than approximately 26 kD, in particular more than approximately 26.5, such as approximately 27 to 30 kD. They have in particular a calculated molecular weight of more than approximately 29 kD, in particular approximately 29.1 to 29.5 kD, such as in particular 29.359 kD for 12α-HSDH long version or approximately 27.8 for 12α-HSDH short version. The molecular weight details relate here to the molecular weight of the protein subunits of the enzyme; without being restricted thereto, the native protein consists, for example, of 4, in particular approximately identically sized, such subunits.

In particular, such a protein is obtainable from *Clostridium* sp. group P strain 48-50 (DSM4029). The enzyme can be prepared, for example, in a specific activity in the range from more than approximately 10, 15, 20 or 25 U/mg, such as, for example, 20 to 100 U/mg or 25 to 80 U/mg. The determination of the specific activity is carried out here under the standard conditions indicated in the experimental section.

According to the invention, in particular 12α-HSDHs, comprising at least one of the following amino acid sequence motifs are used:
a) LINN (SEQ ID NO; 39)
b) RMGIFD (SEQ ID NO: 40)
c) N-terminal sequence, selected from
(1) MDFIDFKEMGRMGIFDGKVAI-ITGGGKAKSIGYGIAVAYAK (SEQ ID NO: 41)
(2) MDFIDFKEMGRMGI (SEQ ID NO: 42)
(3) ITGGGKAKSIGYGIA (SEQ ID NO: 43)
(4) IFDGK (SEQ ID NO: 44)
(5) GIFDGK (SEQ ID NO: 45)
d) FGDPELDI (SEQ ID NO: 46) or sequences derived therefrom, such as, for example: GDPELDI (SEQ ID NO: 47), FGDPELD (SEQ ID NO: 48), DPELDI (SEQ ID NO: 49), FGDPEL (SEQ ID NO: 50), GDPEL (SEQ ID NO: 51), DPELD (SEQ ID NO: 52), GDPELD (SEQ ID NO: 53).

Furthermore, the 12α-HSDH enzymes used according to the invention are characterized in that they contain no N-terminal, (i.e. in the region of the N-terminal end of approximately 1 to 30 amino acid radicals) sequence motif of the type $TGX_3GXG$, in which X represents any desired amino acid radicals.

In particular, 12α-HSDHs are also used,
a) comprising one of the amino acid sequences according to SEQ ID NO: 12, 14 or 16, in each case beginning in position +1 or +2; or
b) comprising an amino acid sequence derived from a sequence according to a) with a percentage sequence identity of at least 60%; or
c) encoded by a nucleic acid sequence encoding a protein according to a) and b); or
d) encoded by an encoding nucleic acid sequence according to SEQ ID NO: 11, 13 or 15; or by a sequence derived therefrom, adapted to the respective codon use of an organism used for expression; or
e) encoded by an encoding sequence derived from one of the nucleic acid sequences according to SEQ ID NO: 11, 13 or 15; with a percentage sequence identity of at least 60%.

The adaptation of the nucleic acid sequence to the codon use can take place here according to customary methods, such as, for example, those that can be found on the worldwide web.

12α-HSDH mutants with modified cosubstrate use and/or decreased product inhibition can also be used; and in particular those mutants derived from a 12α-hydroxysteroid dehydrogenase according to the above definition, with at least one mutation modifying the cosubstrate use in the sequence motif VLTGRNE. Non-limiting examples of such mutants comprise those having at least one of the following amino acid substitutions in this motif: G→D; R→A; and mutants with at least one mutation reducing the product inhibition in the region of the amino acid radicals forming the substrate binding pocket of the enzyme; such as, for example, comprising at least the mutation of amino acid Q, corresponding to position 98 or 100 of SEQ ID NO:16; in particular comprising a mutation corresponding to Q98H in SEQ ID NO: 16.

Further potential amino acid substituents in position 98 (based on SEQ ID NO: 16) comprise: A, N, D, C, E, G, H, M, S, T, V. Based on the homology model of the 12α-HSDH-HSDH according to the invention, it is assumed that here a substitution leads to a weakening of the carboxyl binding of the product. Therefore the neighboring position S100 (based on SEQ ID NO:16) was also mutated to the following amino acids: A, N, D, C, Q, E, G, H, M, T, V, K.

A group of 12α-HSDH mutants according to the invention thus comprises one or two mutations in position 98 or 100 (according to SEQ ID NO:16) selected from:
Q→A, N, D, C, E, G, H, M, S, T, V;
S→A, N, D, C, Q, E, G, H, M, T, V, K.

2.2 7β-HSDHs

Such 7β-HSDHs are described in particular in the PCT/EP2010/068576 of the Applicant, such as in particular:

7β-HSDHs obtainable from an anaerobic bacterium, in particular of the genus *Collinsella*, such as the strain *Collinsella aerofaciens* DSM 3979 (ATCC 25986), in particular comprising an amino acid sequence according to SEQ ID NO:25 and functional equivalents derived therefrom.

The 7β-HSDH obtainable from *Collinsella aerofaciens* DSM 3979 is in particular characterized by at least another of the following properties, such as, for example, 2, 3, 4, 5, 6 or 7 or all such properties:
a) molecular weight (SDS gel electrophoresis): approximately 28-32 kDa, in particular approximately 29 to 31 kDa or approximately 30 kDa;
b) molecular weight (gel filtration, under non-denaturing conditions, such as, in particular, without SDS): approximately 53 to 60 kDa, in particular approximately 55 to 57 kDa, such as 56.1 kDa, whereby the enzyme according to the invention clearly differs from the 7β-HSDH enzyme from *C. aerofaciens* ATCC25986 described by Hirano et al (see above) of 45 kDa. This confirms the dimeric nature (quaternary structure) of the 7β-HSDH from *Collinsella aerofaciens* DSM 3979;
c) stereoselective reduction of the 7-carbonyl group of 7-keto-LCA to a 7β-hydroxy group;
d) pH optimum for the oxidation of UDCA in the range from pH 8.5 to 10.5, in particular 9 to 10;
e) pH optimum for the reduction of DHCA and 7-keto-LCA in the range from pH 3.5 to 6.5, in particular at pH 4 to 6, whereby surprisingly the possibility given is to influence oxidative (feature d)) and reductive processes by choice of the pH;

f) at least one kinetic parameter from following table for at least one of the substrates/cofactors mentioned there; in the range from ±20%, in particular ±10%, ±5%, ±3%±2% or ±1% around the value actually mentioned in the following table in each case.

| | $K_M$ (µM) | $V_{max}$ (U/mg protein)[b] | $k_{cat}$ (1 µmol/(µmol × min)) |
|---|---|---|---|
| NADP[+c)] | 5.32 | 30.58 | 944.95 |
| NADPH[c)] | 4.50 | 33.44 | 1033.44 |
| UDCA | 6.23 | 38.17 | 1179.39 |
| 7-keto-LCA | 5.20 | 30.77 | 950.77 |
| DHCA | 9.23 | 28.33 | 875.35 |
| NAD[+] | —[a)] | — | Traces |
| NADH | — | — | Traces |

[a)] could not be determined on account of the very low activity
[b)] 1 U = 1 µmol/min
[c)] whereby the enzyme according to the invention clearly differs from the 7β-HSDH enzyme from *C. aerofaciens* ATCC25986 described by Hirano et al (see above), for which clearly lower $K_M$ and $V_{max}$ values (0.4 and 0.2) was described and no activity was measured for NADPH.

g) Phylogenetic sequence relationship of the prokaryotic 7β-HSDH from *Collinsella aerofaciens* DSM 3979 related with the animal 11β-HSDH subgroup, comprising *Cavia porcellus*, *Homo sapiens* and *Mus musculus*.

For example, a 7β-HSDH according to the invention shows the following properties or combinations of properties; a); b); a) and b); a) and/or b) and c); a) and/or b) and c) and d); a) and/or b) and c) and d) and e); a) and/or b) and c) and d) and e) and f).

Such 7β-HSDHs catalyze the stereospecific reduction (hydrogenation) of a 7-ketosteroid to the corresponding 7β-hydroxysteroid, and/or the regiospecific hydrogenation (reduction) of a ketosteroid comprising a keto group in 7-position and at least one further keto group on the steroid structure to the corresponding 7β-hydroxysteroid, such as in particular of dehydrocholic acid (DHCA) in 7-position to the corresponding 3,12-diketo-7β-cholanic acid, and are, for example. NADPH dependent.

Suitable 7β-HSDHs have an amino acid sequence according to SEQ ID NO:25 (Accession NO: ZP_01773061) or a sequence derived therefrom with a degree of identity of at least 60%, such as, for example, at least 65, 70, 75, 80, 85, or 90, such as, for example, at least 91, 92, 93, 94, 95, 96, 97, 98, 99 or 99.5% to this sequence; optionally additionally characterized by one of the following properties or combinations of properties; a); b); a) and b); a) and/or b) and c); a) and/or b) and c) and d); a) and/or b) and c) and d) and e); a) and/or b) and c) and d) and e) and f) according to the above definition.

2.3 Other Proteins

In a corresponding manner, the following can be prepared using a 7α-HSDH-inhibited microorganism according to the invention, for example:

a 3α-HSDH, such as, for example, known from *Pseudomonas testosteroni* (J. Biol. Chem. 276 (13), 9961-9970 (2001)); (SEQ ID NO: 28, 29) or *Rattus norvegicus* (SEQ ID NO: 30,31);

a 3β-HSDH, such as, for example, known from *Clostridium innocuum* (Applied and Environmental Microbiology, June 1989, p. 1656-1659) or from *Pseudomonas testosteroni;* a 20β-HSDH, such as, for example, known from organisms of the group *Streptomyces* (The Journal of Biological Chemistry, 1977, Vol 252 No 1, January 10, 205-211);

a 20α-HSDH, such as known, for example, from *Clostridia*, in particular from *Clostridium scindens* (Journal of Bacteriology, June 1989, p. 2925-2932), and from *Tetrahymena pyriformis* (Biochem. J. (1994) 297, 195-200);

a 17β-HSDH, such as known from fungi such as *Cylindrocarpon radicola* (J. Biochemistry 103, 1988, 1039-1044) and *Cochliobolus lunatus* (J. Steroid Biochem. Molec. Biol. Vol 59, 1996, No. 2, p. 205-214), from bacteria of the family *Streptomyces* (Hoppe-Seyler's Z. Physiol. Chem., Vol. 356, 1975, 1843-1852), *Pseudomonas* (The Journal of Biological Chemistry, Vol. 252 No. II, Jun. 10, 1977, p. 3775-3783) and *Alcaligenes* (The Journal of Biological Chemistry, Vol. 260, No. 25, Nov. 5, 1985, p. 13648-13655);

a 17α-HSDH, such as known from *Eubacterium* sp. (Journal of Lipid Research, Vol. 35, 1994, p. 922-929);

or a 11β-HSDH, such as known from higher mammals.

2.4 Functional Equivalents

The present invention is not restricted to the actually disclosed proteins or enzymes with HSDH activity, such as, for example, 3α-, 3β-, 7β-, 11α-, 11β-, 12α-, 12β-, 17α-, 17α-, 20α-, or 20β-HSDH, in particular 3α-, 7β- or 12α-HSDH activity, but on the contrary also extends to functional equivalents thereof.

"Functional equivalents" or analogs of the enzymes actually disclosed in the context of the present invention are polypeptides different therefrom, which furthermore have the desired biological activity, such as, for example, 7β- or 12α-HSDH activity.

Thus, for example, "functional equivalents" are understood as meaning enzymes that in the test used for HSDH activity, such as 7β- or 12α-HSDH activity, have an activity of an enzyme higher or lower by at least 1%, such as, for example, at least 10% or 20%, such as, for example, at least 50% or 75% or 90%, comprising an amino acid sequence defined herein. Functional equivalents are moreover preferably stable between pH 4 and 11 and advantageously have a pH optimum in a range from pH 6 to 10, such as in particular 8.5 to 9.5, and a temperature optimum in the range from 15° C. to 80° C. or 20° C. to 70° C., such as, for example, approximately 45 to 60° C. or approximately 50 to 55° C.

The HSDH activity, such as 7β- or 12α-HSDH activity can be detected with the aid of various known tests. Without being restricted thereto, a test using a reference substrate, such as, for example, cholic acid, under standardized conditions such as defined in the experimental section, may be mentioned.

"Functional equivalents" is understood according to the invention as in particular also meaning "mutants", which in at least one sequence position of the abovementioned amino acid sequences have a different amino acid than that actually mentioned but nonetheless one of the abovementioned biological activities. "Functional equivalents" thus comprise the mutants obtainable by one or more amino acid additions, substitutions, deletions and/or inversions, wherein the changes mentioned can occur in any sequence position, as long as they lead to a mutant with the property profile according to the invention. Functional equivalence is in particular also then afforded if the reactivity patterns between mutant and unchanged polypeptide agree qualitatively, i.e., for example, identical substrates are converted at a different rate. Examples of suitable amino acid substitutions are compiled in the following table:

| Original radical | Examples of the substitution |
|---|---|
| Ala | Ser |
| Arg | Lys |

| Original radical | Examples of the substitution |
| --- | --- |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described and "functional derivatives" and "salts" of the polypeptides.

"Precursors" here are natural or synthetic precursors of the polypeptides with or without the desired biological activity.

The expression "salts" is understood as meaning both salts of carboxyl groups as well as acid addition salts of amino groups of the protein molecules according to the invention. Salts of carboxyl groups can be prepared in a manner known per se and comprise inorganic salts, such as, for example, sodium, calcium, ammonium, iron and zinc salts, and salts with organic bases, such as, for example, amines, such as triethanolamine, arginine, lysine, piperidine and the like. Acid addition salts, such as, for example, salts with mineral acids, such as hydrochloric acid or sulfuric acid and salts with organic acids, such as acetic acid and oxalic acid are likewise the subject of the invention.

"Functional derivatives" of polypeptides according to the invention can likewise be prepared on functional amino acid side groups or on the N- or C-terminal end thereof with the aid of known techniques. Such derivatives comprise, for example, aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

"Functional equivalents" of course also comprise polypeptides which are accessible from other organisms, and naturally occurring variants. For example, areas of homologous sequence regions can be determined by sequence comparison and equivalent enzymes can be ascertained in accordance with the actual specifications of the invention.

"Functional equivalents" likewise comprise fragments, preferably individual domains or sequence motifs, of the polypeptides according to the invention, which, for example, have the desired biological function.

"Functional equivalents" are moreover fusion proteins, which contain one of the abovementioned polypeptide sequences or functional equivalents derived therefrom and at least one further, functionally different therefrom, heterologous sequence in functional N- or C-terminal linkage (i.e. without mutual significant functional impairment of the fusion protein parts). Non-limiting examples of such heterologous sequences are, for example, signal peptides, histidine anchors or enzymes.

According to the invention, included "functional equivalents" are homologs to the proteins actually disclosed. These have at least 60%, preferably at least 75% in particular at least 85%, such as, for example, 90, 91, 92, 93, 94, 95, 96, 97, 98 or 99%, homology (or identity) to one of the amino acid sequences actually disclosed, calculated according to the algorithm of Pearson and Lipman, Proc. Natl. Acad, Sci. (USA) 85(8), 1988, 2444-2448. A percentage homology or identity of a homologous polypeptide according to the invention in particular means percentage identity of the amino acid radicals based on the total length of one of the amino acid sequences actually described herein.

The percentage identity values can also be determined by means of BLAST alignments, algorithm blastp (protein-protein BLAST), or by use of the Clustal settings indicated below.

In the case of a possible protein glycosylation "functional equivalents" according to the invention comprise proteins of the type described above in deglycosylated or glycosylated form and modified forms obtainable by variation of the glycosylation pattern.

Homologs of the proteins or polypeptides according to the invention can be produced by mutagenesis, for example, by point mutation, elongation or truncation of the protein.

Homologs of the proteins according to the invention can be identified by screening of combinatorial banks of mutants, such as, for example, truncation mutants. For example, a variegated bank of protein variants can be produced by combinatorial mutagenesis at the nucleic acid level, such as, for example, by enzymatic ligation of a mixture of synthetic oligonucleotides. There are a multiplicity of methods that can be used for production of banks of potential homologs from a degenerated oligonucleotide sequence. The chemical synthesis of a degenerated gene sequence can be carried out in a DNA synthesizer, and the synthetic gene can then be ligated into a suitable expression vector. The use of a degenerated set of genes enables the preparation of all sequences in a mixture, that encode the desired set of potential protein sequences. Methods for the synthesis of degenerated oligonucleotides are known to the person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, a plurality of techniques for the screening of gene products of combinatorial banks, that have been produced by point mutations or truncation, and for the screening of cDNA banks for gene products with a selected property are known. These techniques can be adapted to the rapid screening of the gene banks that have been produced by combinatorial mutagenesis of homologs according to the invention. The most frequently used techniques for the screening of large gene banks, that are subject to an analysis with high throughput, comprise the cloning of the gene bank in replicable expression vectors, transforming of the suitable cells using the resulting vector bank and expressing the combinatorial genes under conditions under which the detection of the desired activity facilitates the isolation of the vector that encodes the gene, the product of which was detected. Recursive ensemble mutagenesis (REM), a technique that increases the frequency of functional mutants in the banks, can be used in combination with the screening tests to identify homologs (Arkin and Yourvan (1992) PNAS 89:7811-7815; Delgrave et al. (1993) Protein Engineering 6(3):327-331).

3. Nucleic Acids and Constructs 3.1 Nucleic Acids

The invention also relates to nucleic acid sequences that code for an enzyme with HSDH activity, such as, for example, 3α-, 3β-, 7β-, 11α-, 11β-, 12α-, 12β-, 17α-, 17β-, 20α-, or 20β-HSDH activity, in particular 3α-, 7β- or 12α-HSDH activity, or constructs that are used for the production of knockout mutants according to the invention.

The present invention also relates to nucleic acids with a certain degree of identity to the sequences actually described herein.

"Identity" between two nucleic acids is understood as meaning the identity of the nucleotides over the total nucleic acid length in each case, in particular the identity that is calculated by comparison with the aid of the Vector NTI Suite 7.1 software of Informax (USA) using the Clustal method (Higgins D G, Sharp P M. Fast and sensitive multiple sequence alignments on a microcomputer. Comput Appl. Biosci. 1989 April; 5(2):151-1) with the setting of the following parameters:

| Multiple alignment parameters: | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

Alternatively to this, the identity can also be determined according to Chenna, Ramu, Sugawara, Hideaki, Kolke, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, that can be found on the worldwide web and using the following parameters:

| DNA Gap Open Penalty | 15.0 |
| --- | --- |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All nucleic acid sequences mentioned herein (single- and double-stranded DNA and RNA sequences, such as, for example, cDNA and mRNA) can be prepared in a manner known per se by chemical synthesis from the nucleotide building blocks, such as for example by fragment condensation of individual overlapping, complementary nucleic acid building blocks of the double helix. The chemical synthesis of oligonucleotides can be carried out, for example, in a known manner, according to the phosphoamidite method (Voet, Voet, 2nd edition, Wiley Press New York, pages 896-897). The addition of synthetic oligonucleotides and filling of gaps with the aid of the Klenow fragment of the DNA polymerase and ligation reactions and general cloning methods are described in Sambrook et al. (1989), Molecular Cloning: A laboratory manual, Cold Spring Harbor Laboratory Press.

The invention also relates to nucleic acid sequences (single- and double-stranded DNA and RNA sequences, such as, for example, cDNA and mRNA), coding for one of the above polypeptides and functional equivalents thereof, which, for example, are accessible using synthetic nucleotide analogs.

The invention relates to both isolated nucleic acid molecules, which code for polypeptides or proteins or biologically active sections thereof according to the invention, as well as nucleic acid fragments that, for example, can be used for use as hybridization probes or primers for identification or amplification of nucleic acids encoding according to the invention.

The nucleic acid molecules according to the invention can moreover contain untranslated sequences of the 3'- and/or 5'-end of the encoding gene region.

The invention furthermore comprises the nucleic acid molecules complementary to the nucleotide sequences actually described or a section thereof.

The nucleotide sequences according to the invention make possible the production of probes and primers that can be used for the identification and/or cloning of homologous sequences in other cell types and organisms. Such probes or primers usually comprise a nucleotide sequence region, that under "stringent" conditions (see below) hybridizes to at least approximately 12, preferably at least approximately 25, such as, for example, approximately 40, 50 or 75 successive nucleotides of a sense strand of a nucleic acid sequence according to the invention or of a corresponding antisense strand.

An "isolated" nucleic acid molecule is separated off from other nucleic acid molecules that are present in the natural source of the nucleic acid and can moreover be essentially free of other cellular material or culture medium, if it is produced by recombinant techniques, or free of chemical precursors or other chemicals, if it is synthesized chemically.

A nucleic acid molecule according to the invention can be isolated by means of molecular biological standard techniques and the sequence information provided according to the invention. For example, cDNA can be isolated from a suitable cDNA bank by using one of the actually disclosed complete sequences or a section thereof as a hybridization probe and standard hybridization techniques (as, for example, described in Sambrook. J., Fritsch, E. F. and Maniatis, T. Molecular Cloning: A Laboratory Manual. 2. ed., Cold Spring Harbor Laboratory, Cold Spring Harbor Laboratory Press, Cold Spring Harbor, N.Y., 1989). Moreover, a nucleic acid molecule, comprising one of the disclosed sequences or a section thereof, can be isolated by polymerase chain reaction, wherein the oligonucleotide primers, that were prepared on the basis of this sequence, are used. The nucleic acid thus amplified can be cloned into a suitable vector and characterized by DNA sequence analysis. The oligonucleotides according to the invention can furthermore be prepared by standard synthesis methods, for example, using an automatic DNA synthesis apparatus.

Nucleic acid sequences according to the invention or derivatives thereof, homologs or sections of these sequences can be isolated from other bacteria, for example, using customary hybridization methods or the PCR prior art, for example, by means of genomic or cDNA banks. These DNA sequences hybridize under standard conditions with the sequences according to the invention.

"Hybridize" is understood as meaning the ability of a poly- or oligonucleotide to bind to an almost complementary sequence unter standard conditions, while under these conditions non-specific bindings between non-complementary partners do not occur. For this, the sequences can be complementary to 90-100%. The characteristic of complementary sequences, of being able to bind specifically to one another, is taken advantage of, for example in the Northern or Southern blot technique or in the primer binding in PCR or RT-PCR.

Short oligonucleotides of the conserved regions are advantageously used for hybridization. It is also possible, however, to use longer fragments of the nucleic acids according to the invention or the complete sequences for the hybridization. Depending on the nucleic acid used (oligonucleotide, relatively long fragment or complete sequence) or depending on which type of nucleic acid DNA or RNA are used for the hybridization, these standard conditions vary. Thus the melt temperatures, for example, for DNA:DNA hybrids are about 10° C. lower than those of DNA:RNA hybrids of equal length.

Standard conditions are to be understood, for example, depending on nucleic acid, as meaning temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide such as, for example, 42° C. in 5×SSC, 50% formamide. Advantageously, the hybridization conditions for DNA:DNA hybrids are 0.1×SSC and temperatures between approximately 20° C. to 45° C., preferably between approximately 30° C. to 45° C. For DNA:RNA hybrids, the hybridization conditions are advantageously 0.1×SSC and temperatures between approximately 30° C. to 55° C., preferably between approximately 45° C. to 55° C. These temperatures indicated for the hybridization are melt temperature values calculated by way of example for a nucleic acid with a length of about 100 nucleotides and a G+C content of 50% in the absence of formamide. The experimental conditions for the DNA hybridization are described in relevant textbooks of genetics, such as, for example, Sambrook et al., "Molecular Cloning", Cold Spring Harbor Laboratory, 1989, and can be calculated according to formulae known to the person skilled in the art, for example, dependent on the length of the nucleic acids, the type of hybrids or the G+C content. The person skilled in the art can gather further information for hybridization from the following textbooks: Ausubel et al. (eds), 1985, Current Protocols in Molecular Biology, John Wiley & Sons, New York; Flames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The "hybridization" can in particular take place under stringent conditions. Such hybridization conditions are described, for example, in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are in particular understood as meaning: Incubation at 42° C. overnight in a solution consisting of 50% formamide, 5×SSC (750 mM NaCl, 75 mM trisodium citrate), 50 mM sodium phosphate (pH7.6), 5×Denhardt solution, 10% dextran sulfate and 20 g/ml of denatured, sheared salmon sperm DNA, followed by a washing step of the filter with 0.1×SSC at 65° C.

The invention also relates to derivatives of the actually disclosed or derivable nucleic acid sequences.

Thus further nucleic acid sequences according to the invention can be derived, for example, from SEQ ID NO:1 to 9, 11, 13, 15, 17 to 22, 24, 26, 27, 28, 30, and 33 to 37 and be distinguished therefrom by addition, substitution, insertion or deletion of single or multiple nucleotides, but furthermore code for polypeptides with the desired property profile.

According to the invention, also comprised are those nucleic acid sequences that comprise "silent" mutations or are modified corresponding to the codon use of a special origin or host organism, in comparison to an actually mentioned sequence, as well as naturally occurring variants, such as, for example, splice variants or allele variants thereof.

The invention likewise relates to sequences obtainable by conservative nucleotide substitutions (i.e. the amino acid concerned is replaced by an amino acid of identical charge, size, polarity and/or solubility).

The invention also relates to the molecules derived by sequence polymorphisms of the nucleic acids actually disclosed. These genetic polymorphisms can exist between individuals within a population on account of the natural variation. These natural variations customarily produce a variance of 1 to 5% in the nucleotide sequence of a gene.

Derivatives of the abovementioned nucleic acid sequence according to the invention are understood as meaning, for example, allele variants that have at least 60% homology at the derived amino acid level, preferably at least 80° A) homology, very particularly preferably at least 90% homology over the entire sequence range (with respect to homology at amino acid level reference may be made to the above embodiments for the polypeptides). The homologies can advantageously be higher over subareas of the sequences.

Moreover, derivatives are to be understood as meaning, for example, fusions with promoters. The promoters that are located upstream of the nucleotide sequences indicated can be modified by at least one nucleotide replacement, at least one insertion, inversion and/or deletion without, however, the functionality or efficacy of the promoters being impaired. In addition, the promoters can be increased in their activity by modification of their sequence or foreign organisms can also be completely replaced by more active promoters.

Moreover, methods for the production of functional mutants are known to the person skilled in the art.

Depending on the technique used, the person skilled in the art can completely introduce random or alternatively more targeted mutations into genes or alternatively non-coding nucleic acid regions (that are important, for example, for the regulation of the expression) and subsequently creates gene banks. The molecular biology methods necessary for this are known to the person skilled in the art and described, for example, in Sambrook and Russell, Molecular Cloning. 3rd Edition, Cold Spring Harbor Laboratory Press 2001.

Methods for modification of genes and thus for modification of the protein encoded by these have been familiar to the person skilled in the art for a long time, such as, for example, site-specific mutagenesis, in which single or multiple nucleotides of a gene are replaced in a targeted manner (Trower M K (Ed.) 1996; In vitro mutagenesis protocols. Humana Press, New Jersey), saturation mutagenesis, in which a codon for any desired amino acid can be replaced or added at any desired site of a gene (Kegler-Ebo D M, Docktor C M, DiMaio D (1994) Nucleic Acids Res 22:1593; Barettino D. Feigenbutz M, Valcárel R. Stunnenberg H G (1994) Nucleic Acids Res 22:541; Batik S (1995) Mol Biotechnol 3:1), error-prone polymerase chain reaction (error-prone PCR), in which nucleotide sequences are mutated by error-prone DNA polymerases (Eckert K A, Kunkel T A (1990) Nucleic Acids Res 18:3739);

passaging of genes in mutator strains, in which, for example, an increased mutation rate of nucleotide sequences occurs on account of defective DNA repair mechanisms (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction, in which through mosaic genes of full length are produced by repeated strand separation and re-approach (Stemmer W P C (1994) Nature 370:389; Stemmer W P C (1994) Proc Natl Acad Sci USA 91:10747).

Using "directed evolution" (described, inter alia, in Reetz M T and Jaeger K-E (1999), Topics Curr Chem 200:31; Zhao H. Moore J C, Volkov A A, Arnold F H (1999), Methods for optimizing industrial enzymes by directed evolution, in: Demain A L, Davies J E (Ed.) Manual of industrial microbiology and biotechnology. American Society for Microbiology) the person skilled in the art can also produce functional mutants in a selective manner and also on a large scale. Here, in a first step gene banks of the respective proteins are firstly produced, wherein, for example, the methods indicated above can be used. The gene banks are expressed in a suitable manner, for example by bacteria or by phage display systems.

The genes concerned of host organisms that express functional mutants with properties which largely correspond to the desired properties, can be subjected to a further round of mutation. The steps of the mutation and of the selection or of the screening can be repeated iteratively until the present functional mutants have the desired properties to an adequate extent. By means of this iterative procedure, a limited number of mutations, such as, for example, 1 to 5 mutations, can be performed stepwise and assessed and selected for their influence on the enzyme property concerned. The selected mutant can then be subjected in the same manner to a further mutation step. The number of the individual mutants to be investigated can be significantly reduced thereby.

The results according to the invention yield important information with respect to structure and sequence of the enzymes concerned, that is necessary to selectively generate further enzymes with desired modified properties. In particular, "hot spots" can be defined, i.e. sequence sections, that are potentially suitable for modifying an enzyme property by means of the introduction of select mutations.

Non-limiting examples of such hot spot regions of the HSDH according to the invention are summarized below:

35-40, in particular 37-38, (in each case based on the amino acid sequence of HSDH_short (SEQ ID NO: 14).

90-105, 93-100 or 96-100, in particular 97 and/or 98, (in each case based on the amino acid sequence of HSDH_short (SEQ ID NO: 14).

3.2 Constructs

The invention moreover relates to expression constructs containing a nucleic acid sequence coding for a polypeptide according to the invention under the genetic control of regulatory nucleic acid sequences; and vectors comprising at least one of these expression constructs.

An "expression unit" is understood according to the invention as meaning a nucleic acid with expression activity, which comprises a promoter, such as defined herein, and after functional linkage with a nucleic acid or a gene to be expressed, regulates the expression, that is the transcription and the translation of this nucleic acid or this gene. It is therefore also spoken in this connection of a "regulatory nucleic acid sequence". Additionally to the promoter, further, regulatory elements, such as, for example, enhancers, can be contained.

An "expression cassette" or "expression construct" is understood according to the invention as meaning an expression unit that is functionally linked with the nucleic acid to be expressed or is functionally linked to the gene to be expressed. In contrast to an expression unit, an expression cassette thus comprises not only nucleic acid sequences, which regulate transcription and translation, but also the nucleic acid sequences, which as a result of the transcription and translation should be expressed as a protein.

The terms "expression" or "overexpression" describe in the context of the invention the production or increase in the intracellular activity of one or more enzymes in a microorganism, that are encoded by the corresponding DNA. To this end, for example, a gene can be introduced into an organism, a gene present can be replaced by another gene, the copy number of the gene or of the genes can be increased, a strong promoter can be used or a gene can be used that codes for a corresponding enzyme with a high activity and these measures can optionally be combined.

Preferably, such constructs according to the invention comprise 5'-upstream of the respective encoding sequence a promoter and 3'-downstream a terminator sequence and optionally other customary regulatory elements, namely in each case operatively linked with the encoding sequence.

A "promoter", a "nucleic acid with promoter activity" or a "promoter sequence" is understood according to the invention as meaning a nucleic acid that, in functional linkage with a nucleic acid to be transcribed, regulates the transcription of this nucleic acid.

A "functional" or "operative" linkage is understood in this connection as meaning, for example, the sequential arrangement of one of the nucleic acids with promoter activity and a nucleic acid sequence to be transcribed and optionally further regulatory elements, such as, for example, nucleic acid sequences that guarantee the transcription of nucleic acids, and, for example, a terminator, such that each of the regulatory elements can fulfill its function in the transcription of the nucleic acid sequence. To this end, a direct linkage in the chemical sense is not absolutely necessary. Genetic control sequences, such as, for example, enhancer sequences, can exert their function also from further removed positions or even from other DNA molecules on the target sequence. Arrangements are preferred in which the nucleic acid sequence to be transcribed is positioned downstream (i.e. at the 3'-end) of the promoter sequence, such that both sequences are covalently bonded to one another. Here, the distance between the promoter sequence and the nucleic acid sequence to be expressed transgenically can be less than 200 base pairs, or smaller than 100 base pairs or smaller than 50 base pairs.

In addition to promoters and terminator, targeting sequences, enhancers, polyadenylation signals, selectable markers, amplification signals, replication origins and the like may be mentioned as examples of further regulatory elements. Suitable regulatory sequences are described, for example, in Goeddel, Gene Expression Technology: Methods in Enzymology 185, Academic Press, San Diego, Calif. (1990).

Nucleic acid constructs according to the invention in particular comprise sequence SEQ ID NO: 11, 13 or 15 or derivatives and homologs of this, and the nucleic acid sequences derivable therefrom, which for control, for example, increase, of the gene expression were advantageously operatively or functionally linked with one or more regulation signals.

Additionally to these regulation sequences, the natural regulation of these sequences ahead of the actual structural genes can still have been present and optionally genetically modified such that the natural regulation was switched off and the expression of the genes increased. The nucleic acid construct can, however, also be constructed more simply, that is there were no additional regulation signals inserted before the encoding sequence and the natural promoter with its regulation was not removed. Instead of this, the natural regulation sequence is mutated such that regulation no longer takes place and the gene expression is increased.

A preferred nucleic acid construct advantageously also contains one or more of the already mentioned "enhancer" sequences, functionally linked to the promoter, which make possible an increased expression of the nucleic acid sequence. Additional advantageous sequences can also be inserted at the 3'-end of the DNA sequences, such as further regulatory elements or terminators. The nucleic acids according to the invention can be contained in one or more copies in the construct. In the construct, still further markers, such as antibiotic resistances or auxotrophy-complementing genes, can optionally be contained for selection on the construct.

Examples of suitable regulation sequences are contained in promoters such as cos, tac, trp, tet, trp-tet, Ipp, lac, Ipp-lac, lacI$^q$, T7, T5, T3, gal, trc, ara, rhaP (rhaP$_{BAD}$)SP6, lambda-P$_R$ or in the lambda-P$_L$ promoter, which are advantageously used in gram-negative bacteria. Further advantageous regulation sequences are contained, for example, in the gram-positive promoters amy and SPO2, and in the yeast or fungal promoters ADC1, MFalpha, A C, P-60, CYC1, GAPDH, TEF, rp28, ADH. Artificial promoters can also be used for regulation.

For expression in a host organism, the nucleic acid construct is advantageously inserted in a vector, such as, for example, a plasmid or a phage, which makes possible optimal expression of the genes in the host. Vectors are to be understood as meaning, apart from plasmids and phages, also all other vectors known to the person skilled in the art, that is, for example, viruses, such as SV40. CMV, baculovirus and adenovirus, transposons, IS elements, phasmids, cosmids, and linear or circular DNA. These vectors can be autonomously replicated in the host organism or chromosomally replicated. These vectors are a further embodiment of the invention.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The plasmids mentioned represent a small selection of the possible plasmids. Further plasmids are well known to the person skilled in the art and can be taken, for example, from the book Cloning Vectors (Eds. Pouwels P. H. et al. Elsevier, Amsterdam-New York-Oxford, 1985, ISBN 0 444 904018).

In a further embodiment of the vector, the vector containing the nucleic acid construct according to the invention or the nucleic acid according to the invention can also advantageously be introduced in the form of a linear DNA into the microorganisms and integrated into the genome of the host organism by means of heterologous or homologous recombination. This linear DNA can consist of a linearized vector such as a plasmid or only of the nucleic acid construct or of the nucleic acid according to the invention.

For an optimal expression of heterologous genes in organisms it is advantageous to change the nucleic acid sequences corresponding to the specific "codon usage" used in the organism. The "codon usage" can easily be determined by means of computer evaluations of other, known genes of the organism concerned.

The production of an expression cassette according to the invention takes place by fusion of a suitable promoter with a suitable encoding nucleotide sequence and a terminator or polyadenylation signal. To this end, common recombination and cloning techniques are used, such as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted for expression into a suitable host organism, advantageously into a host-specific vector, which makes possible an optimal expression of the genes in the host. Vectors are well-known to the person skilled in the art and can be taken, for example, from "Cloning Vectors" (Pouwels P. H. et al., ed, Elsevier, Amsterdam-New York-Oxford, 1985).

4. Microorganisms

Depending on composition, the term "microorganism" can be understood as meaning the starting microorganism (wildtype) or a genetically modified, recombinant microorganism or both.

With the aid of the vectors according to the invention, recombinant knockout microorganisms can be produced, which are transformed, for example, with at least one vector according to the invention and can be employed for production of the polypeptides according to the invention. Advantageously, the recombinant constructs according to the invention described above are introduced into a suitable host system and expressed. Here, common cloning and transfection methods, such as for example co-precipitation, protoplast fusion, electroporation, retroviral transfection and the like, known to the person skilled in the art are preferably used to bring the nucleic acids mentioned to expression in the respective expression system. Suitable systems are described, for example in Current Protocols in Molecular Biology, F. Ausubel et al., ed., Wiley Interscience, New York 1997, or Sambrook et al. Molecular Cloning: A Laboratory Manual. 2nd ed., Cold Spring Harbor Laboratory, Cold Spring Harbor Laboratory Press, Cold Spring Harbor, N.Y., 1989.

Suitable recombinant host organisms for the nucleic acid or the nucleic acid construct according to the invention are in principle all prokaryotic or eukaryotic organisms. Advantageously, microorganisms such as bacteria, fungi or yeasts are used as host organisms. Advantageously, gram-positive or gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium, Clostridium* or *Rhodococcus* are used. Very particularly preferred is the genus and species *Escherichia coli*. Further advantageous bacteria can moreover be found in the group of the alpha-proteobacteria, beta-proteobacteria or gamma-proteobacteria.

The host organism or the host organisms according to the invention here preferably contain at least one of the nucleic acid sequences described in this invention, nucleic acid constructs or vectors that code for an enzyme with HSDH activity, such as, for example, 3α-, 3β-, 7β-, 11α-, 11β-, 12α-, 12β-, 17α-, 17β-, 20α-, or 20β-HSDH activity, in particular 3α-, 7β- or 12α-HSDH activity, according to the above definition.

The organisms used in the method according to the invention are each cultured or grown according to host organism in a manner known to the person skilled in the art. Microorganisms are generally cultured in a liquid medium that contains a carbon source usually in the form of sugars, a nitrogen source usually in the form of organic nitrogen sources such as yeast extract or salts such as ammonium sulfate, trace elements such as iron, manganese or magnesium salts and optionally vitamins, at temperatures between 0° C. and 100° C., preferably between 10° C. to 60° C. with oxygen aeration. Here, the pH of the nutrient liquid can be kept at a fixed value, that is can be regulated or not during culturing. The culturing can take place "batch"-wise, "semi batch"-wise or continuously. Nutrients can be provided at the start of the fermentation or subsequently fed semi-continuously or continuously.

5. Enzymatic/Chemical Production of UDCA 5.1 Oxidative Method

This is described, for example, in WO 2009/118176 of the Applicant.

For the medicinal treatment of cholelithiasis, for many years, inter alia, the active substances ursodeoxycholic acid (UDCA) and the associated diastereomer chenodeoxycholic acid (CDCA) have been employed. Both compounds differ only by the configuration of the hydroxyl group on the 7 C atom (UDCA: β-configuration, CDCA: α-configuration). For the production of commercial amounts of UDCA, previously a method has preferably been used, in which CDCA is employed as a raw material. CDCA is in turn preferably prepared from cholic acid (CA).

5.1.1 CDCA Production

As an alternative to the exclusively chemical method, according to the invention an enzyme-catalyzed oxidation of CA to 12-ketochenodeoxycholic acid (12-keto-CDCA, CAS 2458-08-4), which is then converted further to CDCA, is provided. This synthesis route comprises only two steps and is thus clearly simpler to carry out in comparison to the purely chemical route.

1st Step: Enzymatic Oxidation

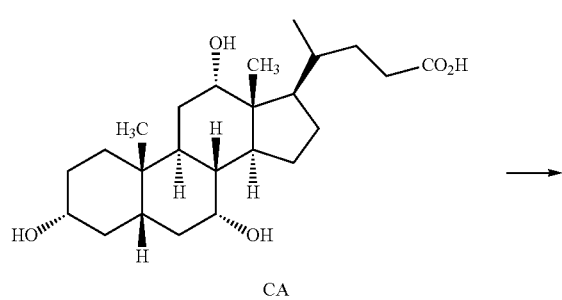

CA

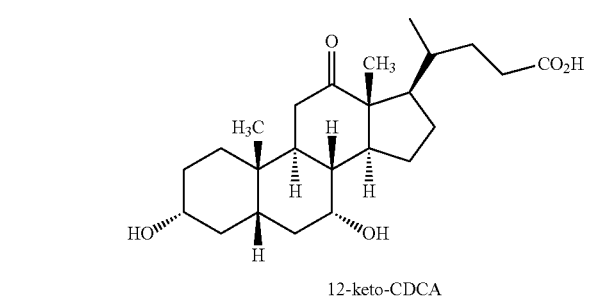

12-keto-CDCA

2nd Step: Deoxygenation

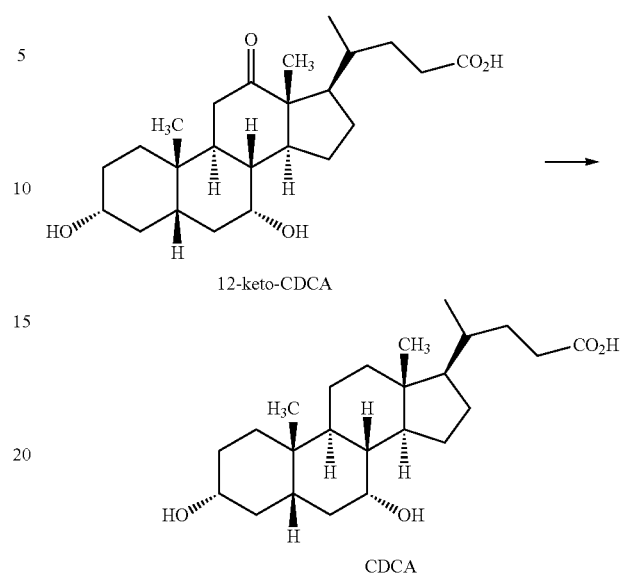

12-keto-CDCA

CDCA

According to step 1, cholic acid is oxidized $NADP^+$-dependently to 12-ketochenodeoxycholic acid (12-keto-CDCA) by means of 12α-HSDH. This reaction is reversible. 12α-HSDHs belong to the enzyme class 1.1.1.176 and are mainly found in bacteria of the genus *Clostridium*.

The enzymatic oxidation takes place according to the invention preferably by means of a 12α-HSDH according to the invention (long or short version) and cofactor regeneration by means of an ADH, such as, for example, ADH ms or ADH t.

The deoxygenation according to step 2 is a classical chemical Wolff-Kishner reduction and is carried out analogously to the deoxygenation of the CDCA III described above. A significant advantage of this route is that owing to the selectivity of the enzyme the impurity lithocholic acid is not formed.

5.1.2 Reaction of CDCA to UDCA

The above CDCA is used as a raw material for UDCA (CAS 128-13-2). In the first synthesis step, the hydroxyl group in position 7 of the COCA is oxidized to the corresponding ketone. 7-ketolithocholic acid (3α-hydroxy-7-ketocholanic acid, in brief: KLCA, CAS 4.651-67-6) results. In the second step, the stereoselective reduction of the keto group in position 7 follows. The aim is to obtain UDCA with as high diastereoselectivity as possible. Generally, the UDCA directly after the reduction still contains a few percent of the diastereomer CDCA. To arrive at the active substance UDCA, crude UDCA must be purified in a third step.

1st Step: Oxidation

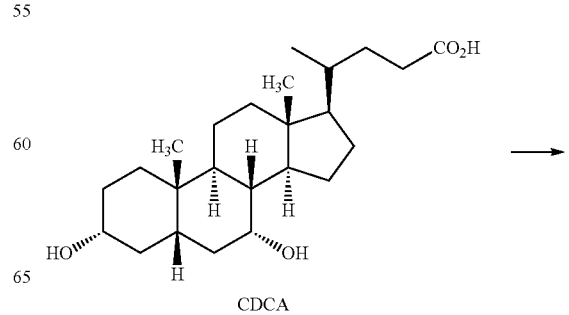

CDCA

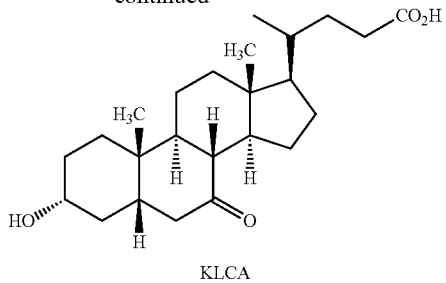

KLCA

2nd Step: Reduction

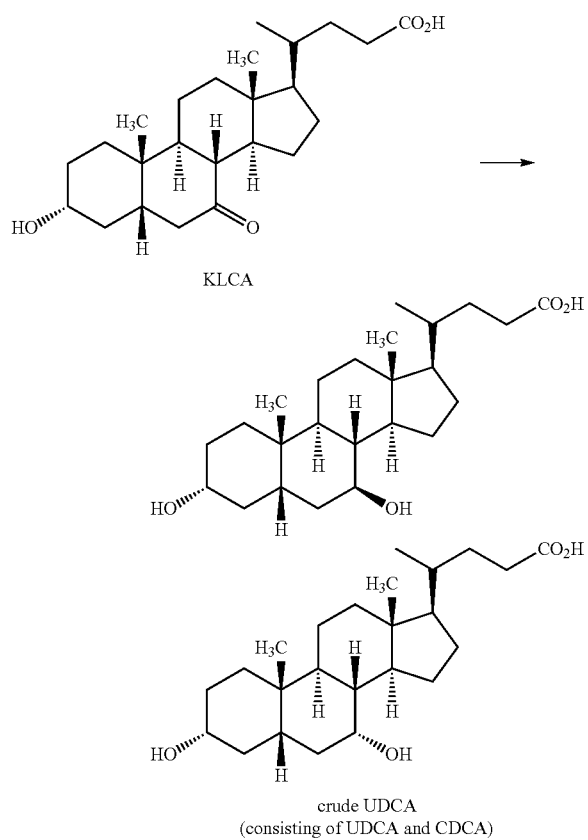

KLCA crude UDCA
(consisting of UDCA and CDCA)

3rd Step: Purification
Crude UDCA→pure UDCA

The oxidation of the CDCA customarily takes place with aqueous sodium hypochlorite solution. In the literature, chromic acid oxidation is still found as an alternative. KLCA is obtained as a solid, which is then further processed in the second step. The reduction can be carried out with sodium metal in alcohols. A crude product with a composition of UDCA: CDCA of about 85:15 results. In alternative methods. KLCA is reduced using hydrogen on a nickel catalyst (Raney nickel) in alcohols (such as, for example, aliphatic alcohols) as a solvent together with a base, such as potassium t-butylate or potassium hydroxide (EP-A-0 230 085). In addition, reduction with potassium and lithium (higher selectivity than sodium, C. Giordano et al. Angew. Chem. 1985, 97, 510) and zinc (ES 489661) and electrochemically (U.S. Pat. No. 4,547, 271) is additionally possible.

The purification of crude UDCA to pure UDCA is a separation of diastereomeric salts. It is carried out by preparation, isolation and subsequent cleavage of a suitable salt of UDCA. The following alternative purification methods are mentioned in the literature: preparation, recrystallization and cleavage of a corresponding UDCA ester (EP-A-0386 538), extractions (JP 60006699) and chromatographic methods. (IT 2000MI1177).

5.2 Reductive Method

Such a method is described, for example, in the PCT/EP2010/068576 of the Applicant.

5.2.1 Chemical Reaction of CA to DHCA

The hydroxyl groups of CA are oxidized with chromic acid or chromates in acidic solution (for example $H_2SO_4$) to carbonyl group in a manner known per se in the classic chemical pathway. DHCA results thereby.

5.2.2 Enzymatic or Microbial Reaction of DHCA to 12-Keto-UDCA

In aqueous solution, DHCA is reduced specifically to 12-keto-UDCA by 3α-HSDH and 7β-HSDH or mutants thereof in the presence of NADPH or NADH. The cofactor NADPH or NADH can be regenerated by an alcohol dehydrogenase (ADH) or formate dehydrogenase (FDH) or glucose dehydrogenase (GDH) or mutants thereof and in the presence of isopropanol or sodium formate or glucose. The reaction proceeds under mild condition. For example, the reaction can be carried out at pH=6 to 9, in particular approximately pH=8 and at approximately 10 to 30, 15 to 25 or approximately 23° C. 3α-HSDH and 7β-HSDH can here be employed stepwise, i.e. in any desired sequence successively, or else simultaneously, i.e. in combination.

In the case of a microbial reaction step, recombinant microorganisms, which express the necessary enzyme activity(ies), can be cultured anaerobically or aerobically in the presence of the substrate to be reacted (DHCA) in suitable liquid media. Suitable culturing conditions are known per se to the person skilled in the art. They comprise reactions in the pH range from, for example, 5 to 10 or 6 to 9, at temperatures in the range from 10 to 60 or 15 to 45 or 25 to 40 or 37° C. Suitable media comprise, for example, LB and TB media. The reaction time here can take place, for example, batchwise or continuously or in other customary process variants (such as described above). The reaction time here can be, for example, in the range from minutes to a number of hours or days, and can be, for example, 1 h to 48 h. Optionally, if enzyme activity is not expressed continuously, this can be introduced by addition of a suitable inducer, after reaching a target cell density, e.g. of approximately $OD_{600}$=0.5 to 1.0.

5.2.3: Chemical Reaction of 12-Keto-UDCA to UDCA

The 12-carbonyl group of 12-keto-UDCA is removed by means of Wolff-Kishner reduction in a manner known per se, UDCA thereby results from 12-keto-UDCA. In the reaction, the carbonyl group is first converted with hydrazine to the hydrazone. Subsequently, the hydrazone is heated in the presence of a base (for example, KOH) to 200° C., here nitrogen is eliminated and UDCA formed.

6. Recombinant Production of HSDHs

The invention also comprises the recombinant production of HSDHs, such as, for example, 3α-, 3β-, 7β-, 11α-, 11β-, 12α-, 12β-, 17α-, 17α-, 20α-, or 20β-HSDH, in particular 3α-, 7β- or 12α-HSDHs or functional, biologically active fragments of these, wherein an HSDH-producing knockout microorganism is cultured, the expression of the polypeptides is optionally induced and these are isolated from the culture. The polypeptides can thus also be produced on a large industrial scale, if this is desired.

The knockout microorganisms produced according to the invention can be cultured continuously or batchwise in the batch method (batch culturing) or in the fed batch (fed batch process) or repeated fed batch method (repetitive fed batch process). A summary concerning known culturing methods can be found in the textbook of Chmiel (Bioprozeβtechnik 1. Einführung in die Bioverfahrenstechnik [Bioprocess technology 1. Introduction to bioprocess technology] (Gustav Fischer Verlag, Stuttgart, 1991)) or in the textbook of Storhas (Bioreaktoren und periphere Einrichtungen [Bioreactors and peripheral devices] (Vieweg Verlag, Brunswick/Wiesbaden, 1994)).

The culture medium to be used suitably has to meet the demands of the respective strains. Descriptions of culture media of various microorganisms are contained in the handbook "Manual of Methods for General Bacteriology" of the American Society for Bacteriology (Washington D. C., USA, 1981).

These media that can be employed according to the invention usually comprise one or more carbon sources, nitrogen sources, inorganic salts, vitamins and/or trace elements.

Preferred carbon sources are sugars, such as mono-, di- or polysaccharides. Very good carbon sources are, for example, glucose, fructose, mannose, galactose, ribose, sorbose, ribulose, lactose, maltose, sucrose, raffinose, starch or cellulose. Sugar can also be added to the media by means of complex compounds, such as molasses, or other by-products of sugar refining. It can also be advantageous to add mixtures of various carbon sources. Other possible carbon sources are oils and fats such as, for example, soybean oil, sunflower oil, groundnut oil and coconut fat, fatty acids such as, for example, palmitic acid, stearic acid or linoleic acid, alcohols such as, for example, glycerol, methanol or ethanol and organic acids such as, for example, acetic acid or lactic acid.

Nitrogen sources are usually organic or inorganic nitrogen compounds or materials that contain these compounds. Exemplary nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn steep water, soy meal, soy protein, yeast extract, meat extract and others. The nitrogen sources can be used individually or as a mixture.

Inorganic salt compounds that can be contained in the media comprise the chloride, phosphorus or sulfate salts of calcium, magnesium, sodium, cobalt, molybdenum, potassium, manganese, zinc, copper and iron.

As a sulfur source, inorganic sulfur-containing compounds such as for example sulfates, sulfites, dithionites, tetrathionates, thiosulfates, sulfides but also organic sulfur compounds, such as mercaptans and thiols, can be used.

As a phosphorus source, phosphoric acid, potassium dihydrogenphosphate or dipotassium hydrogenphosphate or the corresponding sodium-containing salts can be used.

Chelating agents can be added to the medium to keep the metal ions in solution. Particularly suitable chelating agents comprise dihydroxyphenols, such as catechol or protocatechuate, or organic acids, such as citric acid.

The fermentation media employed according to the invention customarily also contain other growth factors, such as vitamins or growth promoters, which include, for example, biotin, riboflavin, thiamine, folic acid, nicotinic acid, panthothenate and pyridoxine. Growth factors and salts often originate from complex media components, such as yeast extract, molasses, corn steep water and the like. Suitable precursors can moreover be added to the culture medium. The exact composition of the media compounds depends strongly on the respective experiment and is decided individually for each specific case. Information on media optimization is obtainable from the textbook "Applied Microbiol. Physiology, A Practical Approach" (ed. P. M. Rhodes, P. F. Stanbury, IRL Press (1997) pp. 53-73, ISBN 0 19 963577 3). Growth media can also be obtained from commercial suppliers, such as Standard 1 (Merck) or BHI (Brain heart infusion, DIFCO) and the like.

All media components are sterilized, either by heat (20 min at 1.5 bar and 121° C.) or by sterile filtration. The components can either be sterilized together or, if necessary, separately. All media components can be present at the start of the culture or can be optionally added continuously or batchwise.

The temperature of the culture is normally between 15° C. and 45° C., preferably at 25° C. to 40° C. and can be kept constant or changed during the experiment. The pH of the medium should be in the range from 5 to 8.5, preferably around 7.0. The pH for the culture can be controlled during the culture by addition of basic compounds such as sodium hydroxide, potassium hydroxide, ammonia or ammonia water or acidic compounds such as phosphoric acid or sulfuric acid. For the control of foam development, antifoams, such as, for example, fatty acid polyglycol esters, can be employed. For the maintenance of the stability of plasmids, suitable selectively acting substances, such as, for example, antibiotics, can be added to the medium. To maintain aerobic conditions, oxygen or oxygen-containing gas mixtures, such as, for example, ambient air, are introduced into the culture. The temperature of the culture is normally 20° C. to 45° C. The culture is continued until a maximum of the desired product has formed. This aim is normally achieved within 10 hours to 160 hours.

The fermentation broth is subsequently further processed. Depending on requirements, the biomass can be completely or partially removed by separation methods, such as, for example, centrifugation, filtration, decanting or a combination of these methods from the fermentation broth or completely left in it.

The cells can also, if the polypeptides are not secreted into the culture medium, disrupted and the product obtained from the lysate according to known protein isolation methods. The cells can optionally be by high-frequency ultrasound, by high pressure, such as, for example, in a French press cell, by osmolysis, by action of detergents, lytic enzymes or organic solvents, by homogenizers or by combination of a number of the methods listed.

A purification of the polypeptides can be achieved using known, chromatographic methods, such as molecular sieve chromatography (gel filtration), such as Q-Sepharose chromatography, ion-exchange chromatography and hydrophobic chromatography, and using other customary methods such as ultrafiltration, crystallization, salting out, dialysis and native gel electrophoresis. Suitable methods are described, for example, in Cooper, F. G., Biochemische Arbeitsmethoden [Biochemical Working Methods], Verlag Walter de Gruyter, Berlin, N.Y. or in Scopes, R., Protein Purification, Springer Verlag, New York, Heidelberg, Berlin.

It can be advantageous for isolation of the recombinant protein to use vector systems or oligonucleotides that lengthen the cDNA by determined nucleotide sequences and thus code for modified polypeptides or fusion proteins, which, for example, serve for simpler purification. Suitable modifications of this type are, for example, "tags" functioning as anchors, such as, for example, the modification or epitope known as a hexa-histidine anchor, which can be recognized as antigens of antibodies (described, for example, in Harlow, E. and Lane, D., 1988, Antibodies: A Laboratory Manual. Cold Spring Harbor (N.Y.) Press). This anchor can be used for attachment of the proteins to a solid carrier, such as, for example, a polymer matrix, which, for example can be filled into a chromatography column, or can be used on a microtiter plate or another carrier.

At the same time, this anchor can also be used for recognition of the proteins. For the recognition of the proteins, customary markers, such as fluorescent dyes, enzyme markers, which after reaction with a substrate form a detectable reaction product, or radioactive markers, can moreover be used alone or in combination with the anchors for derivatization of the proteins.

Enzyme Immobilization

The enzymes according to the invention can be employed in the methods described herein in free or immobilized form. An immobilized enzyme is understood as meaning an enzyme that is fixed to an inert carrier. Suitable carrier materials and the enzymes immobilized thereon are known from EP-A-1149849, EP-A-1 069 183 and from DE-A 100193773 and from the references cited therein. Reference is fully made in this respect to the disclosure of these specifications. The suitable carrier materials include, for example, clays, clay minerals, such as kaolinite, diatomaceous earth, perlite, silicon oxide, aluminum oxide, sodium carbonate, calcium carbonate, cellulose powder, anion exchange materials, synthetic polymers, such as polystyrene, acrylic resins, phenol-formaldehyde resins, polyurethanes and polyolefins, such as polyethylene and polypropylene. The carrier materials are employed for production of the supported enzymes customarily in a finely divided, particulate form, wherein porous forms are preferred. The particle size of the carrier material is customarily not more than 5 mm, in particular not more than 2 mm (sieve line). Analogously, on use of the dehydrogenase as a whole cell catalyst a free or immobilized form can be chosen. Carrier materials are, for example. Ca alginate, and carrageenan. Enzymes such as also cells can also be directly crosslinked with glutaraldehyde (crosslinking to CLEAs). Corresponding and further immobilization methods are described, for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

8. Production of Knockout Mutants

Methods for knocking out, for example methods for deleting or inserting nucleic acids or nucleic acid sequences, are known to the person skilled in the art and comprise, for example, customary methods using oligonucleotide primers and PCR and methods using plasmids and restriction enzymes, with whose aid desired modified nucleic acid sequences can be incorporated into the plasmids. This and other molecular genetic methods are generally known and described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L W. Enquist, Experiments with Gene Fusions, Cold Spring Harbor Laboratory, Cold Spring Harbor, N.Y. (1984), Ausubel, F. M. et al., Current Protocols in Molecular Biology, Greene Publishing Assoc. and Wiley Interscience (1987); "Gene Expression Technology", in: Methods in Enzymology, Vol 185, Elsevier, 1990; "Bacterial Genetic Systems", in: Methods in Enzymology, Vol. 204, Elsevier, 1991; "Recombinant DNA, Part E", in Methods in Enzymology, Vol. 154, Elsevier, 1987; and C. D. Smolke (ed.), The metabolic pathway engineering handbook: tools and applications, CRC Press. Boca Raton, 2010; C. Mühlhardt, "The Experimentator: Molekularbiologie/Genomics", 6th ed., Spektrum Akademischer Verlag, Heidelberg 2010; D. Clark, N. Pazdernik, "Molekulare Biotechnologie", Spektrum Akademischer Verlag, Heidelberg, 2009; M. Jahnson (Ed.), "Gentechnische Methoden", 4th ed., Spektrum Akademischer Verlag, Heidelberg, 2006; J. M. S. Bartlett, D. Stirling (Ed.), "Methods in Molecular Biology", Vol. 226, "PCR Protocols", Springer Verlag GmbH, 2003

A further known method for production of knockout mutants is based on homologous recombination. Here, a marker gene is in particular provided with flanking sequences, which are homologous to sequences of the gene to be knocked out, and by means of suitable vehicles (for example plasmids, insertion sequences, transposons) brought together with the target sequence to be knocked out. This is preferably located in a host organism, for example in the chromosome (depending on host organism bacterial chromosome or eukaryotic chromosome) or on an extrachromosomal nucleic acid construct (for example a plasmid) in the host concerned. Cell-free or in-vitro systems are, however, likewise conceivable. In the presence of suitable recombination systems (for example recombinases) a homologous recombination takes place, wherein the marker gene is integrated into the target sequence on account of the homology of the flanking sequences and is removed in the replacement of the nucleic acid region lying between the flanking sequences of the target sequence. The gene product of the marker gene inserted in this manner can be used for selection of the knockout mutants. The marker gene codes preferably for a protein that mediates an antibiotic resistance, such that a selection by means of antibiotic-containing solid medium plates or liquid media can take place. The marker gene can, however, also code for other proteins, for example fluorescent proteins, for example "Green Fluorescent Protein" (GFP), such that a selection can take place by means of colony observation in the fluorescence microscope or by means of fluorescence-activated cell sorting (FACS). The principle of the homologous recombination is generally known and is described, in addition to further forms of recombination, for example, R. Y. Stanier, J. L. Ingraham, M. L. Wheelis, P. R. Painter (ed.) "General Microbiology", 5th ed., 1986, Macmillan Education Ltd., Houndmills, London, pp. 278-285, furthermore in "DNA Cloning", Volume II, D. M. Glover (ed.), IRL Press, Oxford, Washington D.C., 1986, pp. 57-65; Karl Drlica, "DNA und Genklonierungein Leitfaden", G. Fischer Verlag, Stuttgart, Jena, 1995, "Transposition" chapter. pp. 155-161, and D. H. Jones and S. C. Winistorfer, "Recombination and Site-Directed Mutagenesis using Recombination PCR", in: J. M. S. Bartlett, D. Stirling (eds.), "Methods in Molecular Biology", Vol. 226, "PCR Protocols", Springer Verlag GmbH, 2003, Chapter 70, pp., 517-525; and A. S. Waldman (ed.), "Methods in Molecular Biology", Vol. 262, "Genetic Recombination—Reviews and Protocols", Springer Verlag GmbH, 2004; F. P. Miller, A. F. Vandome, J. McBrewster (Ed.), "Genetic Recombination", Alphascript Publishing, 2009; F. P. Miller, A. F. Vandome, J. McBrewster (Eds.), "Gene Targeting", Alphascript Publishing, 2010 A. Aguilera and R. Rothstein, Molecular Genetics of Recombination, Springer-Verlag GmbH, 2007. Special publications on gene-knockout methods are described, in particular for eukaryotic cells and animals "Gene Knockout Protocols", Ralf Kahn and Wolfgang Wurst (eds.), Humana Press., 2nd edition 2009, and Wolf S. E. and Woodside, K. J, Transgenic and gene knockout techniques and burn research, J. Surg. Res. 123(2):328-339, 2005.

Furthermore, commercial kits for production of gene-knockouts are obtainable, for example the "TargeTron gene knockout system" of Sigma-Aldrich, in particular for *E. coli* and related bacterial species.

Examples of further systems suitable for production of knockout mutants or genetic modifications are the Cre/Lox system, described inter alia in Sauer B and Henderson N, Proc. Natl. Acad. Sci. USA 85(14):5166-5170, 1988, or the "Red/ET Recombination" system (Gene Bridges GmbH, Heidelberg, Germany; described in the user handbook "Red/ET Recombination—Cloning without Restrictions Enzymes", Gene Bridges GmbH, further described, inter alia, in the patents U.S. Pat. No. 6,355,412, U.S. Pat. No. 6,509,156 and EP 4139561).

9. Cofactor Regeneration

The need for cofactor can be reduced by the coupling with a cofactor-regenerating enzyme. To this end, various methods of the prior art can be used.

The prior art teaches, for example, the use of glutamate dehydrogenase (GLDH) (Carrea, G., et al., Biotechnology and Bioengineering, 1984. 26(5): p. 560-563). The GLDH reoxidizes NADPH to $NADP^+$ with simultaneous reductive amination of α-ketoglutarate to glutamate.

Alternatively to this, alcohol dehydrogenases ADH-Tb, ADH-Lb and ADH-ms are also proposed for cofactor regeneration (Fossati, E., et al., Biotechnol Bioeng, 2006. 93(6): p. 1216-20). The ADH converts acetone to 2-propanol with regeneration of $NADP^+$.

Further secondary alcohol dehydrogenases for regeneration of the NADH or NAD, are, for example, those that are isolatable from yeasts of the genera *Candida* and *Pichia*, such as, for example: carbonyl reductase from *Candida parapsilosis* (CPCR) (U.S. Pat. No. 5,523,223 and U.S. Pat. No. 5,763,236; Enzyme Microb. Technol. 1993 November; 15(II):950-8), *Pichia capsulata* (DE 10327454.4), *Pichia farinosa* (A 1261/2005, KI. C12N), *Pichia finlandica* (EP 1179595 A1), *Candida nemodendra* (A 1261/2005, KI. C12N), *Pichia trehalophila* (A 1261/2005, KI. C12N), *Rhodotorula mucilaginosa* (A 1261/2005, KI. C12N), *Lodderomyces elongisporus* (A 1261/2005, KI. C12N) and *Pichia stipidis* (A 1261/2005, KI. C12N). In addition, the regeneration of the NADH can also be carried out with secondary alcohol dehydrogenases such as isolated from bacteria of the class of the Actinobacteria, for example, from *Rhodococcus erythropolis* (U.S. Pat. No. 5,523,223), *Norcardia fusca* (Biosci. Biotechnol. Biochem., 63 (10) (1999), pages 1721-1729; Appl. Microbiol. Biotechnol. 2003 September; 62(4):380-6, Epub 2003 Apr. 26), *Rhodococcus ruber* (J. Org. Chem. 2003 Jan. 24; 8(2):402-6.) or *Microbacterium* spec. (A 1261/2005, KI. C12N).

Suitable secondary alcohol dehydrogenases/oxidoreductases for regeneration of NADPH or NADP, are, for example, those such as isolated from organisms of the order Lactobacillales *Lactobacillus kefir* (U.S. Pat. No. 5,200,335), *Lactobacillus brevis* (DE 19610984 A1; Acta Crystallogr. D. Biol. Crystallogr. 2000 December; 56 Pt 12:1696-8), *Lactobacillus minor* (DE 10119274), *Leuconostoc carnosum* (A 1261/2005, KI. C12N) or those, such as described, from *Thermoanerobium brockii, Thermoanerobium ethanolicus* or *Clostridium beijerinckii*.

A cofactor regeneration by lactate dehydrogenase (LDH; reaction of pyruvate to lactate with regeneration of $NAD^+$) is described in in EP-A-1 731 618.

Further suitable dehydrogenases for cofactor regeneration are glucose dehydrogenases (GDH), formate dehydrogenases (FDH) which in particular catalyzes at least the enzymatic oxidation of formic acid to $CO_2$, glucose-6-phosphate dehydrogenase, or phosphite dehydrogenases.

EXPERIMENTAL SECTION

If no other details are given, the cloning steps carried out in the context of the present invention, such as, for example, PCR (polymerase chain reaction), restriction cleavages, agarose gel electrophoresis, purification of DNA fragments, transfer of nucleic acids to nitrocellulose and nylon membranes, linkage of DNA fragments, transformation of microorganisms, culture of microorganisms, replication of phages and sequence analysis of recombinant DNA can be carried out as described in Sambrook et al. (1989) loc. cit.

Figure 3:
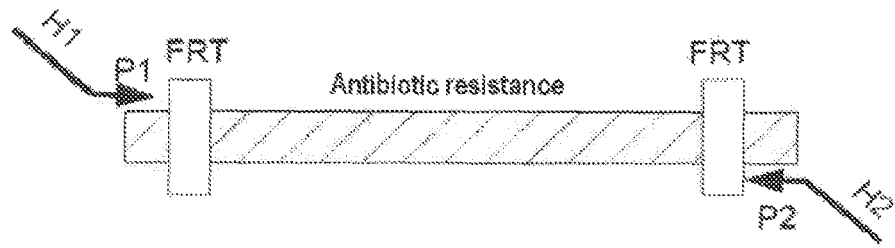
FIG. 3 schematically illustrates the strategy for switching off the 7α-HSDH gene by means of knockout technology. H1 and H2 designate homologous sequences; P1 and P2 designate primer. Gene A and C designate the sequence sections flanking the 7α-HSDH gene. H1 and H2 can both be sequence sections from the flanking regions (such as shown in FIG. 3), or can also represent, for example, 5'- and 3'-terminal sections from the 7α-HSDH gene (source: K. Datsenko and B. Wanner, PNAS Jun. 6, 2000 vol. 97 no. 12 6640-6645.
Figure 3:
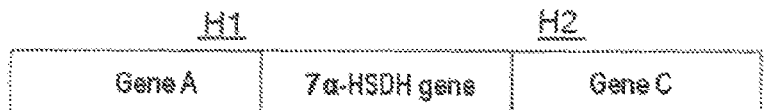
Figure 3:
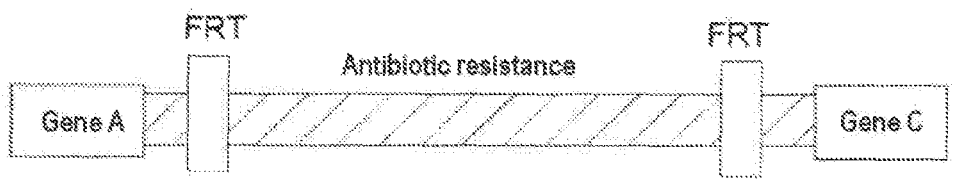
Figure 3:
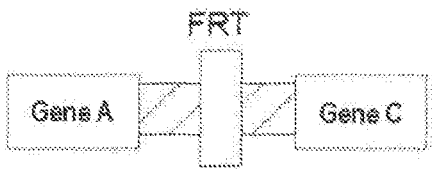

The knockout experiments by homologous recombination take place according to the description of K. Datsenko and B. Wanner, (PNAS Jun. 6, 2000 vol. 97 no. 12 6640-6645), see FIG. 3.

A. General Details

1. Materials:

|  | Tryptone | 10 g/l |
|---|---|---|
|  | Yeast extract | 5 g/l |
|  | NaCl | 5 g/l |
|  | $dH_2O$ | to 1 liter |
| Only for production of solid nutrient media | Agar | 15 g/l |

2. Methods
2.1 Standard Conditions for 12α-HSDH Activity Determination

The activity is defined as follows: 1 U of the enzyme corresponds to the amount of enzyme which the reaction of 1 μmol/min of a 5 mM cholic acid solution in potassium phosphate buffer (50 mM, pH 8.0) at room temperature (i.e. about 20° C.-23° C.) catalyzes.

The reaction mixture contains in a total volume of 1 ml:

| 880 μl | 50 mM potassium phosphate buffer, pH 8.0 |
|---|---|
| 10 μl | 100 mM cholic acid (dissolved in water, pH 8 adjusted with 2 M KOH) |
| 10 μl | enzyme solution (in buffer as above, in the range from 1 to 10 U/ml) |
| 100 μl | 1 mM NADP+ (in buffer as above) (therewith start of the reaction) |

The increase in the absorption at 340 nm is measured and the activity is calculated as an enzyme unit, (U, i.e. μmol/min) using the molar extinction coefficient of $6.22\ mM^{-1} \times cm^{-1}$.

2.2 Standard Conditions for 7β-HSDH Activity Determination

The reaction mixture contains in a total volume of 1 ml:

| 880 μl | 50 mM potassium phosphate buffer, pH 8.0 |
|---|---|
| 10 μl | 10 mM UDCA (dissolved in water, pH 8) |
| 10 μl | enzyme solution (in buffer as above, in the range from 1 to10 U/ml) |
| 100 μl | mM NADP+ (in buffer as above) |

The increase in the absorption at 340 nm is measured and the activity is calculated as an enzyme unit, (U, i.e. μmol/min) using the molar extinction coefficient of $6.22\ mM^{-1} \times cm^{-1}$.

2.3 HPLC Method for Analysis of Reaction Products of the Cholic Acid.

Column: Purospher® STAR RP-18 (Hitbar® RT 125-4 prepacked, pre-column LiChroCART® STAR RP18, Merck)

HPLC System: LC20AD (Shimadzu, Japan)

Flow: 1 ml/min.

Sample: 20 µl in 1 mg/ml

Detection wavelength: 200 nm

Gradient:

| Time (min) | Pump A (%) Acetonitrile | Pump B (%) Water (pH 2.6) |
|---|---|---|
| 0 | 35 | 65 |
| 8 | 35 | 65 |
| 16 | 43 | 57 |
| 18 | 70 | 30 |
| 23 | 70 | 30 |
| 25 | 35 | 65 |
| 30 | 35 | 65 | pH 2.6 adjusted with orthophosphorous acid 85%

Retention Times:

7-keto-3,12-Dehydroxycholanic acid 7.5 min

Cholic acid 13.5 min

3. Expression Vectors and Plasmids and Production Thereof pIJ773 (SEQ ID NO:1)

The plasmid pIJ773 contains the gene that codes for aparamycin resistance (B. Gust et al. PNAS Feb. 18, 2003 vol. 100 no. 4 1541-1546). This resistance is needed for the selection after recombination has taken place.

pJOE6038.1 (Derived from pIJ790) (SEQ ID NO:2)

The plamid pJOE6038.1 (B. Gust et al. PNAS Feb. 18, 2003 vol. 100 no. 4 1541-1546) contains the Lambda Red recombination system, that consists of three genes Gam, Bet and Exo. (K. Murthy, J. Bacteriology, April 1998, p. 2063-2071). Gam inhibits the host exonuclease RecBCD V and makes it possible that Bet and Exo carry out the recombination.

pCP20

For the excision of the selection mark the plasmid pCP20 (K. Datsenko and B. Wanner, PNAS Jun. 6, 2000 vol. 97 no. 12 6640-6645) is employed, that encodes the FLP recombinase necessary for the excision. The FLP recombinase cleaves DNA between the FRT sites.

pET28a(+), pET28a(+), (Novagen, Darmstadt) is a vector, which contains an MCS unter the control of a T7 promoter and transcription start and has a T7 terminator and served for expression of 12α-HSDH. The expression is induced by means of isopropyl-β-D-thiogalactopyranoside (IPTG).

pET28a(+)-7β-HSDH

The plasmid was prepared as follows (cf also PCT/EP20100/068576 of the Applicant):

First, the 7β-HSDH encoding sequence was amplified. The PCR products were obtained with use of the genomic DNA of Collinsella aerofaciens ATCC 25986 (DSM 3979) as a template and the primer 5'-gggaattcCATATGAACCTGAGGGAGAAGTA-3' (SEQ ID NO:26) and 5'-cccAAGCTTCTAGTCGCGGTAGAACGA-3' (SEQ ID NO:27). The NdeI and HindIII cleavage sites in the primer sequences are underlined. The PCR product was purified by means of PCR purification Kit (Qiagen) and then cleaved using the enzymes NdeI and HindIII.

The digested PCR product was purified and cloned in the pET-28a(+) vector using the T4 ligase to produce the expression vector. The resulting expression construct was then transformed in E. coli DH5α cells. The protein to be expected should contain 20 amino acid radicals comprising a signal peptide and an N-terminal 6×His tag and a thrombin cleavage site. The sequence of the inserted DNA was checked by sequencing (cf. SEQ ID NO: 24 and 25).

pET22b(+) 3α-HSDH:

This is a pET22b(+) vector in which the 3α-HSDH sequence from Comamonas testosteroni (cf. SEQ ID NO: 28 and 29) was cloned in via the cleavage sites Nde I and EcoR I in a customary manner (Oppermann et al., J Biochem, 1996, 241(3):744-749).

pET21a(+) FDH D221G

This is a pET21a(+)-vector, in which the formate dehydrogenase from Mycobacterium vaccae N10 (SEQ ID NO:32) was cloned in via the cleavage sites Nde I and EcoR I. By site-directed mutagenesis, the aspartate radical (D) in position 221 (without consideration of methionine in position 1) or position 222 (calculated from methionine in position 1; cf. SEQ ID NO: 38 and 23) of the formate dehydrogenase was replaced by a glycine radical. The FDH mutant thus obtained can regenerate not only NADH, but also NADHP. The formate dehydrogenase carries on the position 1202 (calculated with consideration of the start codon ATG) of the nucleotide sequence a single base deletion, which leads to the exchange of the last amino acid valine for an alanine. At the same time, this base deletion leads to the switching off of the stop codon and to the activation of the His•Tags originally lying outside of the reading frame (cf. SEQ ID NO: 22 and 23). (FDH D221G without His Tag see SEQ ID NO: 37 and 38).

The expression plasmid was prepared as follows (cf. also EP application 10015726 of the Applicant):

a) Cloning pET21a(+) FDH

Genomic DNA of Mycobacterium vaccae N10, which was ordered from the culture collection of the Biology Department of Moscow State University, Russia (deposit number 43292) serves as a template of the amplification. Primers for the amplification were

```
                                              (SEQ ID NO: 33)
fdh_for    (5'-CGATCATATGGCAAAGGTCCTGTGCGTTC-3')
           and (SEQ ID NO: 34)
fdh_rev    (5'-GCTAGAATTCTCAGCCGCCTTCTTGAACT-3'),
``` ordered from Eurofins MWG GmbH, Ebersberg. The recognition sites for the restriction enzymes are underlined. The rev primer contains the EcoRI cleavage site, the for primer contains the NdeI cleavage site.

The PCR batches and PCR programs are indicated in the tables.

TABLE

PCR batch for the amplification of the formate dehydrogenase from Mycobacterium vaccae

| Component | Volume [µl] |
|---|---|
| 10× Taq buffer (with Mg$^{2+}$) | 5 |
| dNTPs (10 mM) | 1 |
| Fdh_for (100 µM) | 0.5 |
| Fdh_rev (100 µM) | 0.5 |

TABLE-continued

PCR batch for the amplification of the formate dehydrogenase from *Mycobacterium vaccae*

| Component | Volume [μl] |
|---|---|
| Template DNA (>=100 ng/μL) | 1 |
| Taq DNA polymerase (5 U/mL) | 0.5 |
| Distilled water | 41.5 |

TABLE

PCR program for the amplification of the formate dehydrogenase from *Mycobacterium vaccae*

| Segment | Cycle number | Denaturation | Annealing | Elongation |
|---|---|---|---|---|
| 1 | 1 | 94° C., 2 min | | |
| 2 | 5 | 94° C., 30 sec | 55.6° C., 30 sec | 72° C., 75 sec |
| 3 | 25 | 94° C., 30 sec | 58.6° C., 30 sec | 72° C., 75 sec |
| 4 | 1 | | | 72° C., 75 sec |

1-5 μg of DNA (pET21a(+) or FDH-PCR product) dissolved in water are treated with 5 μl of 10× NE buffer EcoRI, 2.5 μl of NdeI (20 U/mL) and 2.5 μl of EcoRI (20 U/mL) (in each case New England Biolabs, Frankfurt) and made up with distilled water to 50 μl total volume. The batches were in each case incubated at 37° C. for 1 h. Subsequently, the cleaved DNA fragments are applied to a 1% strength agarose gel (1% (m/v) agarose, 0.05% (v/v) ethidium bromide) and the DNA fragments separated electrophoretically for 55 minutes at 120 V. Subsequently, the bands of the correct size (1.2 kb in the FDH gene, 5.4 kb in the pET21a(+) plasmid) were excised with a scalpel from the agarose gel and isolated with the aid of the QIAQuick Gel Extraction Kit (QIAGEN, Hilden) according to manufacturer's protocol.

100 ng of cleaved vector DNA and 111 ng of cleaved FDH-DNA were treated with 1 μl of T4 ligase (3 U/μL) and 1 μl of 10× ligase buffer (in each case New England Biolabs, Frankfurt) and filled with distilled water to a total volume of 10 μl. The ligation batch was incubated at 4° C. overnight.

After completion of the ligation step, the 10 μL ligation batch are added to 200 μl of chemically competent *E. coli* DH5α produced according to standard protocol. After that, an incubation step on ice takes place for 30 minutes, followed by a heat shock at 42° C. (90 seconds). Subsequently, 600 μl of sterile LB medium are added to the transformation batch and the cells are incubated at 200 rpm and 37° C. in a shaking incubator for 45 minutes. In the next step, the batch is centrifuged at 3000 rpm for 60 seconds in a bench centrifuge, 700 μl of the supernatant are discarded, the cells are resuspended in the remaining supernatant and plated out on an LB agar plate with 100 mg/l of ampicillin. The agar plate is subsequently incubated overnight at 37° C.

b) Production pET21a(+) FDH D221G

The following primers were used:

mt1:
(SEQ ID NO: 35)
5'-C CTG CAC TAC ACC GGC CGT CAC CGC CTG C -3'

Nl_fdh_R:
(SEQ ID NO: 36)
5'-GCTCGAATTCTCAGACCGCCTTC-3'

First, with the aid of the mt primer and of the primer Nl_fdh_R a set of two complementary megaprimers was produced. The template used was plasmid pET21a(+)FDH. The PCR program used can be inferred from the following table:

TABLE

PCR program megaprimer

| Segment | Cycle number | Denaturation | Annealing | Elongation |
|---|---|---|---|---|
| 1 | 1 | 94° C., 2 min | | |
| 2 | 30 | 94° C., 30 sec | 60° C., 30 sec | 72° C., 40 sec |
| 3 | 1 | | | 72° C., 5 min |

By combination of primer mt1 with the primer Nl_fdh_R, the length of the megaprimer turns out to be 650 bp. Using this PCR product of the first PCR, a gel electrophoresis and isolation of the desired band from the gel takes place. A second PCR is carried out as a whole plasmid PCR with the megaprimers as primer and the plasmid DNA (pETfdh) as a template. The following tables show the reaction batch and the temperature scheme for the whole plasmid PCR. The 2× EZClone enzyme mix, the EZClone solution 1, the 1.1 kb marker and the DpnI originated from the GeneMorph II EZClone Domain Mutagenesis Kit (Stratagene).

TABLE

Batch for a MEGA WHOP PCR (total volume 50 μL)

| component | |
|---|---|
| Megaprimer | 250 ng (~2.5 μL from a standard PCR) |
| Template (pETfdh) | 50 ng |
| 2× EZClone enzyme mix | 25 μL |
| EZClone solution 1 | 3 μL |
| Dist. water | to 50 μL |

The first step in the PCR program (68° C., 5 min) serves to remove the bases appended non-specifically by the Taq polymerase by the 3'→5' exonuclease activity of the polymerase employed in the MEGA WHOP PCR.

TABLE

PCR program MEGA WHOP

| Segment | Cycle number | Denaturation | Annealing | Elongation |
|---|---|---|---|---|
| 1 | 1 | | | 68° C., 5 min |
| 2 | 1 | 95° C., 1 min | | |
| 3 | 25 | 95° C., 50 sec | 60° C., 50 sec | 68° C., 13 min |

The PCR product is a double-stranded plasmid with single-strand breaks, which are only closed in *E. coli*. 10 U of DpnI were added to the 50 μL PCR product and the batch was incubated at 37° C. for two hours. DpnI degrades only methylated DNA, i.e. the template DNA employed, but not the megaprimer or the synthesized plasmid. The template plasmid must be produced using a dam+ strain (such as DH10B or JM109) to obtain methylated starting DNA.

In this way, the abovementioned expression plasmid pET21a(+) FDH D221G is obtained

4. Microorganisms

| Strain | Genotype |
|---|---|
| *Escherichia coli* BL21 (DE3) | F⁻ ompT gal dcm lon hsdS$_B$(r$_B$⁻m$_B$⁻) λ(DE3 [lacI lacUV5 T7 gene 1 ind1 sam7 nin5]) |

```
Nucleotide sequence

Length: 768 base pairs

Type: nucleic acids

Source: E. coli BL21(DE3)

Accession: NC_012971 REGION: 1642470...1643237 gtgtttaatt ctgacaacct gagactcgac ggaaaatgcg ccatcatcac aggtgcgggt    60
gcaggtattg gtaaagaaat cgccattaca ttcgcgacag ctggcgcatc tgtggtggtc   120
agtgatatta acgccgacgc agctaaccat gttgtagacg aaattcaaca actgggtggt   180
caggcatttg cctgccgttg tgatattact tccgaacagg aactctctgc actggcagac   240
tttgctatca gtaagctggg taaagttgat attctggtta acaacgccgg tggcggtgga   300
cctaaaccgt ttgatatgcc aatggcggat tttcgccgtg cttatgaact gaatgtgttt   360 tctttttttcc atctgtcaca acttgttgcg ccagaaatgg aaaaaaatgg cggtggcgtt   420
attctgacca tcacttctat ggcggcagaa aataaaaata taaacatgac ttcctatgca   480
tcatctaaag ctgcggccag tcatctggtc agaaatatgg cgtttgacct aggtgaaaaa   540
aatattcggg taaatggcat tgcgccgggg gcaatattaa ccgatgccct gaaatccgtt   600
attacaccag aaattgaaca aaaaatgtta cagcacacgc cgatcagacg tctgggccaa   660
ccgcaagata ttgctaacgc agcgctgttc ctttgctcgc ctgctgcgag ctgggtaagc   720
ggacaaattc tcaccgtctc cggtggtggg gtacaggagc tcaattaa              768
(coding strand)
```

B. Examples

Example 1

Production of a 7α-HSDH Deletion Mutant of the *E. coli* Strain BL21(DE3) (*E. coli* BL21(DE3) Δ7α-HSDH) (Type 1) (Knockout by Homologous Recombination)

1.1 Sequence Information for 7α-HSDH from *E. Coli* BL21 (DE3)

```
Amino acid sequence: (SEQ ID NO: 10)

Length: 255 amino acids

Type: protein

Source: E. coli BL21(DE3)

VFNSDNLRLDGKCAIITGAGAGIGKEIAITFATAGASVVVSDINADAANH

VVDEIQQLGGQAFACRCDITSEQELSALADFAISKLGKVDILVNNAGGGG

PKPFDMPMADFRRAYELNVFSFFHLSQLVAPEMEKNGGGVILTITSMAAE

NKNINMTSYASSKAAASHLVRNMAFDLGEKNIRVNGIAPGAILTDALKSV

ITPEIEQKMLQHTPIRRLGQPQDIANAALFLCSPAASWVSGQILTVSGGG

VQELN
```

1.2 Production of the Aparamycin Deletion Cassette

The following primers were prepared for the knocking out of the 7α-HSDH from *E. coli* BL21(DE3).

```
Forward:
                                                (SEQ ID NO: 3)
5'-GTGTTTAATTCTGACAACCTGAGACTCGACGGAAAAATGATTCCGGG

GATCCGTCGACC-3'

Backward:
                                                (SEQ ID NO: 4)
5'-TTAATTGAGCTCCTGTACCCCACCACCGGAGACGGTTTATGTAGGCT

GGAGCTGCTTC-3'
```

The homologous sequences for 7α-HSDH-sequence are underlined, wherein the underlined sequence from the forward primer for

"VFNSDENLRLDGK" (N→C)

and the underlined sequence from the backward primer for

"TVSGGGVQELN" (N→C)

are encoded.

The homologous sequences for the aparamycin resistance cassette are in italics. The aparamycin resistance cassette from plasmid pIJ773 is franked by FRT sites (B. Gust et al.

PNAS Feb. 18, 2003 vol. 100 no. 4 1541-1546) and allows the resistance after recombination has taken place to be removed from the genome again.

The PCR with the aparamycin resistance cassette from plasmid pIJ773 as a template was carried out according to standard protocol such as Sambrook (1998). The thus produced PCR product with two homology arms from the gene of the 7α-HSDH was purified.

1.3 Recombination/Deletion of the Target Sequence

The plasmid pJOE6038.1, that is equipped with the inverted NheI cleavage site of pIJ790 (B. Gust et al. PNAS Feb. 18, 2003 vol. 100 no. 4 1541-1546), encodes an exonuclease (Lambda Red recombinase, K. Murthy, J. Bacteriology, April 1998, p. 2063-2071). The plasmid pJOE6038.1 is temperature-sensitive and is lost on culturing at 37° C. The plasmid pJOE6038.1 was transformed by means of electroporation (25 µF, 200 ohms and 2.5 kV) in E. coli BL21 (DE3). A colony was picked in 5 ml of LB and cultured overnight at 30° C. 40 ml of LB medium was inoculated 1:100 and incubated at 30° C. At an $OD_{600}$ of about 0.3 the culture was induced with 0.4% L-arabinose and incubated at 37° C. for 1 h to express the exonuclease (Lambda Red recombinase) that makes the recombination, possible.

The cells were centrifuged off and washed with 30 ml of ice-cold water. The cells were centrifuged off again and resuspended with 700 µl of ice-cold water. 50 µl of this were incubated on ice for 30 min with 5 µl of PCR product (from above step 1). After electroporation (25 µF, 200 ohms and 2.5 kV) 1 ml of pre-cooled LB medium was immediately pipetted thereto. The cells were incubated at 37° C. for 2 hours 45 minutes. The cells were then plated out on an LB aparamycin agar plate. A colony was picked. Colony PCR with 7α-HSDH priaiers showed a 1500 bps band (aparmycin resistance). This shows that the gene of the 7α-HSDH was replaced and the aparamycin resistance here was integrated into the genome (see FIG. 1). The knockout strain thus obtained is designated as E. coli BL21(DE3) Δ7α-HSDH Apar$^R$.

1.4 Excision of the Resistance

The resistance gene used for the knocking out flanked by two FRT sites should again be excised. For the excision, the plasmid pCP20 (K. Datsenko and B. Wanner, PNAS Jun. 6, 2000 vol. 97 no. 12 6640-6645) was employed that encodes the FLP recombinase necessary for the excision. The FLP recombinase cuts DNA between the FRT sites. The plasmid pCP20 is also temperature-sensitive and is lost on culturing at 37° C. The plasmid pCP20 was transformed by means of electroporation (25 µF, 200 ohms and 2.5 kV) in the knockout strain E. coli BL21(DE3) Δ7α-HSDH Apar$^R$. 4 colonies were streaked out on LB-0 and cultured at 42° C. overnight, wherein the FLP recombinase was expressed and this excises the aparamycin resistance gene. The knockout strain E. coli BL21(DE3) Δ7α-HSDH is thus obtained.

Figure 2A:
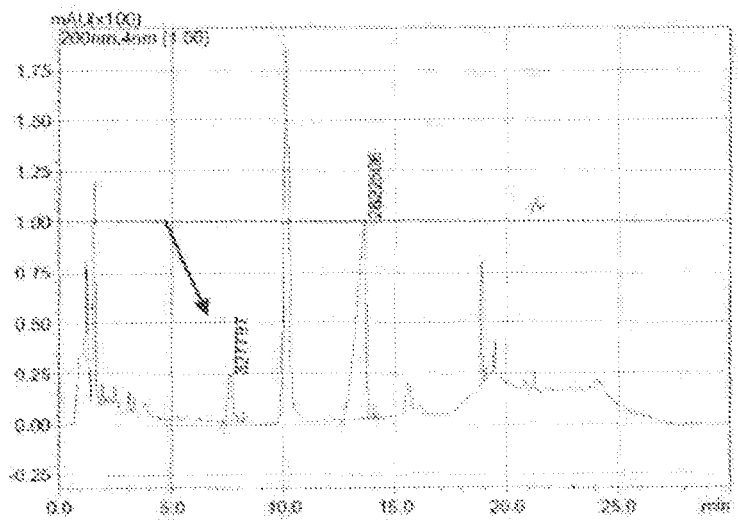
FIGS. 2A-C show the result of the incubation of cholic acid (CA) with various *E. coli* cultures.
Figure 2B:
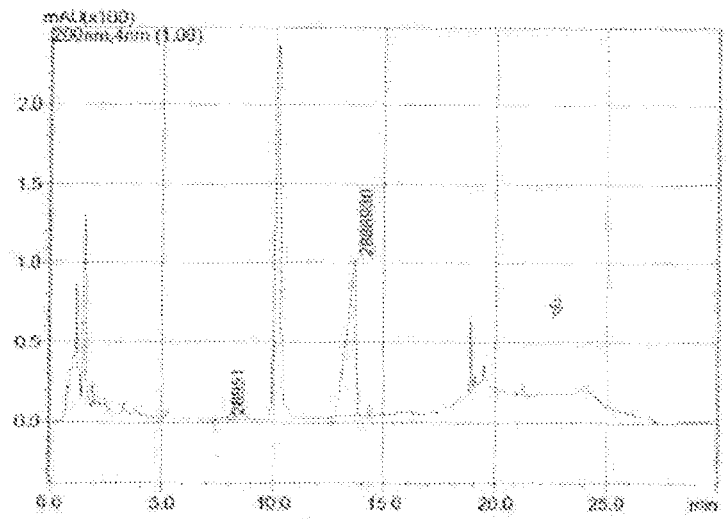
Figure 2C:
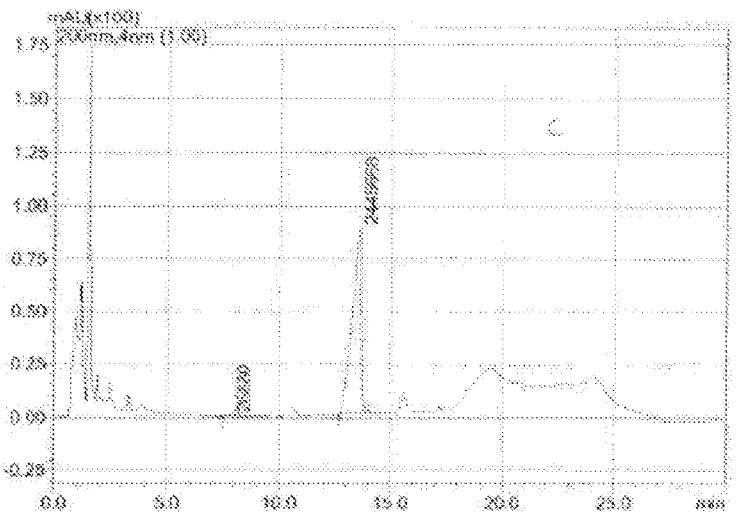

For the test loss of the resistance, 50 colonies was streaked on LB aparamycin medium and LB-0 medium. The colonies that are only grown on LB-0 no longer carry aparmycin resistance. A colony was picked in 5 ml of LB. 20 mM cholic acid were added to 5 ml of culture. No oxidation product 7-keto-3,12-dihydroxycholanic acid (RT: 7.5 min) could be detected with the knockout strain by means of HPLC. However, E. coli BL21(DE3) clearly showed 7α-HSDH activity against cholic acid (RT: 13.5 min). The 7α-HSDH gene was thus successfully knocked out (see FIG. 2).

The 7α-HSDH-free strain E. coli BL21(DE3) Δ7α-HSDH was thus successfully produced.

Example 2

Heterologous Expression of the 12α-HSDH Using E. Coli BL21(DE3) Δ7α-HSDH (Type 1)

The vector pET28a(+), Novagen, Darmstadt, which contains an MCS unter the control of a T7 promoter and transcription start and has a T7 terminator served for the expression of 12α-HSDH. The expression is induced by means of isopropyl-β-D-thiogalactopyranoside (IPTG).

For this, 12α-HSDH (short version) encoding sequences were PCR amplified (cf also PCT/EP2009/002190 of the Applicant). The PCR products were obtained using the genomic DNA of Clostridium sp. group P strain 48-50 as a template and the primer pairs:

```
                                              (SEQ ID NO: 5)
(5'-GGTATTCCATATGATCTTTGACGGAAAGGTCGC-3'
and (SEQ ID NO: 6)
5'-CGGGATCCCTAGGGGCGCTGACCC-3').
```

Italicized nucleotide radicals are surplus. Bold radicals encode a cleavage site. The other radicals are the homologous sequence to 12α-HSDH.

The PCR products were applied to an agarose gel, separated and excised from this. Subsequently, they were restricted with the aid of NdeI and BamHI and ligated with the pET28a(+) vector likewise cleaved with NdeI and BamHI.

The N-terminal His-Tag was subsequently removed by means of Quick-Change using the following primers. The plasmid was sequence and verified.

```
                                                                    (SEQ ID NO: 7)
5'-GTTTAACTTTAAGAAGGAGATATACCATGATCTTTGACGGAAAGGTCGCAATCATT-3'

(SEQ ID NO: 8)
5'-AATGATTGCGACCTTTCCGTCAAAGATCATGGTATATCTCCTTCTTAAAGTTAAAC-3'
```

For the investigation of the expression using E. coli BL21 (DE3) Δ7α-HSDH, chemically competent cells were produced according to the protocol indicated below. Vector pET28a+ (Novagen, contains T7 promoter and kanamycin resistance) with 12α-HSDH (without His-Tag) was transformed in E. coli BL21(DE3) Δ7α-HSDH.

Production of Chemically Competence Cells:

1 ml of overnight culture of E. coli was inoculated in 100 ml of LB medium. The cells were incubated at 37° C. and 180 rpm up to $OD_{600}$ 0.4-0.6. The cells were cooled on ice for 15 min and centrifuged for 10 min at 4° C. and 4000 rpm. The supernatant was removed and the cells were resuspended in 40 ml of precooled TfbI solution (potassium acetate 30 mM, rubidium chloride 100 mM, calcium chloride 10 mM, manganese chloride 50 mM, glycerol 15%). After incubation on ice for 15 min, the cells were centrifuged off. The supernatant was removed. The cells were resuspended in 4 ml of precooled TfbII solution (MOPS 10 mM, calcium chloride 75 mM, rubidium chloride 10 mM, glycerol 15%). For the transformation, 1 µl of plasmid DNA in 200 µl of competent cells was added and the mixture was incubated on ice for 10 min. The heat shock of the cells was carried out at 42° C. for 40 sec. Then 800 µl of LB medium was immediately added. The cells were incubated for 1 hour at 37° C. and 200 rpm. The transformed cells were centrifuged off and the supernatant was removed. The pellet was plated out on an LB agar plate. The plate was incubated at 37° C. for formation of colonies.

A colony was picked in 5 ml of LB. After 4 hours, 50 ml of LB were inoculated with 5 ml of pre-culture. At an $OD_{600}$ of about 0.8, the cells were induced with 0.5 mM IPTG. The cells were incubated overnight at 25° C. and 140 rpm. The cells were then centrifuged off, resuspended and digested. The 12α-HSDH activity was determined according to the method indicated above. The yield of 12α-HSDH was about 50 kU per liter of LB medium.

Example 3

Production of an *E. Coli* 7α-HSDH Knockout Mutant (*E. Coli* BL21 (DE3) hdhA⁻ KanR⁺) (Type 2) (Knockout by Gene Disruption)

The aim is the deletion of the interfering 7α-HSDH activity in the expression strain *E. coli* BL21 (DE3).

Using the method described below, an antibiotic resistance gene is inserted into the target gene of the 7α-HSDH, whereby the target gene is switched off.

3.1 Sequence Information for 7α-HSDH from *E. Coli* BL21 (DE3)

Cf. example 1

3.2 Primers Used

The following primers were prepared for the switching off of the 7α-HSDH from *E. coli* BL21(DE3):

Primer for the retargeting of the LI.LtrB introns, which is used in the TargeTron™ Gene Knockout System" (see section 3.3):

```
467|468a-IBS
                                                    (SEQ ID NO: 17)
AAAAAAGCTTATAATTATCCTTATAGGACGTCATGGTGCGCCCAGATAGGGTG

467|468a-EBS1d
                                                    (SEQ ID NO: 18)
CAGATTGTACAAATGTGGTGATAACAGATAAGTCGTCATGTTTAACTTACCTTTCTTTGT

467|468a-EBS2
                                                    (SEQ ID NO: 19)
TGAACGCAAGTTTCTAATTTCGGTTTCCTATCGATAGAGGAAAGTGTCT
```

```
EBS Universal:    5'-CGAAATTAGAAACTTGCGTTCAGTAAAC
```

(According to User Guide for the control reaction)

Insertion of the reprogrammed introns into the following sites

Location

```
467|468a
GCAGCTTTAGATGATGCATAGGAAGTCATG-intron-

TTTATATTTTTATTT
```

3.3 Production of the Knockout Mutant

The production of the knockout mutant was carried out with the aid of the TargeTron™ Gene Knockout System of Sigma Aldrich according to manufacturer's instructions. It was utilized for purification of the PCR product according to step B.6. of the TargeTron™ Gene Knockout System of the QIAquick PCR Purification Kit of Qiagen.

The ligation of the HindIII/BsrGI-digested intron PCR product in the linearized pACD4K-C vector was carried out as follows: The reaction took place overnight at 16° C.

20 µl Batch:

| | |
|---|---|
| 2 µl | pACD4K-C linear vector (40 ng) |
| 6 µl | HindIII/BsrGI-digested intron PCR product |
| 2 µl | ATP (10 mM) |
| 2 µl | Ligase buffer (10×) (Fermentas) |
| 2 µl | T4 Ligase (Fermentas) |
| 6 µl | $H_2O$ |

5 µl of ligation reaction solution were added to 200 µl chemically competence *E. coli* BL21(DE3) cells and incubated for 20 min on ice. The further transformation took place as described by the Herstellerseite.

The transformation batches were plated out on LB agar plates, containing 33 µg/mL of kanamycin. Kanamycin-resistant cells were picked and these were in each case reinoculated over several nights in 5 ml LB overnight cultures (in each case with 5 µl of a kanamycin solution (33 mg/ml)). Finally, a 200 ml LB culture (containing 200 µl of kanamycin solution (33 mg/mL)) was inoculated with an overnight culture and incubated at 37° C. and 180 rpm for 5 h in a shaker incubator. The temperature was then increased to 42° C. for 1 hour. A 5 mL LB overnight culture was inoculated with this culture, (in each case with 5 µl of a kanamycin solution (33 mg/mL)). After incubation overnight at 37° C. and 180 rpm, the culture was streaked on an LB agar plate containing 33 µg/mL of kanamycin. After overnight incubation at 37° C., colonies were picked and streaked on LB agar plates with 33 µg/mL of kanamycin and 34 µg/mL of chloramphenicol.

After overnight incubation at 37° C., chloramphenicol-sensitive mutants were found. This is necessary to confirm the loss of the plasmid which the inducible knockout system supports and is no longer needed after successful knockout The kanamycin resistance is only active with insertion. It has a deletion on the vector pACD4K-C. A colony that grows both on kanamycin and chloramphenicol thus most highly probably contains the desired knockout, but also additionally the pACD4K-C vector. Only if the strains are only additionally kanamycin-resistant, have they lost the pACD4K-C vector, but also the desired knockout.

3.4 Detection of the Knockouts

The 7α-HSDH Gene was Amplified by Means of Colony PCR Using the Primers

```
7alpha-ko-check_fwd
                                        SEQ ID NO: 20
(5'-TTAATTGAGCTCCTGTACCCCACCACC-3')
and
```

-continued

```
7alpha-ko-check_rev
                                   SEQ ID NO: 21
(5'-GTGTTTAATTCTGACAACCTGAGACTCGAC-3').
```

The fragment formed had a length of about 2.5-3 kb and was sequenced using the primer 7alpha-ko-check_fwd. Based on the sequencing, it could be detected that the DNA sequence of the 7α-HSDH is interrupted by an insert from the pACD4K vector, which results in the knockout of the 7α-HSDH. (Sequencing data not shown)

3.5 Expression of 12Alpha- and 7Beta-HSDH Mutants with the KO Strain

The usability of this knockout strain was verified, for example, by enzyme expressions of 12α- and 7β-HSDH mutants on the shaker flask scale (results not shown).

Example 4

Enzymatic Reaction of DHCA to 12-Keto-UDCA by the 7β-HSDH, FHD D221G and 3α-HSDH, in Each Case Produced with Use of the Knockout Strain E. Coli BL21(DE3) Δ7α-HSDH (type 1)

In this example, a two-stage enzymatic reaction of DHCA to 12-keto-UDOA with simultaneous cofactor regeneration using a special FDH mutant is to be investigated. Since the FDH mutant D221G used accepts both NADP$^+$ as well as NAD$^+$ as cofactor, no additional cofactor regeneration system has to be introduced into the reaction batch for the NADH-dependent 3α-HSDH.

The reaction is illustrated by way of example by the two partial reactions shown graphically below. FDH* designates the mutant FDH D221G.

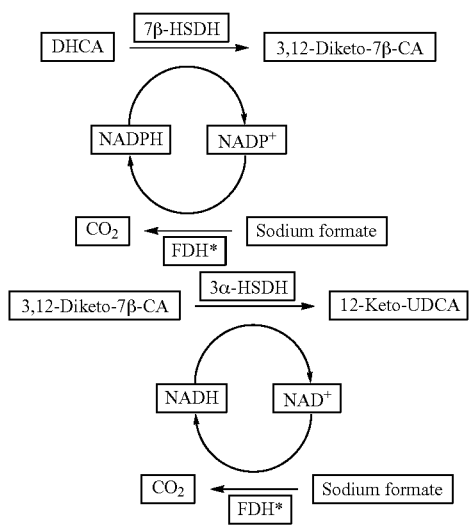

For this purpose, the enzymes 7β-HSDH from *Collinsella aerofaciens*, 3α-HSDH from *Comamonas testosteroni* and the FDH mutant D221G, derived from FDH from *Mycobacterium vaccae* were prepared separately from one another in the knockout strain *E. coli* BL21(DE3)/Δ7α-HSDH (type 1), prepared according to the above example 1, expressed and used for the reaction.

4.1 Plasmids Used,

Plasmids for the expression of 7β-HSDH, 3α-HSDH and FDH D221G:

pET28a(+)-7β-HSDH, pET22b(+)-3α-HSDH and pET21a(+)-FDH-D221 G.

4.2 Bacterial Strains and Culture Conditions:

The knockout strain *E. coli* BL21(DE3)Δ7α-HSDH (type 1) produced according to example 1 was cultured at 37° C. in LB medium, containing the necessary antibiotics. After induction with 0.5 mM IPTG, after reaching $OD_{600}$=0.8 the incubation was continued at 140 rpm for a period of 12 hours at 25° C.

4.3 Enzyme Overexpression and Purification

Overexpression of 7β-HSDH, 3α-HSDH and of the FDH mutant D221G in *E. coli* BL21(DE3)Δ7α-HSDH and enzyme purification took place under the following conditions:

The *E. coli* knockout strain was transformed using the expression construct. To this end, the strain containing the expression construct was multiplied in LB medium (2×400 ml in 2 liter shaker flasks) containing 30 µg/ml of kanamycin.

The cells were harvested by centrifugation (10 000×g, 15 min, 4° C.). The pellet was resuspended in 20 ml phosphate buffer (50 mM, pH 8, containing 0.1 mM PMSF). The cells were digested with constant cooling by ultrasound treatment for one minute (40 W power, 40% work interval and 1 min break) using a Sonifier 250 ultrasonic apparatus (Branson, Germany). The digestion was repeated three times. The cell extract was centrifuged (22 000×g, 20 min, 4° C.). Finally, the sample was transferred to a new tube and stored at −20° C. for further analysis. The protein concentration was determined using a BCA test kit (Thermo, USA) according to manufacturer's instructions. Moreover, the sample was analysed by 12.5% strength SDS-PAGE and staining with Coomassie Brilliant Blue. The purity of the protein was determined densitometrically with the aid of Scion Image Beta 4.0.2 (Scion, USA). The cell extracts of 7β-HSDH, 3α-HSDH and FDH were crude extracts. A further purification was superfluous, since the 7α-HSDH was already knocked out.

The yields per liter of culture medium (shaker flasks at $OD_{600}$~6) were as follows:

7β-HSDH: 3883 U (for DHCA and NADPH)

3α-HSDH: 6853 U (for DHCA and NADH)

FDH mutant: 47 U (for sodium formate and NAD$^+$).

The content and purity of the proteins was determined by means of SDS-PAGE and densitometer scanning by means of Scieon Image Beta 4.0.2 (Scieon, USA).

4.4 Enzymatic Synthesis of 12-Keto-UDCA on the Preparative Scale

An 800 ml reaction batch, containing 7β-HSDH (2.4 U×ml$^{-1}$), 3α-HSDH (2.4 U×ml$^{-1}$), FDH D221G (0.325 U×ml$^{-1}$), NADP$^+$ (10 µM), NAD$^+$ (10 µM), sodium formate (250 mM), DHCA (10 mM, 3.2 g) and potassium phosphate buffer (50 mM, pH 6), was stirred at 24° C. All three enzymes that were used in this experiment, were employed as cell crude extracts without an additional purification step. After 12 hours, the reaction was stopped by removal of the enzymes by means of ultrafiltration using a membrane with a pore size of 10 kDa (Millipore, USA). The product in the filtrate was purified by acidifying with hydrochloric acid to pH 2 and subsequent paper filtration. After drying the product at 60° C. overnight, 2.9 g of the desired product were obtained.

The product was analysed by means of HPLC and NMR.

Analysis Data (Partial):

$^1$H NMR (deuterated DMSO, 500 MHz) δ=3.92 (2H, m, H-3α and H-7β) and $^1$H-NMR (deuterated DMSO, 125 MHz) δ=69.38 (CH, 3-C); δ=69.09 (CH, 7-C); δ==213.86 (C, 12-C)

Yield: 90.6° A

Purity: 99° A

Assignment of the SEQ ID NOs:

| SEQ ID NO: | Description | Type |
|---|---|---|
| 1 | pIJ773 | NA |
| 2 | pJOE6038.1 | NA |
| 3 | PCR primer | NA |
| 4 | PCR primer | NA |
| 5 | PCR primer | NA |
| 6 | PCR primer | NA |
| 7 | PCR primer | NA |
| 8 | PCR primer | NA |
| 9 | 7α-HSDH | NA |
| 10 | 7α-HSDH | AA |
| 11 | 12α-HSDH; L | NA |
| 12 | 12α-HSDH; L | AA |
| 13 | 12α-HSDH; K | NA |
| 14 | 12α-HSDH; K | AA |
| 15 | 12α-HSDH mutant 37D12; K | NA |
| 16 | 12α-HSDH mutant 37D12; K | AA |
| 17 | Primer 467\|468a-IBS | NA |
| 18 | Primer 467\|468a-EBS1d | NA |
| 19 | Primer 467\|468a-EBS2 | NA |
| 20 | Primer 7alpha-ko-check_fwd | NA |
| 21 | Primer 7alpha-ko-check_rev | NA |
| 22 | FDH D221G with deletion and His-Tag | NA |
| 23 | FDH D221G with deletion and His-Tag | AA |
| 24 | 7β-HSDH | NA |
| 25 | 7β-HSDH | AA |
| 26 | Primer S 7beta_rev_HindIII | NA |
| 27 | Primer | NA |
| 28 | 3α-HSDH (*C. testosteroni*) | NA |
| 29 | 3α-HSDH (*C. testosteroni*) | AA |
| 30 | 3α-HSDH (*R. norvegicus*) | NA |
| 31 | 3α-HSDH (*R. norvegicus*) | AA |
| 32 | FDH wild-type, *M. vaccae* | AA |
| 33 | Primer fdh_for | NA |
| 34 | Primer fdh_rev | NA |
| 35 | Primer mt1 | NA |
| 36 | Primer NI_fdh_R | NA |
| 37 | FDH D221G | NA |
| 38 | FDH D221G | AA |

AA = amino acid sequence
NA = nucleic acid sequence
L = long form
K = short form Reference is made expressly to the disclosure of the publications cited herein.

The invention claimed is:

1. A recombinant microorganism of the genus *Escherichia* wherein the enzymatic activity of 7α-hydroxysteroid dehydrogenase (7α-HSDH) is inhibited, while the enzymatic activity of at least one functionally different hydroxysteroid dehydrogenase (HSDH) is contained expressibly wherein:

the expressed HSDH functionally different from the 7α-HSDH contains one of the following amino acid sequences:

a) a 3α-HSDH sequence selected from SEQ ID NO: 29 and 31;

b) a 7β-HSDH sequence selected from SEQ ID NO: 25;

c) a 12α-HSDH sequence selected from SEQ ID NO: 12, 14, 16; or d) an amino acid sequence derived therefrom, coding for an HSDH having a degree of identity of at least 90% to one of the sequences under a), b) and c); and wherein the recombinant microorganism is obtained from a precursor microorganism that endogenously expresses 7α-HSDH.

2. The recombinant microorganism as claimed in claim 1, in which the enzymatic activity of 7α-HSDH is inhibited by knocking out the nucleic acid sequence encoding 7α-HSDH by homologous recombination or by gene disruption.

3. The recombinant microorganism as claimed in claim 1, which recombinantly expresses the HSDH functionally different from the 7α-HSDH.

4. The recombinant microorganism as claimed in claim 2, wherein the knocked out 7α-HSDH has an amino acid sequence according to SEQ ID NO: 10 or is encoded by a nucleic acid sequence according to SEQ ID NO: 9.

5. A method for the recombinant production of a desired HSDH functionally different from a 7α-HSDH, wherein a recombinant microorganism as claimed in claim 1, in which the enzymatic activity of the 7α-HSDH is inhibited, is cultured under conditions under which the desired HSDH is expressed, and the HSDH thus expressed is isolated, wherein essentially no functional 7α-HSDH is detectable in the isolated HSDH.

6. A method for the selective enzymatic oxidation of hydroxysteroids, wherein the hydroxysteroid comprises a hydroxyl group in at least one of the positions 3α-, 7β- or 12α- of the steroid structure, and at least one further hydroxyl group in the 7α-position of the steroid structure, the method comprising reacting the hydroxysteroid in the presence of a recombinant microorganism as claimed in claim 1, and forming at least one oxidation product.

7. The method as claimed in claim 6, wherein the hydroxysteroid is cholic acid (CA) or a cholic acid derivative thereof.

8. The method as claimed in claim 7, wherein CA or a derivative thereof is reacted to give 12-ketochenodeoxycholic acid (12-keto-CDCA) or to give the corresponding derivative.

9. A method for the production of ursodeoxycholic acid (UDCA) of the formula (1)

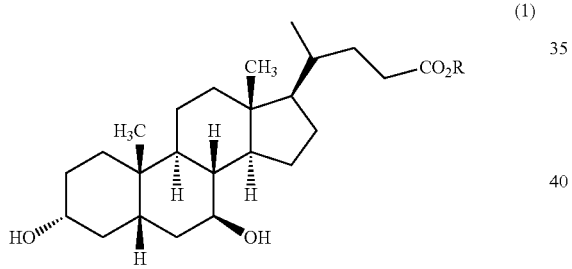

(1)

in which
R represents alkyl, $NR^1R^2$, H, an alkali metal ion or $N(R^3)_4^+$, in which the radicals $R^3$ are identical or different and represent H or alkyl,
wherein
  a) a cholic acid (CA) of the formula (2)

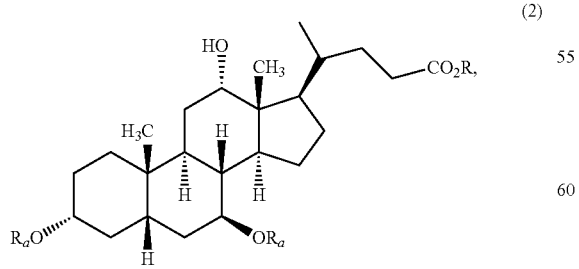

(2)

in which R has the meanings indicated above, and the radicals $R_a$ are identical or different and represent H or acyl, in the presence of a recombinant microorganism as claimed in claim 1 expressing a 12α-HSDH, is oxidized to the corresponding 12-ketochenodeoxycholic acid (12-keto CDCA) of the formula (3)

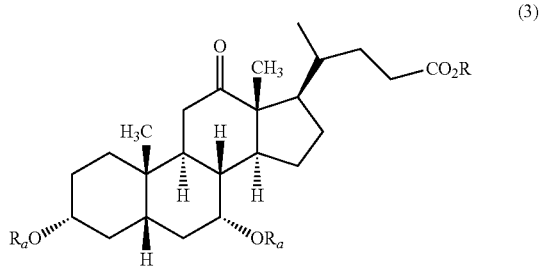

(3)

in which R and $R_a$ have the meanings indicated above, and subsequently
  b) 12-keto-CDCA of the formula (3) is reacted by deoxygenation to give chenodeoxycholic acid (CDCA) of the formula (4)

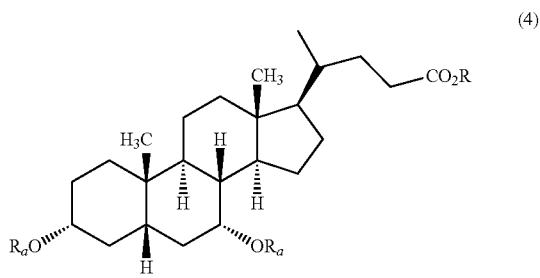

(4)

in which R and $R_a$ have the meanings indicated above, and
  c) CDCA of the formula (4) is chemically oxidized in position 7 to the 7-ketolithocholic acid (KLCA) of the formula (5)

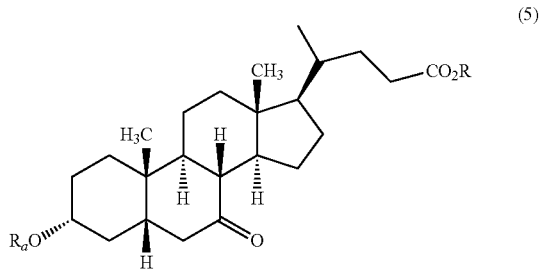

(5)

in which R and $R_a$ have the meanings indicated above; and
  d) KLCA of the formula (5) is reduced and
  e) the reaction product is optionally further purified.

10. A method for the selective enzymatic reduction of ketosteroids, wherein the ketosteroid comprises at least one keto group in position 3 or 12 of the steroid structure and at least one further keto group in position 7 of the steroid structure, the method comprising reacting the ketosteroid in the presence of a recombinant microorganism as claimed in claim 1 expressing a 7β-HSDH and at least one of a 3α-HSDH and a 12α-HSDH, and forming at least one reduction product.

11. The method as claimed in claim 6, further comprising conducting the method in the presence of whole, optionally immobilized cells of the recombinant microorganism.

12. A method for the production of ursodeoxycholic acid (UDCA) of the formula (1)

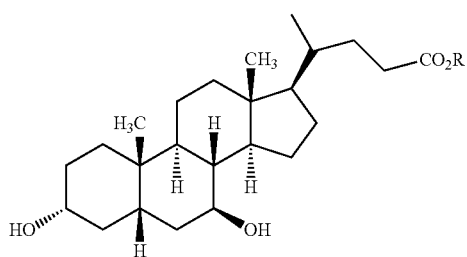

in which
R represents alkyl, NR$^1$R$^2$, H, an alkali metal ion or N(R$^3$)$_4^+$, in which the radicals R$^3$ are identical or different and represent H or alkyl, wherein
a) optionally a cholic acid (CA) of the formula (2)

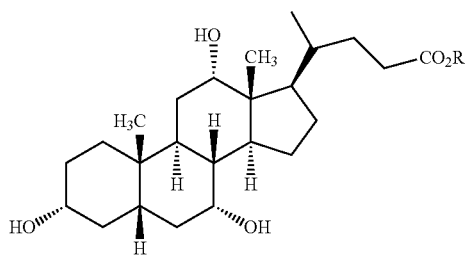

in which R has the meanings indicated above is chemically oxidized to the dehydrocholic acid (DHCA) of the formula (3)

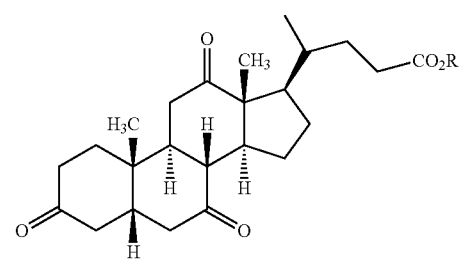

in which R has the meanings indicated above;

b) DHCA is reduced in the presence of a recombinant microorganism as claimed in claim 1 expressing a 7β-HSDH and a 3α-HSDH to the corresponding 12-ketoursodeoxycholic acid (12-keto UDCA) of the formula (5)

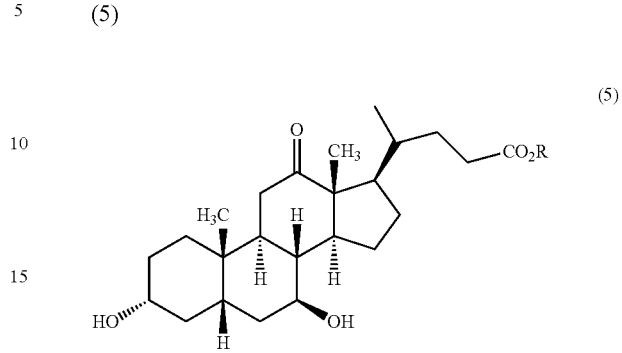

in which R has the meanings indicated above, and subsequently
c) 12-keto-UDCA of the formula (5) is reduced chemically to UDCA; and
d) the reaction product is optionally further purified.

13. The method as claimed in claim 6, further comprising a cofactor regeneration step.

14. The recombinant microorganism as claimed in claim 2, wherein the nucleic acid sequence encoding 7α-HSDH is knocked out by insertion of a nucleic acid sequence inhibiting the enzyme function of the encoded gene product.

15. The recombinant microorganism as claimed in claim 1, wherein the precursor microorganism is *E. coli*.

16. The method as claimed in claim 6, wherein the hydroxyl group is in the 12α-position of the steroid structure.

17. The method as claimed in claim 6, wherein the hydroxysteroid is reacted in the presence of a 12α-HSDH.

18. The method as claimed in claim 6, further comprising isolating the at least one oxidation product formed from the reaction mixture.

19. The method as claimed in claim 7, wherein the cholic acid derivative is a salt, amide or alkyl ester.

20. The method as claimed in claim 10, wherein the ketosteroid has a keto group in position 12, in position 3 or in positions 12 and 3 of the steroid structure.

21. The method as claimed in claim 10, further comprising conducting the method in the presence of whole, optionally immobilized cells of the recombinant microorganism.

22. The method as claimed in claim 10, further comprising isolating the at least one oxidation product formed from the reaction mixture.

* * * * *